US012635675B2

(12) United States Patent
Lu et al.

(10) Patent No.: US 12,635,675 B2
(45) Date of Patent: May 26, 2026

(54) ALZHEIMERS DISEASE ANIMAL MODEL AND USE THEREOF

(71) Applicant: TSINGHUA UNIVERSITY, Beijing (CN)

(72) Inventors: Bai Lu, Beijing (CN); Keliang Pang, Beijing (CN); Wei Guo, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 1142 days.

(21) Appl. No.: 16/982,383

(22) PCT Filed: Mar. 19, 2019

(86) PCT No.: PCT/CN2019/078754
§ 371 (c)(1),
(2) Date: Sep. 18, 2020

(87) PCT Pub. No.: WO2019/179445
PCT Pub. Date: Sep. 26, 2019

(65) Prior Publication Data
US 2021/0037798 A1 Feb. 11, 2021

(30) Foreign Application Priority Data
Mar. 20, 2018 (WO) ................ PCT/CN2018/079552

(51) Int. Cl.
*A01K 67/0278* (2024.01)
*A61K 49/00* (2006.01)

(52) U.S. Cl.
CPC ...... *A01K 67/0278* (2013.01); *A61K 49/0008* (2013.01); *A01K 2217/072* (2013.01); *A01K 2227/105* (2013.01); *A01K 2267/0312* (2013.01)

(58) Field of Classification Search
CPC .......... A01K 67/0278; A01K 2217/072; A01K 2227/105; A01K 2267/0312; A61K 49/0008; C07K 2319/00; C07K 14/4711
See application file for complete search history.

(56) References Cited

U.S. PATENT DOCUMENTS

2006/0241038 A1* 10/2006 Watanabe ............... A61P 43/00
514/17.8
2006/0270841 A1 11/2006 Espeseth et al.
2006/0272038 A1 11/2006 De Vivo et al.
2007/0294779 A1* 12/2007 Saido ................. C12N 15/8509
800/14
2022/0033846 A1* 2/2022 Tremblay ....... C12Y 305/04004

FOREIGN PATENT DOCUMENTS

WO WO 03/072041 A2 9/2003
WO WO 2006/128163 A2 11/2006

OTHER PUBLICATIONS

Saito et al. "Single App knock-in mouse models of Alzheimer's disease." Nature neuroscience 17.5 (2014): 661-663 (Year: 2014).*
International Search Report issued on Jun. 18, 2019 in PCT/CN2019/078754 filed on Mar. 19, 2019.
Saito et al., "Single App knock-in mouse models of Alzheimer's disease" Nature Neuroscience, Brief Communications, 2014, vol. 17, No. 5, pp. 661-664.
Bugos. O., et al., "Beyond the Rat Models of Human Neurodegenerative Disorders", Cell Mol. Neurobiol., 2009, vol. 29. pp. 859-869.
Flood, D.G., et al., "A transgenic rat model of Alzheimer's disease with extracellular Aβ deposition", Neurobiology of Aging, 2009, vol. 30, pp. 1078-1090.
Liu, L., et al., "A transgenic rat that develops Alzheimer's disease-like amyloid pathology, deficits in synaptic plasticity and cognitive impairment", Neurobiology of Disease. 2008, vol. 31, pp. 46-57.
Saito, T., et al., "Single App knock-in mouse models of Alzheimer's disease", Nature Neuroscience, vol. 17, No. 5, May 2014, pp. 661-663 (4 total pages).
Masuda, A., et al., "Cognitive deficits in single App knock-in mouse models", Neurobiology of Learning and Memory, vol. 135, 2016, pp. 73-82.
Remy, S., et al., "Generation of gene-edited rats by delivery of CRISPR/Cas9 protein and donor DNA Into intact zygotes using electroporation", Scientific Reports, vol. 7, 2017, pp. 1-13.

* cited by examiner

*Primary Examiner* — Alexander W Nicol
(74) *Attorney, Agent, or Firm* — Merchant & Gould P.C.; Daniel J. Pereira

(57) ABSTRACT
Provided is an Alzheimer's disease rat model or a tissue or cell thereof, which comprises a chimeric APP gene encoding a modified APP and use thereof.

8 Claims, 73 Drawing Sheets

Specification includes a Sequence Listing.

Het
3 M

WT — Homo

1 M

2 M

6 Months

12 Months

WT

Homo

○  WT
▦  Homo

12 Months

WT

Homo

Homo

12 Months

6 Months

12M
WT

12M
Homo

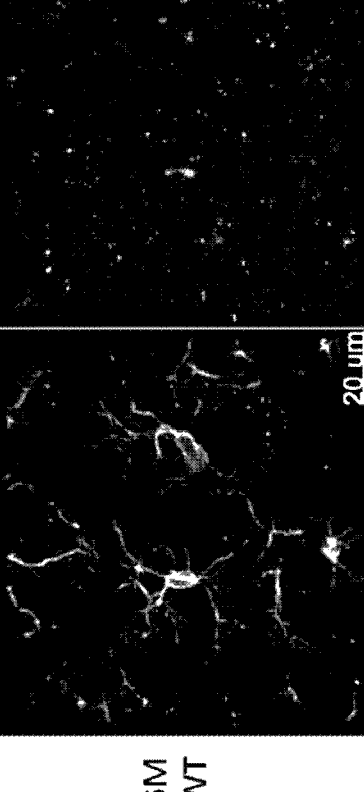
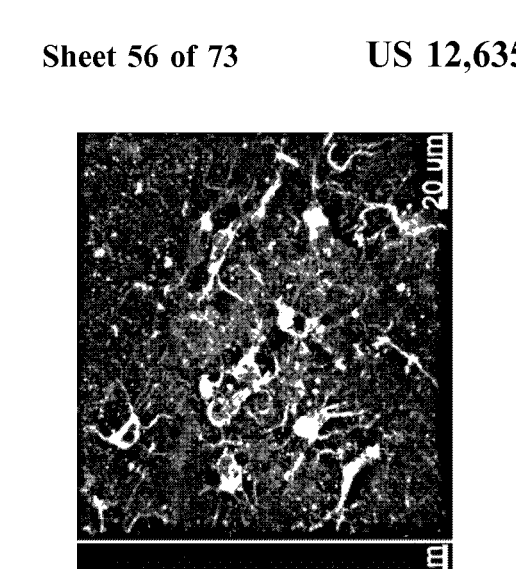
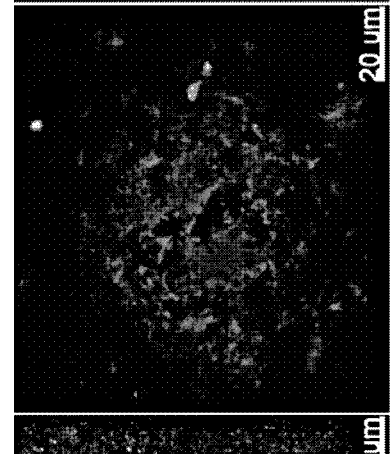
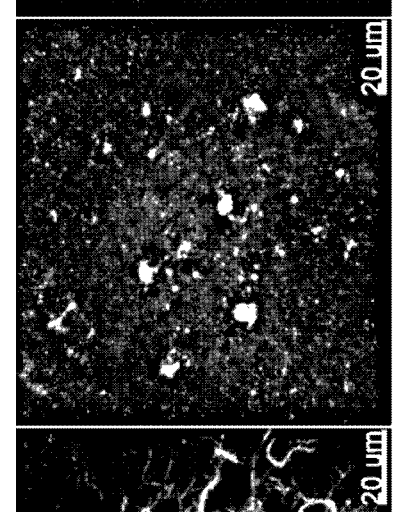
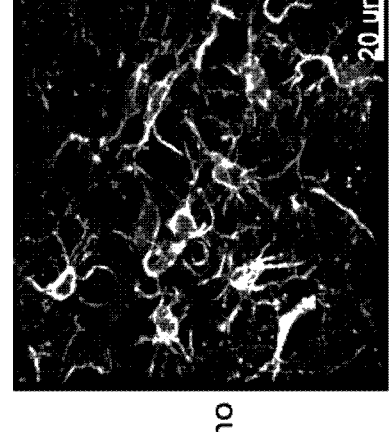
FIG. 48A
FIG. 48B

12M
WT

12M
Homo

12 Months

9M
WT

9M
Homo

6M WT

6M HOMO

WT Homo

22 M

NeuN(546 nm)   30 um   NeuN(546 nm)   30 um

| Age | Type | Brain Weight (g) | | |
|------|-------------|-------|-------|-------|
| 6 M | WT Rat | 2.479 | 2.495 | 2.472 |
| 6 M | AD Rat(Homo) | 2.220 | 2.041 | 2.243 |
| 22 M | WT Rat | 2.570 | 2.519 | 2.482 |
| 22 M | AD Rat(Homo) | 2.064 | 2.190 | 2.099 |

SEQUENCE LISTING

```
<160> NUMBER OF SEQ ID NOS: 14

<210> SEQ ID NO 1
<211> LENGTH: 770
<212> TYPE: PRT
<213> ORGANISM: Rattus norvegicus

<400> SEQUENCE: 1

Met Leu Pro Ser Leu Ala Leu Leu Leu Leu Ala Ala Trp Thr Val Arg
1               5                   10                  15

Ala Leu Glu Val Pro Thr Asp Gly Asn Ala Gly Leu Leu Ala Glu Pro
            20                  25                  30

Gln Ile Ala Met Phe Cys Gly Lys Leu Asn Met His Met Asn Val Gln
```

-continued

```
                35                        40                        45

Asn Gly Lys Trp Glu Ser Asp Pro Ser Gly Thr Lys Thr Cys Ile Gly
    50                        55                        60

Thr Lys Glu Gly Ile Leu Gln Tyr Cys Gln Glu Val Tyr Pro Glu Leu
65                        70                        75                        80

Gln Ile Thr Asn Val Val Glu Ala Asn Gln Pro Val Thr Ile Gln Asn
                85                        90                        95

Trp Cys Lys Arg Gly Arg Lys Gln Cys Lys Thr His Thr His Ile Val
                100                       105                       110

Ile Pro Tyr Arg Cys Leu Val Gly Glu Phe Val Ser Asp Ala Leu Leu
                115                       120                       125

Val Pro Asp Lys Cys Lys Phe Leu His Gln Glu Arg Met Asp Val Cys
    130                       135                       140

Glu Thr His Leu His Trp His Thr Val Ala Lys Glu Thr Cys Ser Glu
145                       150                       155                       160

Lys Ser Thr Asn Leu His Asp Tyr Gly Met Leu Leu Pro Cys Gly Ile
                165                       170                       175

Asp Lys Phe Arg Gly Val Glu Phe Val Cys Cys Pro Leu Ala Glu Glu
                180                       185                       190

Ser Asp Ser Ile Asp Ser Ala Asp Ala Glu Glu Asp Asp Ser Asp Val
                195                       200                       205

Trp Trp Gly Gly Ala Asp Thr Asp Tyr Ala Asp Gly Gly Glu Asp Lys
    210                       215                       220

Val Val Glu Val Ala Glu Glu Glu Val Ala Asp Val Glu Glu Glu
225                       230                       235                       240

Glu Ala Glu Asp Asp Glu Asp Val Glu Asp Gly Asp Glu Val Glu Glu
                245                       250                       255

Glu Ala Glu Glu Pro Tyr Glu Glu Ala Thr Glu Arg Thr Thr Ser Ile
                260                       265                       270

Ala Thr Thr Thr Thr Thr Thr Thr Glu Ser Val Glu Glu Val Val Arg
                275                       280                       285

Glu Val Cys Ser Glu Gln Ala Glu Thr Gly Pro Cys Arg Ala Met Ile
    290                       295                       300

Ser Arg Trp Tyr Phe Asp Val Thr Glu Gly Lys Cys Ala Pro Phe Phe
305                       310                       315                       320

Tyr Gly Gly Cys Gly Gly Asn Arg Asn Asn Phe Asp Thr Glu Glu Tyr
                325                       330                       335

Cys Met Ala Val Cys Gly Ser Val Ser Ser Gln Ser Leu Leu Lys Thr
                340                       345                       350

Thr Ser Glu Pro Leu Pro Gln Asp Pro Val Lys Leu Pro Thr Thr Ala
                355                       360                       365

Ala Ser Thr Pro Asp Ala Val Asp Lys Tyr Leu Glu Thr Pro Gly Asp
    370                       375                       380

Glu Asn Glu His Ala His Phe Gln Lys Ala Lys Glu Arg Leu Glu Ala
385                       390                       395                       400

Lys His Arg Glu Arg Met Ser Gln Val Met Arg Glu Trp Glu Glu Ala
                405                       410                       415

Glu Arg Gln Ala Lys Asn Leu Pro Lys Ala Asp Lys Lys Ala Val Ile
                420                       425                       430

Gln His Phe Gln Glu Lys Val Glu Ser Leu Glu Gln Glu Ala Ala Asn
                435                       440                       445

Glu Arg Gln Gln Leu Val Glu Thr His Met Ala Arg Val Glu Ala Met
    450                       455                       460
```

-continued

```
Leu Asn Asp Arg Arg Arg Leu Ala Leu Glu Asn Tyr Ile Thr Ala Leu
465                 470                 475                 480

Gln Ala Val Pro Pro Arg Pro His His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
            515                 520                 525

Gln Val Met Thr His Leu Arg Val Ile Tyr Glu Arg Met Asn Gln Ser
        530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
            595                 600                 605

Val Asn Gly Glu Phe Ser Leu Asp Asp Leu Gln Pro Trp His Pro Phe
        610                 615                 620

Gly Val Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Lys Met Asp
            660                 665                 670

Ala Glu Phe Gly His Asp Ser Gly Phe Glu Val Arg His Gln Lys Leu
            675                 680                 685

Val Phe Phe Ala Glu Asp Val Gly Ser Asn Lys Gly Ala Ile Ile Gly
        690                 695                 700

Leu Met Val Gly Gly Val Val Ile Ala Thr Val Ile Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
            755                 760                 765

Gln Asn
    770
```

```
<210> SEQ ID NO 2
<211> LENGTH: 770
<212> TYPE: PRT
<213> ORGANISM: Artificial Sequence
<220> FEATURE:
<223> OTHER INFORMATION: mutated APP

<400> SEQUENCE: 2

Met Leu Pro Ser Leu Ala Leu Leu Leu Leu Ala Ala Trp Thr Val Arg
1               5                   10                  15

Ala Leu Glu Val Pro Thr Asp Gly Asn Ala Gly Leu Leu Ala Glu Pro
                20                  25                  30

Gln Ile Ala Met Phe Cys Gly Lys Leu Asn Met His Met Asn Val Gln
            35                  40                  45
```

-continued

```
Asn Gly Lys Trp Glu Ser Asp Pro Ser Gly Thr Lys Thr Cys Ile Gly
    50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Thr His Ile Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
    130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
                180                 185                 190

Ser Asp Ser Ile Asp Ser Ala Asp Ala Glu Glu Asp Asp Ser Asp Val
            195                 200                 205

Trp Trp Gly Gly Ala Asp Thr Asp Tyr Ala Asp Gly Gly Glu Asp Lys
    210                 215                 220

Val Val Glu Val Ala Glu Glu Glu Val Ala Asp Val Glu Glu Glu
225                 230                 235                 240

Glu Ala Glu Asp Asp Glu Asp Val Glu Asp Gly Asp Glu Val Glu Glu
                245                 250                 255

Glu Ala Glu Glu Pro Tyr Glu Glu Ala Thr Glu Arg Thr Thr Ser Ile
                260                 265                 270

Ala Thr Thr Thr Thr Thr Thr Thr Glu Ser Val Glu Glu Val Val Arg
            275                 280                 285

Glu Val Cys Ser Glu Gln Ala Glu Thr Gly Pro Cys Arg Ala Met Ile
    290                 295                 300

Ser Arg Trp Tyr Phe Asp Val Thr Glu Gly Lys Cys Ala Pro Phe Phe
305                 310                 315                 320

Tyr Gly Gly Cys Gly Gly Asn Arg Asn Asn Phe Asp Thr Glu Glu Tyr
                325                 330                 335

Cys Met Ala Val Cys Gly Ser Val Ser Ser Gln Ser Leu Leu Lys Thr
                340                 345                 350

Thr Ser Glu Pro Leu Pro Gln Asp Pro Val Lys Leu Pro Thr Thr Ala
            355                 360                 365

Ala Ser Thr Pro Asp Ala Val Asp Lys Tyr Leu Glu Thr Pro Gly Asp
    370                 375                 380

Glu Asn Glu His Ala His Phe Gln Lys Ala Lys Glu Arg Leu Glu Ala
385                 390                 395                 400

Lys His Arg Glu Arg Met Ser Gln Val Met Arg Glu Trp Glu Glu Ala
                405                 410                 415

Glu Arg Gln Ala Lys Asn Leu Pro Lys Ala Asp Lys Lys Ala Val Ile
                420                 425                 430

Gln His Phe Gln Glu Lys Val Glu Ser Leu Glu Gln Glu Ala Ala Asn
            435                 440                 445

Glu Arg Gln Gln Leu Val Glu Thr His Met Ala Arg Val Glu Ala Met
    450                 455                 460
```

Leu Asn Asp Arg Arg Arg Leu Ala Leu Glu Asn Tyr Ile Thr Ala Leu
465                 470                 475                 480

Gln Ala Val Pro Pro Arg Pro His His Val Phe Asn Met Leu Lys Lys
                485                 490                 495

Tyr Val Arg Ala Glu Gln Lys Asp Arg Gln His Thr Leu Lys His Phe
            500                 505                 510

Glu His Val Arg Met Val Asp Pro Lys Lys Ala Ala Gln Ile Arg Ser
        515                 520                 525

Gln Val Met Thr His Leu Arg Val Ile Tyr Glu Arg Met Asn Gln Ser
    530                 535                 540

Leu Ser Leu Leu Tyr Asn Val Pro Ala Val Ala Glu Glu Ile Gln Asp
545                 550                 555                 560

Glu Val Asp Glu Leu Leu Gln Lys Glu Gln Asn Tyr Ser Asp Asp Val
                565                 570                 575

Leu Ala Asn Met Ile Ser Glu Pro Arg Ile Ser Tyr Gly Asn Asp Ala
            580                 585                 590

Leu Met Pro Ser Leu Thr Glu Thr Lys Thr Thr Val Glu Leu Leu Pro
        595                 600                 605

Val Asn Gly Glu Phe Ser Leu Asp Asp Leu Gln Pro Trp His Pro Phe
    610                 615                 620

Gly Val Asp Ser Val Pro Ala Asn Thr Glu Asn Glu Val Glu Pro Val
625                 630                 635                 640

Asp Ala Arg Pro Ala Ala Asp Arg Gly Leu Thr Thr Arg Pro Gly Ser
                645                 650                 655

Gly Leu Thr Asn Ile Lys Thr Glu Glu Ile Ser Glu Val Asn Leu Asp
            660                 665                 670

Ala Glu Phe Arg His Asp Ser Gly Tyr Glu Val His His Gln Lys Leu
        675                 680                 685

Val Phe Phe Ala Gly Asp Val Gly Ser Asn Lys Gly Ala Ile Ile Gly
    690                 695                 700

Leu Met Val Gly Gly Val Val Ile Ala Thr Val Phe Val Ile Thr Leu
705                 710                 715                 720

Val Met Leu Lys Lys Lys Gln Tyr Thr Ser Ile His His Gly Val Val
                725                 730                 735

Glu Val Asp Ala Ala Val Thr Pro Glu Glu Arg His Leu Ser Lys Met
            740                 745                 750

Gln Gln Asn Gly Tyr Glu Asn Pro Thr Tyr Lys Phe Phe Glu Gln Met
        755                 760                 765

Gln Asn
    770

<210> SEQ ID NO 3
<211> LENGTH: 20
<212> TYPE: DNA
<213> ORGANISM: Artificial Sequence
<220> FEATURE:
<223> OTHER INFORMATION: sgRNA2-target seq 1

<400> SEQUENCE: 3
gtacctaaga gacgttgact                                                    20

<210> SEQ ID NO 4
<211> LENGTH: 20
<212> TYPE: DNA
<213> ORGANISM: Artificial Sequence
<220> FEATURE:
<223> OTHER INFORMATION: sgRNA6-target seq 2

<400> SEQUENCE: 4
tcacggtgtc agtggagagt                                          20

<210> SEQ ID NO 5
<211> LENGTH: 20
<212> TYPE: DNA
<213> ORGANISM: Artificial Sequence
<220> FEATURE:
<223> OTHER INFORMATION: sgRNA5-target seq

<400> SEQUENCE: 5
gcaattagaa caacgctcca                                          20

<210> SEQ ID NO 6
<211> LENGTH: 20
<212> TYPE: DNA
<213> ORGANISM: Artificial Sequence
<220> FEATURE:
<223> OTHER INFORMATION: sgRNA1-target seq

<400> SEQUENCE: 6
agaacaacgc tccaagggga                                          20

<210> SEQ ID NO 7
<211> LENGTH: 20
<212> TYPE: DNA
<213> ORGANISM: Artificial Sequence
<220> FEATURE:
<223> OTHER INFORMATION: sgRNA3-target seq

<400> SEQUENCE: 7
ccgtgtatag ctagggagct                                          20

<210> SEQ ID NO 8
<211> LENGTH: 20
<212> TYPE: DNA
<213> ORGANISM: Artificial Sequence
<220> FEATURE:
<223> OTHER INFORMATION: sgRNA4-target seq

<400> SEQUENCE: 8
aaaacgaaca ttaacgacct                                          20

<210> SEQ ID NO 9
<211> LENGTH: 20
<212> TYPE: DNA
<213> ORGANISM: Artificial Sequence
<220> FEATURE:
<223> OTHER INFORMATION: sgRNA7-target seq

<400> SEQUENCE: 9
tccctgcttg gctggtctgt                                          20

<210> SEQ ID NO 10
<211> LENGTH: 20
<212> TYPE: DNA
<213> ORGANISM: Artificial Sequence
<220> FEATURE:
<223> OTHER INFORMATION: sgRNA8-target seq

<400> SEQUENCE: 10
tgacatagca ctgacttctg                                          20

<210> SEQ ID NO 11

-continued

```
<211> LENGTH: 20
<212> TYPE: DNA
<213> ORGANISM: Artificial Sequence
<220> FEATURE:
<223> OTHER INFORMATION: sgRNA9-target seq

<400> SEQUENCE: 11
ctgtggtaag catccctgct                                              20

<210> SEQ ID NO 12
<211> LENGTH: 20
<212> TYPE: DNA
<213> ORGANISM: Artificial Sequence
<220> FEATURE:
<223> OTHER INFORMATION: sgRNA10-target seq

<400> SEQUENCE: 12
tgcccacaga ccagccaagc                                              20

<210> SEQ ID NO 13
<211> LENGTH: 9
<212> TYPE: PRT
<213> ORGANISM: Artificial Sequence
<220> FEATURE:
<223> OTHER INFORMATION: meganuclease motif

<400> SEQUENCE: 13

Leu Ala Gly Leu Ile Asp Ala Asp Gly
1               5

<210> SEQ ID NO 14
<211> LENGTH: 56
<212> TYPE: PRT
<213> ORGANISM: Artificial Sequence
<220> FEATURE:
<223> OTHER INFORMATION: meganuclease motif

<400> SEQUENCE: 14

Lys Met Asp Ala Glu Phe Arg His Asp Ser Gly Tyr Glu Val His His
1               5                   10                  15

Gln Lys Leu Val Phe Phe Ala Gly Asp Val Gly Ser Asn Lys Gly Ala
            20                  25                  30

Ile Ile Gly Leu Met Val Gly Gly Val Val Ile Ala Thr Val Phe Val
        35                  40                  45

Ile Thr Leu Val Met Leu Lys Lys
    50                  55
```

1

ALZHEIMERS DISEASE ANIMAL MODEL AND USE THEREOF

This application is a National Stage Application and claims priority under 35 U.S.C. § 371 to Patent Cooperation Treaty application PCT/CN2019/078754, filed Mar. 19, 2019, which claims the benefit of Patent Cooperation Treaty application PCT/CN2018/079552, filed Mar. 20, 2018. Priority is claimed to these applications and the disclosures of these prior applications are considered part of the disclosure of this application and to the extent allowed the entire contents of the aforementioned applications are incorporated herein.

BACKGROUND OF THE INVENTION

As many countries become aging societies, patients with elderly dementia have increased significantly and Alzheimer's disease (AD) is one of the major causes of elderly dementia. Based on genetic abnormality in familial Alzheimer's disease (FAD), the mechanisms for formation of senile plaque and neurofibrillary tangle have been revealed gradually. However, very few (if any) effective therapies of AD have been developed so far and there is an urgent need to further study the mechanisms and treatment of AD.

In the research of AD, a big hurdle is the lack of appropriate animal models. Transgenic mouse models overexpressing the amyloid precursor protein (APP) have been developed, such as the Tg2576 mouse (Science, 274:99-102 (1996)) and other transgenic amyloid precursor protein (APP) mouse models, e.g., as reported in Nature, 373:523-7 (1995) and Nature, 395:755-6 (1998). However, these APP overexpressing animal models often fail to reproduce the pathologies observed in human, which made it difficult or even impossible to develop a clinically effective AD therapy. For example, APP overexpression was observed to perturb axonal transport due to an interaction with kinesin. In addition, in these APP transgenic mice, not only full-length APP, but also other APP fragments (such as soluble amyloid precursor protein (sAPP), C-terminal fragment-beta, C-terminal fragment-alpha and amyloid precursor protein intracellular domain (AICD)) are overproduced, which may affect normal physiological functions. Often times, cross-breeding APP transgenic mice with other mutant mice is likely to generate even more complicated artifacts. The use of artificial promoters often results in transgene expression in cells not necessarily identical to those expressing endogenous APP and artificial promoters may compete with endogenous promoters for common transcription factors. Sometimes, the transgene is inserted into a gene locus of the host animal, often in multi-copy manner, which may destroy the functions of endogenous genes. In addition, the APP transgenic mice often die of unknown causes.

Although over 120 mouse models have been established so far for studying AD, very few, of them, if any, could authentically reproduce all the neuropathologic phenotypes seen in human AD patients. More importantly, recently, quite a few candidate AD therapies shown to be effective in the AD mouse models failed in clinical trials. All of these problems may be due to the intrinsic limits associated with mouse as an AD animal model.

For decades, people tried to develop other animal models that are physiologically, genetically and morphologically closer to humans, such as rat models or non-human primate (NHP) models. However, it is often extremely difficult to develop a desired NHP model, due to the lack of suitable technologies to perform gene-editing in NHP and the difficulties in propagating and maintaining NHPs.

Attempts have also been made in rats. However, compared to mice, rat one-cell embryos have less visible pronuclei and more flexible plasma and pronuclear membranes, making transgene injection in pronuclei more difficult. The low survival of embryos following injection also contributes to making rat transgenesis more demanding and time consuming. Additionally, tools for manipulation of the rat genome are less readily available. Until recently, embryonic stem (ES) cell-based targeting technology was not available, as viable rat ES cells had been difficult to obtain. Most currently known rat AD models do not represent accurate model systems for AD, as they do not exhibit neuritic plaques, neurofibrillary tangles (NFTs) or neuronal loss. For the very few rat AD models carrying the exact same construct as in corresponding mouse AD models, the phenotypes observed in rats are often much weaker and much less aggressive.

Accordingly, it is highly desired to develop a new animal model that is clinically relevant and could more authentically reproduce the phenotypes of human AD patients.

SUMMARY OF THE INVENTION

The present disclosure provides a novel animal model of Alzheimer's disease (AD) and use thereof. Specifically, the present disclosure provides a rat model of Alzheimer's disease wherein the endogenous amyloid precursor protein (APP) gene is at least partially substituted by a heterologous nucleic acid sequence encoding at least a part of a modified APP. In the rat model of the present disclosure, not only full-length APP but also other APP fragments (such as CTF-α, CTF-β and AICD) are physiologically expressed (e.g., not overexpressed comparing to a corresponding wild-type rat). In addition, the rat model of the present disclosure (e.g., when heterozygous for the modified APP) shows Aβ oligomer at an age of 3 months or earlier, at an age of 2 months or earlier, or even at an age of 1 month or earlier (e.g., when homozygous for the modified APP). In some cases, the rat model of the present disclosure (e.g., when heterozygous for the modified APP) shows Amyloid plaque at an age of 4 months or earlier, even at an age of 1 month or earlier (e.g., when homozygous for the modified APP), morphology and/or structure of the Amyloid plaques changes with age. No substantial Aβ accumulation was observed in the cerebellum of the present rat model, which is consistent with the situation observed in human AD patients.

Furthermore, the rat model of the present disclosure (e.g., when heterozygous or homozygous for the modified APP) may have one or more of the following properties: 1) showing hyper-phosphorylation of tau (e.g., in the rat brain), as revealed by increased phosphorylation of Thr231 and/or Ser202 of tau (e.g., in the rat brain), comparing to that in a corresponding wildtype rat; 2) showing conformationally altered tau protein, such as aggregation of tau protein (e.g., as tau oligomers), as revealed with anti-MC1 antibody staining, and co-localization of the tau oligomers with tubulin/microtubules (e.g., as revealed with anti-MAP2 and anti-MC1 double staining); 3) showing neuronal loss, such as apoptosis, for example, apoptosis of a neuronal cell, as may be revealed by increased level of Bax, Bcl-2, Cl-caspase3 and/or Pro-caspase3 in the rat (e.g., in the rat brain) comparing to that in a corresponding wildtype rat; 4) showing neuronal loss, such as necrosis (e.g., necroptosis), for example, necrosis of a neuronal cell, as may be revealed by increased level of receptor-interacting protein kinase 1 (RIPK1) and/or phosphorylated mixed lineage kinase domain-like protein (pMLKL) in said rat (e.g., in the rat brain) comparing to that in a corresponding wildtype rat, while receptor-interacting protein kinase 3 (RIPK3) RIPK3 level in said rat may be comparable to that in a corresponding wildtype rat; 5) formation of necrosomes in said rat (e.g., in the rat brain); 6) increased co-localization of RIPK1 and RIPK3 in said rat (e.g., in the rat brain), comparing to that in a corresponding wildtype rat; 7) increased co-localization of RIPK1 and mixed lineage kinase domain-like protein (MLKL) in said rat (e.g., in the rat brain), comparing to that in a corresponding wildtype rat; 8) increased MLKL aggregation in said rat (e.g., in the rat brain), comparing to that in a corresponding wildtype rat; 9) showing gliosis (e.g., in the rat brain), such as microgliosis and/or astrocytosis and the microgliosis and/or astrocytosis may be associated with Amyloid plaques; 10) increased RIPK1 and microglia (e.g., as revealed with anti-Iba1 staining) co-localization in said rat (e.g., in the rat brain), comparing to that in a corresponding wildtype rat; 11) increased RIPK1, microglia (e.g., as revealed with anti-Iba1 staining) and the Amyloid plaques co-localization in said rat (e.g., in the rat brain), comparing to that in a corresponding wildtype rat; 12) increased RIPK3 and microglia (e.g., as revealed by Iba1 staining) co-localization in said rat (e.g., in the rat brain), comparing to that in a corresponding wildtype rat; 13) increased RIPK3, microglia (e.g., as revealed by Iba1 staining) and the Amyloid plaques co-localization in said rat (e.g., in the rat brain), comparing to that in a corresponding wildtype rat; 14) showing synaptic degeneration (e.g., in the rat brain), as may be revealed by swelling and/or hollowing of postsynaptic density; 15) showing neuronal cell loss (e.g., as reflected by decreased number of Neu-N positive neurons) in said rat (e.g., in the rat brain), comparing to that in a corresponding wildtype rat; 16) showing brain morphological and/or weight changes in said rat, such as a reduction of brain size, an appearance and/or enlarging of a ventricular cavity, and/or a damage in hippocampus in said rat; and/or 17) showing cognitive impairment in said rat, as may be detected in an open field test, a Morris maze test and/or a T maze working memory test.

The novel AD model of the present disclosure would serve as an important tool for identifying new therapeutic/prophylactic agents of AD. In addition, the novel AD model of the present disclosure would serve as an important tool for identifying new biomarker(s) for diagnosis of AD, and/or for evaluating severity or progress of AD.

Accordingly, in one aspect, the present disclosure provides a rat or a living part thereof, comprising a chimeric APP gene encoding a modified APP. Comparing to a wildtype rat APP as set forth in SEQ ID NO:1, the modified APP comprises an amino acid substitution at the following residues: K670, M671, I716 and E693.

In some embodiments, the modified APP further comprise the following amino acid substitutions: G676R, F681Y and R684H.

In some embodiments, the modified APP comprises a Swedish double mutation. For example, the Swedish double mutation may comprise a K670N substitution and a M671L substitution. In some embodiments, the modified APP comprises a Beyreuther/Iberian mutation. For example, the Beyreuther/Iberian mutation may comprise a I716F substitution. In some embodiments, the modified APP comprises an Arctic mutation. For example, the Arctic mutation may comprise a E693G substitution.

In some embodiments, the rat or the living part thereof is homozygous or heterozygous for the chimeric APP gene.

In some embodiments, in the rat or the living part thereof, an expression level of full-length APP is not significantly different from that of a corresponding wildtype rat.

In some embodiments, in the rat or the living part thereof, an expression level of an APP fragment is not significantly different from that of a corresponding wildtype rat. For example, the APP fragment may comprises sAPP, CTF-α, CTF-β and/or AICD.

In some embodiments, the rat of the present disclosure (e.g., when heterozygous for the chimeric APP gene) shows Aβ oligomers at an age of 3 months or earlier.

In some embodiments, the rat of the present disclosure (e.g., when homozygous for the chimeric APP gene) shows Aβ oligomers at an age of 2 months or earlier.

In some embodiments, the rat of the present disclosure (e.g., when heterozygous for the chimeric APP gene) shows a Amyloid plaque at an age of 4 months or earlier.

In some embodiments, the rat of the present disclosure (e.g., when homozygous for the chimeric APP gene) shows a Amyloid plaque at an age of 2 months or earlier.

In some embodiments, no substantial accumulation of Aβ peptide occurs in the cerebellum of the rat of the present disclosure.

In some embodiments, hyper-phosphorylation of tau is detectable in the rat or the living part thereof according to the present disclosure. For example, the hyper-phosphorylation of tau may comprise or be revealed by increased phosphorylation of Thr231 and/or Ser202 of tau (e.g., in the rat's brain), comparing to that in a corresponding wildtype rat.

In some embodiments, oligomerization and/or aggregation of tau protein is detectable in said rat or the living part thereof. In some embodiments, said oligomerization and/or aggregation of tau protein is detectable with an anti-MC1 antibody.

In some embodiments, neuronal loss is detectable in the rat or the living part thereof according to the present disclosure. For example, the number of Neu-N positive neurons is decreased in said rat or the living part thereof, comparing to that in a corresponding wildtype rat. For example, such neuronal loss comprises apoptosis of a neuronal cell and/or necrosis of a neuronal cell (e.g., necroptosis). In some embodiments, the apoptosis is detectable by increased level of Bax, Bcl-2, Cl-caspase3, and/or Pro-caspase3 in the rat (e.g., in the rat brain) or the living part thereof comparing to that in a corresponding wildtype rat. In some embodiments, the necrosis (e.g., necroptosis) is detectable by increased level of RIPK1 and/or pMLKL in the rat (e.g., in the rat brain) or the living part thereof comparing to that in a corresponding wildtype rat. In some embodiments, RIPK3 level in the rat or the living part thereof is comparable to that in a corresponding wildtype rat. In some embodiments, a necrosome is detectable in said rat or the living part thereof.

In some embodiments, gliosis is detectable in the rat or the living part thereof according to the present disclosure. The gliosis may comprise microgliosis and/or astrocytosis. In some cases, the microgliosis and/or astrocytosis may be associated with Amyloid plaques.

In some embodiments, synaptic degeneration is detectable in the rat or the living part thereof according to the present disclosure. For example, the synaptic degeneration may be revealed by swelling and/or hollowing of postsynaptic density.

In some embodiments, a brain morphological and/or weight change is detectable in said rat or the living part thereof, comparing to that in a corresponding wildtype rat. In some embodiments, said brain morphological and/or weight change comprises a reduction of brain size, an appearance and/or enlarging of a ventricular cavity, and/or a damage in hippocampus.

In some embodiments, a brain cognitive impairment is detectable in said rat comparing to a corresponding wildtype rat. In some embodiments, said cognitive impairment is detected in an open field test, a Morris maze test and/or a T maze working memory test.

In some embodiments, the rat is a knock-in rat or is derived from a knock-in rat. In the rat, at least a part of an endogenous APP gene may be substituted by a heterologous nucleic acid sequence encoding at least a part of the modified APP. The at least part of the endogenous APP gene may comprise at least a part of exon 16 and at least a part of exon 17 of the endogenous APP gene. The heterologous nucleic acid sequence may comprise a mutated exon 16 and a mutated exon 17.

In some embodiments, the modified APP comprises an amino acid sequence as set forth in SEQ ID NO: 2.

In another aspect, the present disclosure provides a descendant of the rat of the present disclosure. The descendant may be obtained by crossing the rat of the present disclosure with a second rat, wherein said second rat may or may not comprise the chimeric APP gene encoding the modified APP as defined in the present disclosure. In some embodiments, the descendant comprises the chimeric APP gene encoding the modified APP as defined in the present disclosure.

In another aspect, the present disclosure provides a cell line or primary cell culture derived from the rat or living part thereof, or from the descendant according to the present disclosure.

In another aspect, the present disclosure provides a tissue derived from the rat or living part thereof, or from the descendant according to the present disclosure. The tissue may comprise a body fluid of the rat or of the descendant. For example, the body fluid may be selected from the group consisting of: blood, plasma (e.g., plasma comprising an exosome), serum, urine, sweat, tear, saliva, semen and cerebral spinal fluid.

In some embodiments, the tissue comprises a brain or a part thereof from said rat or said descendant. For example, the part of the brain may comprise a portion of the brain selected from the group consisting of: olfactory bulb, amygdaloid nucleus, basal ganglia, hippocampus, thalamus, hypothalamus, cerebral cortex, medulla oblongata and cerebellum.

In some embodiments, the tissue comprises olfactory mucosa of said rat or said descendant.

In some embodiments, the tissue comprises a part of central nervous system (such as the spinal cord or a part thereof), a part of peripheral nervous system, a skin tissue, a muscle tissue, and/or a visceral organ from the rat of the present disclosure or a descendant thereof.

In another aspect, the present disclosure provides a cell derived from the rat or living part thereof, or from the descendant according to the present disclosure.

In some embodiments, the cell comprises a cell selected from the group consisting of: a primary neuron, a microglia, an astrocyte, an oligodendrocyte, a macrophage, a perivascular epithelioid cell, a B cell, a T cell, a somatic stem cell, an NK cell, a totipotent stem cell, a unipotent stem cell, an embryonic stem cell, an induced pluripotent stem cell, and a gamete. The gamete may comprise a sperm, and/or an oocyte.

In some embodiments, the cell is not capable of developing into a complete rat. For example, the cell may not be a totipotent stem cell or an embryonic stem cell.

In some embodiments, the rat or the living part thereof, the descendant, the cell line or primary cell culture, the tissue, or the cell according to the present disclosure is used for screening for a substance, a device, a composition and/or a biomarker useful in the treatment, diagnosis, prevention, monitoring and/or prognosis of Alzheimer's disease.

In another aspect, the present disclosure provides a method of screening for a substance, a device, and/or a composition useful in the treatment, prevention and/or prognosis of Alzheimer's disease, comprising applying a candidate substance, device and/or composition to the rat or living part thereof, the descendant, the cell line or primary cell culture, the tissue, and/or the cell according to the present disclosure, and determining an effect of the candidate substance, device and/or composition on one or more of the following: 1) an expression and/or accumulation of Aβ in the rat or living part thereof, the descendant, the cell line or primary cell culture, the tissue and/or the cell; 2) an expression and/or accumulation of an APP fragment (e.g., sAPP, CTF-β, CTF-a and/or AICD) in the rat or living part thereof, the descendant, the cell line or primary cell culture, the tissue and/or the cell; 3) phosphorylation of tau protein in the rat or living part thereof, the descendant, the cell line or primary cell culture, the tissue and/or the cell; 4) an oligomerization and/or aggregation of tau protein in the rat or living part thereof, the descendant, the cell line or primary cell culture, the tissue and/or the cell; 5) brain morphology and/or brain weight in the rat or living part thereof, the descendant, the cell line or primary cell culture, the tissue and/or the cell; 6) brain neurofibrillary tangle formation in the rat or living part thereof, the descendant, the cell line or primary cell culture, the tissue and/or the cell; 7) a learning function, a memory function, a cognitive function, a sensory function, a motor function, an emotional function and/or a synaptic function of the rat or the descendant thereof; 8) brain lesion of the rat or living part thereof, the descendant and/or the tissue thereof; 9) neuronal loss, necrosome formation, neuronal death, neuronal apoptosis, neuronal necrosis, neuronal necroptosis, Neu-N positive neuron number and/or neurodegeneration in the rat or living part thereof, the descendant, the cell line or primary cell culture, the tissue and/or the cell; 10) gliosis, microglia activation, astrocyte activation, and/or inflammatory reaction in the rat or living part thereof, the descendant, the cell line or primary cell culture, the tissue and/or the cell; 11) oxidative stress and/or mitochondria dysfunction in the rat or living part thereof, the descendant, the cell line or primary cell culture, the tissue and/or the cell; 12) vascular dysfunction in the rat or living part thereof, the descendant, the cell line or primary cell culture, the tissue and/or the cell; 13) defeat of misfolded protein degradation, and/or autophage in the rat or living part thereof, the descendant, the cell line or primary cell culture, the tissue and/or the cell; and 14) brain glucose and/or lipid metabolism in the rat or living part thereof, the descendant and/or the tissue.

The method of screening may be an in vitro method, an ex vivo method, or an in vivo method.

In some embodiments, the accumulation of Aβ comprises Aβ oligomerization and/or Amyloid plaque formation.

In some embodiments, the synaptic function comprises synaptic transmission, synaptic plasticity, synaptic protein formation and/or function, and/or synaptic morphology.

In some embodiments, the inflammatory reaction comprises a reaction through an innate immune cell. The innate immune cell may comprise a T cell, a B cell, an NK cell, a microphage, and/or a dendritic cell.

In some embodiments, the vascular dysfunction includes amyloid angiopathy and/or disruption of blood-brain barrier (BBB).

In another aspect, the present disclosure provides a use of the rat or the living part thereof, the descendant, the cell line or primary cell culture, the tissue, and/or the cell according to the present disclosure in the preparation of a system of screening for a substance, a device, a composition and/or a biomarker useful in the treatment, diagnosis, prevention, monitoring and/or prognosis of Alzheimer's disease.

In the present disclosure, the device may comprise a medical device, such as a medical device alleged to be effective in the treatment, diagnosis, prevention, monitoring and/or prognosis of Alzheimer's disease.

In the present disclosure, the composition may comprise a mixture derived from one or more organisms. The organism may be a plant, an animal and/or a microorganism. For example, the composition may comprise a tissue homogenate and/or a blood sample. In some embodiments, the composition comprises extracts from one or more plants. For example, the composition may comprise a candidate traditional Chinese medicine.

In another aspect, the present disclosure provides a method of screening for a biomarker useful in the diagnosis and/or monitoring of Alzheimer's disease. The method may comprise determining a presence and/or a level of a substance in a sample obtained from the rat or living part thereof or from the descendant according to the present disclosure, before and after detection of an indication of the Alzheimer's disease, and identifying a substance showing a change of the presence and/or level before and after the detection.

In another aspect, the present disclosure provides a method for generating the rat or the living part thereof according to the present disclosure. The method may comprise knocking-in a heterologous nucleic acid sequence into an endogenous APP gene locus of a rat. The knocking-in may substitute at least a part of an endogenous APP gene with a heterologous nucleic acid sequence encoding at least a part of the modified APP. The at least part of the endogenous APP gene may comprise at least a part of exon 16 and at least a part of exon 17 of the endogenous APP gene.

In some embodiments, the heterologous nucleic acid sequence comprises a mutated exon 16 and a mutated exon 17 of the wildtype rat APP gene. Mutations in the mutated exon 16 and mutated exon 17 may introduce multiple amino acid substitutions in their encoded polypeptides (e.g., the protein product they encode), and the multiple amino acid substitutions may comprise an amino acid substitution at the following residues: K670, M671, I716 and E693. For example, the multiple amino acid substitutions may comprise an amino acid substitution of K670, an amino acid substitution of M671, an amino acid substitution of I716 and an amino acid substitution of E693. The multiple amino acid substitutions may further comprise the following amino acid substitutions: G676R, F681Y and R684H. In some embodiments, the multiple amino acid substitutions comprise the substitution K670N, M671L, I716F, and/or E693G.

In some embodiments of the method, the knocking-in comprises contacting the genome of a stem cell or a zygote of a rat with the following in the presence of a donor nucleic acid molecule comprising the heterologous nucleic acid sequence: 1) a CRISPR associated (Cas) protein; and 2) one or more ribonucleic acid (RNA) sequences that comprise: i) a portion complementary to a portion of the endogenous APP gene upstream of exon 16; ii) a portion complementary to a portion of the endogenous APP gene downstream of exon 17; and iii) a binding site for the Cas protein.

In some embodiments of the method, the knocking-in further comprises maintaining the cell or zygote under conditions in which the one or more RNA sequences hybridize to the portion of the endogenous APP gene upstream of exon 16 and the portion of the endogenous APP gene downstream of exon 17, and the Cas protein cleaves the endogenous APP gene nucleic acid sequence upon the hybridization of the one or more RNA sequences.

In some embodiments of the method, the Cas protein is Cas9.

In some embodiments of the method, the stem cell is selected from the group consisting of: an embryonic stem cell, a somatic stem cell, a totipotent stem cell, a unipotent stem cell and an induced pluripotent stem cell.

In some embodiments of the method, the binding site for the Cas protein comprises a tracrRNA sequence.

In some embodiments of the method, the Cas protein is introduced into the cell or zygote of the rat in the form of a protein, a messenger RNA(mRNA) encoding the Cas protein, or a DNA encoding the Cas protein.

In some embodiments of the method, the one or more RNA sequences are introduced into the cell or zygote in the form of one or more RNA molecules or one or more DNA molecules encoding the RNA sequences.

In some embodiments of the method, the portion complementary to a portion of the endogenous APP gene upstream of exon 16 or the portion complementary to a portion of the endogenous APP gene downstream of exon 17 is encoded by a nucleic acid molecule comprising a sequence as set forth in any one of SEQ ID NOs: 3-12.

In some embodiments of the method, the portion complementary to a portion of the endogenous APP gene upstream of exon 16 is encoded by a nucleic acid molecule comprising a sequence as set forth in SEQ ID NO: 3.

In some embodiments of the method, the portion complementary to a portion of the endogenous APP gene downstream of exon 17 is encoded by a nucleic acid molecule comprising a sequence as set forth in SEQ ID NO: 4.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments and its several details are capable of modifications in various obvious respects, all without departing from the disclosure. Accordingly, the drawings and description are to be regarded as illustrative in nature and not as restrictive.

INCORPORATION BY REFERENCE

All publications, patents and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are employed and the accompanying drawings (also "figure" and "FIG." herein), of which:

FIGS. 6A-6B illustrate results of genotype identification in F0 rats.

FIG. 48A-48B illustrate RIPK3 and Iba1 colocalization in the brain of 6-month old wildtype rats and 6-month old rats of the present disclosure.

DETAILED DESCRIPTION

Figure 1:
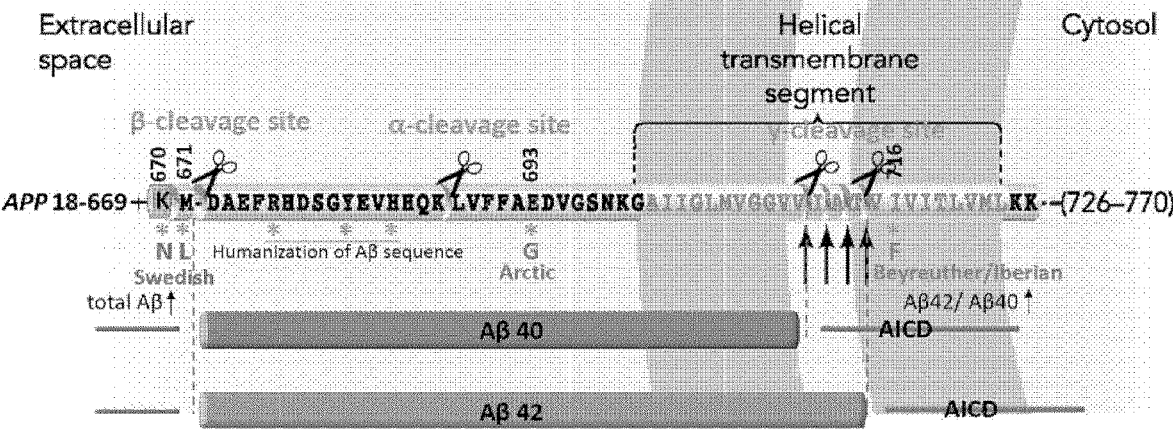
FIG. 1 illustrates the mutations comprised in a modified APP of the present disclosure; see SEQ ID NO: 14.

While various embodiments of the invention have been shown and described herein, it will be obvious to those skilled in the art that such embodiments are provided by way of example only. Numerous variations, changes and substitutions may occur to those skilled in the art without departing from the invention. It should be understood that various alternatives to the embodiments of the invention described herein may be employed.

As used herein, the term "living part" generally refers to a part of an organism (e.g., a rat) that stably carries at least a part of the genetic information (e.g., DNA or a part thereof) of said organism. For example, a "living part" of the rat according to the present application may stably carry the chimeric APP gene encoding the modified APP, as defined in the present application. In some cases, the living part may comprise an organ, a tissue and/or a cell.

As used herein, the term "CRISPR" generally refers to refers to Clustered Regularly Interspaced Short Palindromic Repeats. The CRISPR loci usually differs from other SSRs by the structure of the repeats, which have been termed short regularly spaced repeats (SRSRs). Generally, the repeats are short elements that appear in regularly spaced clusters with unique intervening sequences of a substantially constant length. The repeat sequences are highly conserved between strains, but the number of interspersed repeats and the sequences of the spacer regions usually differ from strain to strain.

As used herein, the terms "sgRNA", "guide RNA", "single guide RNA" and "synthetic guide RNA" are interchangeable and generally refer to the polynucleotide sequence comprising the guide sequence. The guide sequence is about 20 bp and is within the guide RNA that specifies the target site.

As used herein, the term "heterologous nucleic acid sequence" generally refers to a nucleic acid sequence derived from a foreign source and/or present in a non-endogenous form. For example, a heterologous nucleic acid sequence may originate from a foreign subject, may originate from a foreign species, may be artificially synthesized, may be positioned in a foreign locus and/or may be substantially modified.

As used herein, the term "homologous recombination" generally refers to a type of genetic recombination in which nucleotide sequences are exchanged between two similar or identical molecules of DNA known as homologous sequences or homologous arms.

As used herein, the term "endogenous APP gene" generally refers to an endogenous DNA fragment (such as an endogenous rat DNA fragment) encoding for an amyloid precursor protein or a fragment thereof.

As used herein, the term "CRISPR associated protein 9" or "Cas9" protein generally refers to an RNA-guided DNA endonuclease associated with the CRISPR (Clustered Regularly Interspaced Short Palindromic Repeats) type II adaptive immunity system found in certain bacteria, such as Streptococcus pyogenes and other bacteria. For example, a Cas9 protein may comprise not only the wildtype Cas9 found in Streptococcus pyogenes, but also its various variants, such as those described in WO2013/176772A1. In some embodiments, a Cas9 protein may comprise a Cas9 sequence from S. pyogenes, N. meningitidis, S. thermophilus and T. denticola, as described in Esvelt et al., Nature Methods, 10(11): 1116-1121, 2013.

As used herein, the term "Cas9 coding sequence" generally refers to a polynucleotide sequence capable of being transcribed and/or translated, according to a genetic code functional in a host cell/host animal, to produce a Cas9 protein. The Cas9 coding sequence may be a DNA (such as a plasmid) or an RNA (such as an mRNA).

As used herein, the term "Cas9 riboprotein" generally refers to a protein/RNA complex consisting of Cas9 protein and an associated guide RNA.

As used herein, the term "CRISPR/Cas9 system" generally refers to a tool for site-specific genomic targeting in an organism. For example, it may be a type II CRISPR/Cas system, which is a prokaryotic adaptive immune response system that uses non-coding RNAs to guide the Cas9 nuclease to induce site-specific DNA cleavage. This DNA damage is repaired by cellular DNA repair mechanisms, either via the non-homologous end joining DNA repair pathway (NHEJ) or the homology directed repair (HDR) pathway. The CRISPR/Cas9 system may be harnessed to create a simple, RNA-programmable method to mediate genome editing in mammalian cells and may be used to generate gene knockouts (via insertion/deletion) or knock-ins (via HDR).

As used herein, the term "knocking-in" or "knock in" generally refers to a genetic engineering process that involves the one-for-one substitution of DNA sequence information in a genetic locus or the insertion of sequence information not found within the endogenous locus. Knocking-in may involve a gene inserted into a specific locus and may thus be a "targeted" insertion.

As used herein, the term "vector" generally refers to a DNA molecule used as a vehicle to artificially carry foreign genetic material into another cell or host, where it can be replicated and/or expressed.

As used herein, the term "targeting vector" generally refers to a vector carrying a targeting sequence to be inserted or incorporated into a host genome and/or for substituting an endogenous DNA fragment.

As used herein, the term "embryonic stem cell" or "ES cell" generally refers to a pluripotent stem cell derived from the inner cell mass (ICM) of a blastocyst (an early-stage preimplantation embryo of a mammal), that can be cultured after an extended period in vitro, before it is inserted/injected into the cavity of a normal blastocyst and be induced to resume a normal program of embryonic development to differentiate into various cell types of an adult mammal, including germ cells.

As used herein, the term "zygote" generally refers to a eukaryotic cell formed by a fertilization event between two gametes, e.g., an egg and a sperm from a mammal.

As used herein, the term "zygosity" generally refers to the degree of similarity of the alleles for a trait in an organism.

As used herein, the term "homozygote" or "homozygous" is used with respect to a particular gene or DNA (e.g., a heterologous nucleic acid sequence that has been knocked-in) and refers to a diploid cell or organism in which both homologous chromosomes have the same alleles or copies of the gene/DNA.

As used herein, the term "heterozygote" or "heterozygous" is used with respect to a particular gene or DNA (e.g., a heterologous nucleic acid sequence that has been knocked-in) and refers to a diploid cell or organism in which the two homologous chromosomes have different alleles/copies/versions of the gene or DNA.

As used herein, the term "chimeric APP gene" generally refers to a DNA fragment encoding an amyloid precursor protein or a fragment thereof and at least a part of the DNA fragment is not from the endogenous APP gene. For example, a chimeric APP gene may comprise a heterologous nucleic acid sequence substituting a part of the endogenous APP gene.

As used herein, the term "modified APP" generally refers to an amyloid precursor protein that has an addition, a deletion and/or a substitution of at least one amino acid residue.

As used herein, the term "Swedish double mutation" or "Swedish mutation" generally refers to a double mutation in the APP gene originally found in a Swedish family, which is located before the amyloid β-peptide (Aβ) region of APP and results in an increased production and secretion of Aβ, as described in Nat Genet. 1992 August; 1(5):345-7. The Swedish double mutation is located in exon 16 of the human APP gene and is the only known mutation immediately adjacent to the β-secretase site in APP. In some cases, the Swedish mutation results in a substitution of two amino acids, lysine (K) 670 and methionine (M) 671. The Swedish double mutation has been shown to increase total Aβ levels. Specifically, there is increased production and secretion of Aβ40 and Aβ42, but the ratio of Aβ40/Aβ42 is generally not affected. In some embodiments, the Swedish double mutation comprises the amino acid substitutions K670N and M671L.

As used herein, the term "Beyreuther/Iberian mutation" generally refers to a mutation in the APP gene (e.g., at residue I716) that affects APP cleavage by γ-secretase. Specifically, the Beyreuther/Iberian mutation is located in exon 17 of the human APP gene and may affect γ-secretase cleavage specificity and cause a dramatic increase in the Aβ42/Aβ40 ratio. In some embodiments, the Beyreuther/Iberian mutation comprises the amino acid substitution I716F.

As used herein, the term "Arctic mutation" generally refers to a mutation in the APP gene (e.g., at residue E693) that leads to an increased propensity and faster rate of Aβ40 protofibril formation. It is also known as "E22G", because it affects the twenty-second amino acid of Aβ peptides. The Arctic mutation was one of several pathogenic APP mutations found to confer resistance to neprilysin-catalyzed proteolysis of Aβ40. The Arctic mutation is located in exon 17 of the human APP gene. In some embodiments, the Arctic mutation comprises the amino acid substitution E693G.

As used herein, the term "not significantly different" generally refers to that the difference between two values or two objects are not substantial. For example, when two values are compared, a difference of less than about 10%, such as less than about 9%, less than about 8%, less than about 7%, less than about 6%, less than about 5.5%, less than about 5%, less than about 4.5%, less than about 4%, less than about 3.5%, less than about 3%, less than about 2.5%, less than about 2%, less than about 1.5%, less than about 1% or even less may be regarded as not significant different.

As used herein, the term "Aβ oligomers" generally refers to soluble amyloid β (Aβ) peptide aggregates, which normally form small clumps. An Aβ oligomer may be a dimer, a trimer, or other multimers of the Aβ peptide.

As used herein, the term "Aβ plaque" or "Amyloid plaque" generally refers to fibrillar aggregates of Aβ peptides (e.g., Aβ42 and/or Aβ40), wherein many copies of the Aβ peptides stick together to form fibrils or fibrous deposits (e.g., plaques).

As used herein, the term "substantial accumulation of Aβ peptide" generally refers to that formation of Aβ oligomers or Amyloid plaques may be detected using commonly employed detection methods or tools, such as specific Aβ antibody staining.

As used herein, the term "Aβ" or "Amyloid-β" generally refers to Amyloid-β peptides produced from the regulated intramembrane proteolysis of the amyloid precursor protein (APP). Sequential proteolytic cleavage events by β- and γ-secretase generate Aβ peptides of varying lengths, including Aβ40 and Aβ42. Its two extra hydrophobic residues give Aβ42 a higher propensity to aggregate into soluble oligomers and insoluble deposits than Aβ40 or the range of shorter peptides that have been observed in recent years by mass spectrometry analysis of cerebral spinal fluid (CSF). Multiple aggregated forms of Aβ exist, from dimers to β-pleated sheet fibrils in compact neuritic plaques. Excess amounts of Aβ can induce a variety of pathologic processes. Aβ can impair neuronal and glial function, synaptic physiology, neurotransmission and cognition. Evidence points to trans-cellular spread and templated seeding and the resulting deposition of aggregated Aβ into extraneuronal amyloid plaques is a pathological hallmark of AD.

As used herein, the term "humanized Aβ" and "human Aβ" may be used interchangeably, and generally refers to an Aβ peptide that comprises or has been modified to comprise substantially the same amino acid sequence as that of a wildtype human Aβ peptide.

As used herein, the term "hyper-phosphorylated" or "hyper-phosphorylation" refers to a state of being abnormally phosphorylated at one or more additional sites. For example, phosphorylation of the protein tau was found to negatively regulate its activity in promoting microtubule assembly, and abnormally hyperphosphorylated tau has been considered to be the major component of PHFs in AD. Normal brain tau contains 2-3 moles of phosphate per mole tau. Studies on human brain biopsy tissue indicated that several serine and threonine residues of tau are normally phosphorylated at low substoichiometrical levels. The phosphorylation level of tau isolated from autopsied AD brain is 3- to 4-fold higher than that of normal human brains. Tau phosphorylation at different sites has a different impact on its biological function and on its pathogenic role. Studies of the binding between hyperphosphorylated tau and normal tau suggest that Ser199/Ser202/Thr205, Thr212, Thr231/Ser235, Ser262/Ser356, and Ser422 are among the critical phosphorylation sites that convert tau to an inhibitory molecule that sequesters normal microtubule-associated proteins from microtubules.

As used herein, the term "neuronal loss" generally refers to a reduction in the amount or function of neuron cells in an organism. Neuronal loss may be revealed as death of neuron cells.

As used herein, the term "tau protein" generally refers to microtubule-associated protein tau (MAPT) that stabilizes microtubules. The tau protein is abundant in neurons of the central nervous system and is less common elsewhere, but is also expressed at very low levels in CNS astrocytes and oligodendrocytes. The tau protein may have two ways of controlling microtubule stability: isoforms and phosphorylation. For example, the accession ID of NCBI of *Homo sapiens* tau isoform 1 is NP_058519.3. AD may be associated with the tau protein that has become defective and no longer stabilize microtubules properly.

As used herein, the term "Neu-N" generally refers to Fox-3, Rbfox3, or Hexaribonucleotide Binding Protein-3, which is a neuronal nuclear antigen that is commonly used as a biomarker for neurons. In some embodiment, the vast majority of neurons may be strongly Neu-N positive, and Neu-N immunoreactivity can be widely used to identify neurons in tissue culture and in sections and to measure the neuron/glia ratio in brain regions.

As used herein, the term "necrosome" generally refers to a programmed form of necrosis, or inflammatory cell death. For example, the necrosis may be associated with unprogrammed cell death resulting from cellular damage, in contrast to orderly, programmed cell death via apoptosis.

As used herein, the term "morphological changes" generally refers to changes of the form and structure of organisms and their specific structural features. For example, the morphological changes may comprise the changes in external morphology (e.g. shape, structure, color, pattern, size) and internal morphology (e.g. the form and structure of the internal parts).

As used herein, the term "ventricular cavity" generally refers to a large chamber toward the bottom of the heart that collect and expel blood received from an atrium towards the peripheral beds within the body and lungs.

As used herein, the term "hippocampus" generally refers to a major component of the brains located in the medial temporal lobe of the brain. In Alzheimer's disease, the hippocampus may be one of the first regions of the brain to suffer damage; short-term memory loss and disorientation are included among the early symptoms.

As used herein, the term "AD" generally refers to Alzheimer's disease, a chronic neurodegenerative disease that usually starts slowly and gradually worsens over time. For example, eight intellectual domains are most commonly impaired in AD-memory, language, perceptual skills, attention, motor skills, orientation, problem solving and executive functional abilities. These domains are equivalent to the NINCDS-ADRDA Alzheimer's Criteria as listed in the Diagnostic and Statistical Manual of Mental Disorders (DSM-IV-TR) published by the American Psychiatric Association.

As used herein, the term "cognitive impairment" generally refers to damages of cognition of patients suffering from AD. For example, the cognitive impairment may comprise an impairment of a learning function, a memory function, a cognitive function, a sensory function, a motor function and/or an emotional function.

As used herein, the term "apoptosis" generally refers to a genetically directed process of cell self-destruction that is marked by the fragmentation of nuclear DNA, which may be activated either by the presence of a stimulus or removal of a suppressing agent or stimulus. Apoptosis is also known as cell suicide, programmed cell death. Bcl-2 Family Proteins are among the main intracellular regulators of apoptosis. The Bcl-2 family of intracellular proteins helps regulate the activation of procaspases. Some members of the Bcl-2 family promote procaspase activation and cell death. For example, the apoptosis promoter Bad functions by binding to and inactivating the death-inhibiting members of the family, whereas others, like Bax and Bak, stimulate the release of cytochrome c from mitochondria. Bax and Bak are themselves activated by other apoptosis-promoting members of the Bcl-2 family such as Bid. Caspase-3 is a caspase protein that interacts with caspase-8 and caspase-9. It is encoded by the CASP3 gene. Sequential activation of caspases plays a central role in the execution-phase of cell apoptosis. Caspases exist as inactive proenzymes that undergo proteolytic processing at conserved aspartic residues to produce two subunits, large and small, that dimerize to form the active enzyme. Caspase-3 is the predominant caspase involved in the cleavage of amyloid-beta 4A precursor protein (also known as APP), which is associated with neuronal death in Alzheimer's disease. Increased level of procaspase 3 ("Pro-caspase3") and its cleaved form ("Cl-caspase3") is often associated with increased apoptosis.

As used herein, the term "necrosis" generally refers to a form of cell injury which results in the premature death of cells in living tissue by autolysis. The signaling pathway responsible for carrying out necrosis or necroptosis is generally understood. Production of TNFα during viral infection leads to stimulation of its receptor TNFR1. The TNFR-associated death protein TRADD signals to RIPK1 which recruits RIPK3 forming the necrosome. Phosphorylation of MLKL ("pMLKL") by the ripoptosome drives oligomerization of MLKL, allowing MLKL to insert into and permeabilize plasma membranes and organelles. Integration of MLKL leads to the inflammatory phenotype and release of damage-associated molecular patterns (DAMPs), which elicit immune responses. Specifically, necroptosis, a programmed form of necrosis, is executed by the mixed lineage kinase domain-like (MLKL) protein, which is triggered by receptor-interactive protein kinases (RIPK) 1 and 3. It has been found that necroptosis was activated in postmortem human AD brains, positively correlated with Braak stage, and inversely correlated with brain weight and cognitive scores. In addition, it has been found that the set of genes regulated by RIPK1 overlapped significantly with multiple independent AD transcriptomic signatures, indicating that RIPK1 activity could explain a substantial portion of transcriptomic changes in AD.

As used herein, the term "gliosis" generally refers to a fibrous proliferation of glial cells in injured areas of the central nervous system (CNS). Gliosis is prevalent in glioma as well as in many other neurological disorders, such as Alzheimer's disease, and may be detected by elevated glial fibrillary acidic protein (GFAP) levels in postmortem tissue samples using immunohistochemistry. Normally, gliosis is a combination of astrocytosis and microgliosis.

As used herein, the term "synaptic degeneration" generally refers to loss or dysfunction of synapses, it may be reflected by the state/expression of synaptic marker and/or postsynaptic densities. The postsynaptic density (PSD) is a protein dense specialization attached to the postsynaptic membrane. PSDs were originally identified by electron microscopy as an electron-dense region at the membrane of a postsynaptic neuron. The PSD is in close apposition to the presynaptic active zone and ensures that receptors are in close proximity to presynaptic neurotransmitter release sites. For example, hollowing or swelling of PSDs may indicate synaptic degeneration. Synaptic state may be detected by examining the expression or level of Synaptophysin. Synaptophysin has been reported to be an integral membrane glycoprotein found in many types of active neurons, and has been found in the membrane after stimulation of the neurons.

As used herein, the term "donor nucleic acid molecule" generally refers to a nucleic acid molecule that provides a heterologous nucleic acid sequence to a recipient (e.g., a receiving nucleic acid molecule).

As used herein, the term "upstream", when used with DNA, RNA or gene sequences, generally refers to a relative position in a DNA, RNA or gene sequence toward the 5' end. When considering double-stranded DNA, upstream is toward the 5' end of the coding strand for the gene in question.

As used herein, the term "downstream", when used with DNA, RNA or gene sequences, generally refers to a relative position in a DNA, RNA or gene sequence toward the 3' end. When considering double-stranded DNA, downstream is toward the 3' end of the coding strand for the gene in question.

As used herein, the term "hybridize to" or "hybridization", when used in the context of molecular biology, generally refers to a process in which single-stranded deoxyribonucleic acid (DNA) or ribonucleic acid (RNA) molecules anneal to complementary DNA or RNA.

As used herein, the term "induced pluripotent stem cell" or "iPS cell" generally refers to a cell taken from any tissue (usually skin or blood) from a child or adult and is genetically modified to behave like an embryonic stem cell. As the name implies, these cells are pluripotent, which means that they have the ability to form most, if not all, adult cell types.

As used herein, the term "tracrRNA" generally refers to trans-activating crRNA (tracrRNA), which is a small trans-encoded RNA. TracrRNA is complementary to and base pairs with a pre-crRNA forming an RNA duplex. This is cleaved by RNase III, an RNA-specific ribonuclease, to form a crRNA/tracrRNA hybrid. This hybrid acts as a guide for the endonuclease Cas9, which cleaves the invading nucleic acid.

Alzheimer's Disease Animal Model

In one aspect, the present disclosure provides a rat or a living part thereof, comprising a chimeric APP gene encoding a modified APP. Comparing to a wildtype rat APP as set forth in SEQ ID NO:1, the modified APP may comprise an amino acid substitution at one or more positions selected from the group consisting of: K670, M671, I716 and E693. In some embodiments, the modified APP may further comprise an amino acid substitution at the following residues: K670, M671, I716 and E693. For example, the multiple amino acid substitutions may comprise an amino acid substitution of K670, an amino acid substitution of M671, an amino acid substitution of I716, and an amino acid substitution of E693.

The multiple amino acid substitutions may further comprise the following amino acid substitutions: G676R, F681Y and R684H. Thus, in some embodiments, the multiple amino acid substitutions may comprise the substitutions G676R, F681Y, R684H, an amino acid substitution of K670, an amino acid substitution of M671, an amino acid substitution of I716, and an amino acid substitution of E693.

In the present disclosure, when referring to an amino acid substitution, "XnY" means that the amino acid X at residue n is substituted by the amino acid Y.

In some embodiments, the modified APP may comprise a Swedish double mutation. For example, the Swedish double mutation may comprise a K670N substitution and a M671L substitution. In some embodiments, the modified APP may comprise a Beyreuther/Iberian mutation. For example, the Beyreuther/Iberian mutation may comprise a I716F substitution. In some embodiments, the modified APP may comprise an Arctic mutation. For example, the Arctic mutation may comprise an E693G substitution. In some embodiments, the modified APP may comprise the Swedish double mutation, the Beyreuther/Iberian mutation and the Arctic mutation. For example. the modified APP may comprise the following amino acid substitutions: K670N, M671L, I716F and E693G. In some embodiments, comparing to a wildtype rat APP as set forth in SEQ ID NO:1, the modified APP may comprise multiple amino acid substitutions, and the multiple amino acid substitutions comprise the following amino acid substitutions: K670N, M671L, I716F, E693G, G676R, F681Y and R684H.

The chimeric APP gene in the rat may be homozygous or heterozygous. In some embodiments, the rat or the living part thereof may be heterozygous for the chimeric APP gene. For example, the rat or the living part thereof may comprise one copy of the endogenous APP gene and one copy of the chimeric APP gene. In some embodiments, the rat or the living part thereof may be homozygous for the chimeric APP gene. For example, the rat or the living part thereof may comprise two copies of the chimeric APP gene.

The chimeric APP gene comprised in the rat of the present invention may produce a humanized Aβ peptide. For example, to generate a humanized Aβ peptide, the 5th amino acid G of the rat endogenous Aβ (676th amino acid in case of APP) may be substituted by a R, the 10th amino acid F of the rat endogenous Aβ (681st amino acid in case of APP) may be substituted by a Y and the 13th amino acid R of the rat endogenous Aβ (684th amino acid in case of APP) may be substituted by a H.

The chimeric APP gene encoding the modified APP may be stably incorporated in the genome of the rat or a living part thereof. For example, the heterologous nucleic acid sequence encoding the modified APP may be permanently present in a cell of the rat in a state enabling the transcription and translation of the modified APP. The heterologous nucleic acid sequence may be incorporated in a chromosome of the host (e.g., the rat or a cell thereof).

The rat of the present disclosure may be generated by introducing a heterologous nucleic acid sequence encoding the modified APP into, for example, a fertilized egg, an unfertilized egg, a spermatozoon, a primordial germ cell, an oogonium, an oocyte, a spermatogonium, a spermatocyte and/or a sperm cell of the rat, for example, at an initial stage in the embryonic development of the fertilized egg (e.g., before 8-cell stage). The heterologous nucleic acid sequence may be introduced by a gene transfer method, such as calcium phosphate co-precipitation, electroporation, lipofection, agglutination, microinjection, gene gun (particle gun) and/or DEAE-dextran method. The heterologous nucleic acid sequence may also be introduced into a somatic cell, a tissue and/or an organ of the rat (e.g., by a gene transfer method) and then, the engineered somatic cell, tissue and/or organ may be further cultured and/or maintained. The engineered cells may also be fused with an embryo or another cell (such as a cell from the germline of the rat) by cell fusion methods to produce a rat of the present disclosure.

In some cases, a rat according to the present disclosure may be obtained by: introducing a heterologous nucleic acid sequence encoding the modified APP into an embryonic stem cell (ES cell) or an iPS cell of a rat (e.g., by a gene transfer method); selecting a clone in which the nucleic acid sequence is stably incorporated; producing a chimeric rat by injecting the ES cell or iPS cell into a blastocyst or aggregation of ES cell/iPS cluster and 8-cell embryo; and selecting an embryo having the heterologous nucleic acid sequence introduced in its cell line.

In some embodiments, the rat according to the present disclosure may be a knock-in (KI) rat, wherein the endogenous APP gene is at least partially substituted by a heterologous nucleic acid sequence encoding a modified APP, as described in the present disclosure. For example, the rat according to the present disclosure may be generated by introducing the heterologous nucleic acid sequence into an ES cell or iPS cell by a suitable targeting vector and substituting the endogenous APP gene or at least a part thereof with the heterologous nucleic acid sequence or at least a part thereof, for example, by homologous recombination.

In the rat or the living part thereof according to the present disclosure, an expression level of full-length APP may not be significantly different from that of the corresponding wild-type rat. For example, as revealed by immunostaining with anti-APP antibodies, such as an anti-APP C-terminal antibody (e.g., A8717), or an anti-human Aβ antibody (e.g., the antibody 6E10).

In the rat or the living part thereof, an expression level of APP-derived fragments (or APP fragments, such as sAPP, CTF-α, CTF-β and/or AICD) may not be significantly different from that of the corresponding wildtype rat. For example, as revealed by immunostaining with appropriate antibodies, such as the anti-APP-CTF antibody (e.g., Sigma, A8717) or the anti-APP N terminus antibody (e.g., Millipore, 22C11).

The rat of the present disclosure may show Aβ oligomers at an age of 4 months or earlier (e.g., at an age of 3.5 months or earlier, at an age of 3 months or earlier, at an age of 2.5 months or earlier, at an age of 2 months or earlier, or at an age of 1 month or earlier). For example, in a rat of the present disclosure that is heterozygous for the chimeric APP gene, Aβ oligomers may be detected at an age of 3 months or earlier (e.g., at an age of 2.5 months or earlier, at an age of 2 months or earlier, at an age of 1.5 months or earlier, or at an age of 1 month or earlier). In some cases, Aβ oligomers can be detected at an age as early as 1 month-old or even earlier in a rat of the present disclosure that is heterozygous for the chimeric APP gene. In another example, in a rat of the present disclosure that is homozygous for the chimeric APP gene, Aβ oligomers may be detected at an age of 2-month or earlier (e.g., at an age of 1.5 months or earlier, or at an age of 1 month or earlier). For example, said Aβ oligomers may be revealed by immunostaining with an anti-β-Amyloid antibody (e.g., Cell Signaling Technology, 2454), and/or anti-β-Amyloid oligomer antibody (OMAB) (e.g., Agrisera, AS10932). In some cases, Aβ oligomers can be detected in a rat of the present disclosure homozygous for the chimeric APP gene at an age of 1 month or earlier.

The rat of the present disclosure may show a Amyloid plaque at an age of 5 months or earlier (e.g., at an age of 4.5 months or earlier, at an age of 4 months or earlier, at an age of 3.5 months or earlier, at an age of 3 months or earlier, at an age of 2.5 months or earlier, at an age of 2 months or earlier, at an age of 1.5 months or earlier, or at an age of 1 month or earlier). For example, in a rat of the present disclosure that is heterozygous for the chimeric APP gene, a Amyloid plaque may be detected at an age of 5 months or earlier (e.g., at an age of 4.5 months or earlier, at an age of 4 months or earlier, at an age of 3.5 months or earlier, at an age of 3 months or earlier, at an age of 2.5 months or earlier, at an age of 2 months or earlier, or at an age of 1 month or earlier). In a rat of the present disclosure that is homozygous for the chimeric APP gene, a Amyloid plaque may be detected at an age of 1 month or earlier In addition, in a rat of the present disclosure that is heterozygous for the chimeric APP gene, Aβ plaques may still be detected at an age of 12 months or above, at an age of 24 months or above, or at an age of 36 months or above. As another example, in a rat of the present disclosure that is homozygous for the chimeric APP gene, a Amyloid plaque may be detected at an age of 3 months or earlier (e.g., at an age of 2.8 months or earlier, at an age of 2.5 months or earlier, at an age of 2 months or earlier, at an age of 1.5 months or earlier, or at an age of 1 month or earlier). In some cases, an Amyloid plaque may occur at an age of as early as 1 month-old or earlier in a rat of the present disclosure, for example when the rat is homozygous for the chimeric APP gene. In addition, in a rat of the present disclosure that is homozygous for the chimeric APP gene, Aβ plaques may still be detected at an age of 6 months or above, at an age of 12 months or above, at an age of 22 months or above, or at an age of 24 months or above. In some cases, thickness and/or density of the Aβ plaques in the rat of the present disclosure (e.g., the rats homozygous for the chimeric APP gene) may vary along with the age of the rats. For example, when the rats get older, the Aβ plaques may become thinner and/or denser. In some embodiments, the Aβ plaques detected in a 22-month old rat of the present disclosure (a rat homozygous for the chimeric APP gene of the present disclosure) is thinner and/or denser than that detected in a 12-month old rat of the present disclosure. In another example, the Aβ plaques detected in a 6-month old rat of the present disclosure (a rat homozygous for the chimeric APP gene of the present disclosure) is thinner and/or denser than that detected in a 3-month old, 2-month old or 1-month old rat of the present disclosure.

The Amyloid plaque may be revealed by immunostaining with an anti-β-Amyloid antibody (e.g., Cell Signaling Technology, 2454), and/or anti-β-Amyloid oligomer antibody (OMAB) (e.g., Agrisera, AS10932).

Further, in a rat of the present disclosure (e.g., homozygous for the chimeric APP gene), distribution of Aβ plaques in the cortex, hippocampus and/or subcortical regions may be similar to that of an AD human patient.

In some embodiments, no substantial accumulation of Aβ peptide may be observed in the cerebellum of the rat of the present disclosure. This is an unexpected huge advantage comparing to the phenotypes observed in other AD model animals and it more closely resembles the situations observed in human patients.

In some embodiments, hyper-phosphorylation of tau may be detectable in the rat or the living part thereof according to the present disclosure. For example, the hyper-phosphorylation of tau may comprise or be revealed by increased phosphorylation of Thr231 and/or Ser202 of tau (e.g., in the rat's brain), comparing to that in a corresponding wildtype rat. In some cases, conformationally altered tau protein, such as oligomerization and/or aggregation of tau protein may be detected in the rat (e.g., homozygous for the chimeric APP gene) of the present disclosure or the living part thereof according to the present disclosure. The oligomerization and/or aggregation of tau protein may be detectable by anti-MC1 antibody staining. In some cases, the tau protein oligomers and/or aggregates may be colocalized with tubulin and/or microtubules in the rat (e.g., homozygous for the chimeric APP gene) of the present disclosure, which is consistent with the phenotypes observed in human AD patients. Such colocalization may be detected by anti-MC1 antibody staining (for tau protein) and anti-MAP2 antibody staining (for tubulin and/or microtubules). Such oligomerization and/or aggregation of the tau protein in the rat of the present disclosure (e.g., homozygous for the chimeric APP gene) may be detected at an age as early as 24 months or earlier, such as 22 months or earlier, 20 months or earlier, 18 months or earlier, 16 months or earlier, or even still earlier. In some embodiments, neuronal loss is detectable in the rat or the living part thereof according to the present disclosure. For example, such neuronal loss may comprise apoptosis of a neuronal cell and/or necrosis of a neuronal cell (e.g., necroptosis). In some embodiments, the apoptosis is detectable by increased level of Bax, Bcl-2, Cl-caspase3, and/or Pro-caspase3 in the rat (e.g., in the rat brain) or the living part thereof comparing to that in a corresponding wildtype rat. In some embodiments, the necrosis (e.g., necroptosis) may be detectable by increased level of RIPK1 and/or pMLKL in the rat (e.g., in the rat brain) or the living part thereof comparing to that in a corresponding wildtype rat. For example, a significantly increased level of RIPK1 can be detected in a rat of the present disclosure that is homozygous for the chimeric APP gene at an age of 6 months or earlier, or 12 months or earlier. In some embodiments, RIPK3 level in the rat of the present disclosure or the living part thereof may be comparable to that in a corresponding wildtype rat. In some embodiments, comparing to a corresponding wildtype rat, no substantial change of RIPK3 expression level is detected in a rat of the present disclosure that is homozygous for the chimeric APP gene at an age of 6 months or above, or 12 months or above. In some cases, MLKL aggregation in said rat or the living part thereof may be increased comparing to that in a corresponding wildtype rat.

In the rat (or a part thereof) of the present disclosure, RIPK1 and RIPK3 expression may colocalize, revealing a presence of necrosomes in said rat or the living part thereof. For example, in the rat (or a part thereof) of the present disclosure, colocalized expression of RIPK1 and RIPK3 may be detected near the necrosomes, for example, when the rat is homozygous for the chimeric APP gene. Such colocalized expression of RIPK1 and RIPK3 near the necrosomes may be detected in the rat at an age of 12 months or earlier.

In the rat (or a part thereof) of the present disclosure, RIPK1 and MLKL expression may colocalize, revealing a presence of necrosomes in said rat or the living part thereof. For example, in the rat (or a part thereof) of the present disclosure, colocalized expression of RIPK1 and MLKL may be detected near the necrosomes, for example, when the rat is homozygous for the chimeric APP gene. Such colocalized expression of RIPK1 and MLKL near the necrosomes may be detected in the rat at an age of 12 months or earlier.

In the rat (or a part thereof) of the present disclosure, RIPK3 and MLKL expression may colocalize, revealing a presence of necrosomes in said rat or the living part thereof. For example, in the rat (or a part thereof) of the present disclosure, colocalized expression of RIPK3 and MLKL may be detected near the necrosomes, for example, when the rat is homozygous for the chimeric APP gene. Such colocalized expression of RIPK3 and MLKL near the necrosomes may be detected in the rat at an age of 12 months or earlier.

In the rat of the present disclosure or the part (e.g., tissue, organ, or other parts) thereof, increased colocalization between RIPK1 and RIPK3, between RIPK1 and MLKL, and/or between RIPK3 and MLKL may be detected, comparing to that in a corresponding wildtype rat. For example, the rat may be homozygous for the chimeric APP gene.

In the rat of the present disclosure or the part (e.g., tissue, organ, or other parts) thereof, increased aggregation of MLKL may be detected, comparing to that in a corresponding wildtype rat. For example, the rat may be homozygous for the chimeric APP gene. For example, said aggregation of MLKL may drive its localization to a cell and/or tissue membrane.

In the rat of the present disclosure or the part (e.g., tissue, organ, or other parts) thereof, colocalization of necrosomes and microglia may be detected, for example, as revealed by colocalization of RIPK1 expression and Iba1 expression. In some cases, colocalization of necrosomes, microglia and Aβ plaques may be detected, for example, as revealed by co-expression of RIPK1 and Iba1 may be detected near or at the location of an Aβ plaque, e.g., as revealed by triple staining with an anti-Iba1 antibody, an anti-RIPK1 antibody and FSB (1-Fluoro-2,5-bis[(E)-3-carboxy-4-hydroxystyryl] benzene). For example, the rat may be homozygous for the chimeric APP gene. For example, the rat may be of an age of 12 months or earlier, 10 months or earlier, 8 months or earlier, or 6 months or earlier. Such colocalization may be significantly increased in the rat or the part thereof according to the present disclosure, comparing to that in a corresponding wildtype rat.

In the rat of the present disclosure or the part (e.g., tissue, organ, or other parts) thereof, colocalization of necrosomes and microglia may be detected, for example, as revealed by colocalization of RIPK3 expression and Iba1 expression. In some cases, colocalization of necrosomes, microglia and Aβ plaques may be detected, for example, as revealed by co-expression of RIPK3 and Iba1 may be detected near or at the location of an Aβ plaque, e.g., as revealed by triple staining with an anti-Iba1 antibody, an anti-RIPK3 antibody and FSB (1-Fluoro-2,5-bis[(E)-3-carboxy-4-hydroxystyryl] benzene). For example, the rat may be homozygous for the chimeric APP gene. For example, the rat may be of an age of 12 months or earlier, 10 months or earlier, 8 months or earlier, or 6 months or earlier. Such colocalization may be significantly increased in the rat or the part thereof according to the present disclosure, comparing to that in a corresponding wildtype rat. Interestingly, such increased colocalization was observed, in spite of a similar RIPK3 expression level in the rat of the present disclosure, comparing to that in a corresponding wildtype rat.

In some embodiments, neuronal cell loss may be detectable in said rat or the living part thereof. For example, a decrease of the number of Neu-N positive neurons may be detected in said rat or the living part thereof. Such decrease may be observed in said rat or the part thereof at an age of 22 months or earlier (e.g., 20 months or earlier, such as 16 months or earlier, 10 months or earlier, or 6 months or earlier), comparing to that in a corresponding wildtype rat. For example, the rat may be homozygous for the chimeric APP gene.

In some embodiments, gliosis may be detectable in the rat or the living part thereof according to the present disclosure. The gliosis may comprise microgliosis and/or astrocytosis. In some cases, the microgliosis and/or astrocytosis may be associated with Amyloid plaques. For example, the astrocytes and microglia may be aggregated around the Amyloid plaques, and the number of the astrocytes and microglia may also be increased.

In some embodiments, synaptic degeneration may be detectable in the rat or the living part thereof according to the present disclosure. For example, the synaptic degeneration may be revealed by swelling and/or hollowing of postsynaptic density and/or the state/expression of synaptic markers. Such swelling and/or hollowing of postsynaptic density and/or presynaptic density may be detected with anti-PSD95 staining. Such state/expression of synaptic marker may be detected with anti-synaptophysin staining.

For example, the synaptic degeneration may be detectable in the rat or the living part thereof according to the present disclosure homozygous for the chimeric APP gene. For example, the synaptic degeneration may be detected in said rat or the part thereof at an age of 12 months or earlier, 9 months or earlier, or 6 months or earlier.

In some embodiments, a brain morphological and/or weight change may be detectable in said rat or the living part thereof, comparing to that in a corresponding wildtype rat. For example, the brain morphological and/or weight change may comprise a reduction of brain size, an appearance and/or enlarging of a ventricular cavity, and/or a damage in hippocampus. For example, the reduction of brain size may be detectable in the rat or the living part thereof according to the present disclosure. The rat may be homozygous for the chimeric APP gene. Such change may be detected in the rat or the part thereof at an age of 22 months or earlier, 20 months or earlier, 15 months or earlier, 10 months or earlier, or 6 months or earlier. For example, the reduction of brain weight may be detectable in the rat or the living part thereof according to the present disclosure which is homozygous for the chimeric APP gene at an age of 22 months or earlier, 20 months or earlier, 15 months or earlier, 10 months or earlier, or 6 months or earlier. For example, the enlarging of a ventricular cavity, and/or a damage in hippocampus may be detectable in the rat or the living part thereof according to the present disclosure which is homozygous for the chimeric APP gene at an age of 22 months or earlier, 20 months or earlier, 15 months or earlier, 10 months or earlier, or 6 months or earlier.

In some embodiments, cognitive impairment may be detectable in said rat comparing to a corresponding wildtype rat. For example, the cognitive impairment may be detected in an open field test, a Morris maze test and/or a T maze working memory test. For example, the cognitive function may comprise a learning function, a memory function, a cognitive function, a sensory function, a motor function and/or an emotional function.

For example, a learning function impairment may be detectable in an open field test, a Morris maze test and/or a T maze working memory test. For example, a memory function impairment may be detectable in an open field test, a Morris maze test and/or a T maze working memory test. For example, a cognitive function impairment may be detectable in an open field test, a Morris maze test and/or a T maze working memory test. For example, a sensory function impairment may be detectable in an open field test, a Morris maze test and/or a T maze working memory test.

The rat according to the present disclosure may be a knock-in rat, or may be derived from a knock-in rat. In the rat, at least a part of an endogenous APP gene may be substituted by a heterologous nucleic acid sequence encoding at least a part of the modified APP.

The at least part of the endogenous APP gene may comprise at least a part of exon 16 and at least a part of exon 17 of the endogenous APP gene. In some embodiments, the at least part of the endogenous APP gene may comprise at least a part of exon 16, at least a part of intron 16 and at least a part of exon 17 of the endogenous APP gene. In some embodiments, the at least part of the endogenous APP gene may comprise exon 16 and exon 17 of the endogenous APP gene. In some embodiments, the at least part of the endogenous APP gene may comprise exon 16, intron 16 and exon 17 of the endogenous APP gene.

The heterologous nucleic acid sequence may comprise a mutated exon 16 and a mutated exon 17. The mutated exon 16 may comprise a mutation leading to the Swedish double mutation in the APP. The mutated exon 17 may comprise one or more mutations leading to the Beyreuther/Iberian mutation and the Arctic mutation in the APP. In some embodiments, the heterologous nucleic acid sequence may be about 3.5 kb-10.5 kb (e.g., about 4 kb-10.5 kb, about 5 kb-10.5 kb, about 6 kb-10.5 kb, about 7 kb-10.5 kb, about 8 kb-10.5 kb, about 9 kb-10.5 kb) in length.

In some embodiments, the modified APP may comprise an amino acid sequence as set forth in SEQ ID NO: 2.

In another aspect, the present disclosure provides a descendant of the rat of the present disclosure. The descendant may be obtained by crossing the rat of the present disclosure with a second rat, wherein said second rat may or may not comprise the chimeric APP gene encoding the modified APP as defined in the present disclosure. In some embodiments, the descendant may comprise the chimeric APP gene encoding the modified APP as defined in the present disclosure. For example, the descendant may be an offspring of the rat of the present disclosure. In another example, the descendant may be obtained by crossing a rat of the present disclosure with another rat carrying non-identical or different genetic information (for example, may not comprise the chimeric APP gene of the present disclosure, or may comprise a further mutated/exogenous/heterologous gene fragment).

In another aspect, the present disclosure provides a cell line or primary cell culture derived from the rat or living part thereof, or from the descendant according to the present disclosure.

In another aspect, the present disclosure provides a tissue derived from the rat or living part thereof, or from the descendant according to the present disclosure. The tissue may comprise a body fluid of the rat or of the descendant. For example, the body fluid may be selected from the group consisting of: blood, plasma (e.g., plasma comprising an exosome), serum, urine, sweat, tear, saliva, semen and cerebral spinal fluid.

The tissue according to the present disclosure may comprise a brain or a part thereof from said rat or said descendant. For example, the part of the brain may comprise a portion of the brain selected from the group consisting of: olfactory bulb, amygdaloid nucleus, basal ganglia, hippocampus, thalamus, hypothalamus, cerebral cortex, medulla oblongata and cerebellum. In some embodiments, the tissue may comprise olfactory mucosa of said rat or said descendant. The tissue may also comprise a part of the central nervous system (such as the spinal cord or a part thereof), a part of the peripheral nervous system, a skin tissue, a muscle tissue, and/or a visceral organ from the rat of the present disclosure or a descendant thereof.

In another aspect, the present disclosure provides a cell derived from the rat or living part thereof, or from the descendant according to the present disclosure.

The cell according to the present disclosure may comprise a cell selected from the group consisting of: a primary neuron, a microglia, an astrocyte, an oligodendrocyte, a macrophage, a perivascular epithelioid cell, a B cell, a T cell, a somatic stem cell, an NK cell, a totipotent stem cell, a unipotent stem cell, an embryonic stem cell, an induced pluripotent stem cell, and a gamete. The gamete may comprise a sperm, and/or an oocyte.

In some embodiments, the cell may not be capable of developing into a complete rat. For example, the cell may not be a totipotent stem cell or an embryonic stem cell.

The tissue or cell may be obtained directly from a rat of the present disclosure or a living part thereof. Alternatively, the tissue or cell may be generated by introducing the heterologous nucleic acid sequence encoding the modified APP into its genome and optionally further culturing these engineered/modified cells/tissues.

In some embodiments, the rat or the living part thereof, the descendant, the cell line or primary cell culture, the tissue, or the cell according to the present disclosure may be used for screening for a substance, a device, a composition and/or a biomarker useful in the treatment, diagnosis, prevention, monitoring and/or prognosis of Alzheimer's disease. For example, a sample (e.g., cells, tissues, or other DNA- or RNA-containing sample, protein-containing sample and/or metabolite-containing sample) may be taken from the rat or the living part thereof, or the descendant according to the present disclosure before and after the appearance of an AD-associated symptom (e.g., Aβ accumulation, neurofibrillary tangle, morphologically or functionally abnormal (collapsed) synapse, neuronal cell death, or impairment of memory and learning function). Then, a gene transcription product (transcriptome), a gene translation product (proteome) or a metabolite (metabolome) derived from the sample may be comprehensively assayed and a substance that changes before and after the appearance of an AD-associated symptom may be identified.

Gene transcription products (e.g., transcriptome) may be analyzed using nucleic acid microarray, such as a DNA microarray. Gene translation products (e.g., proteome) may be analyzed using gel electrophoresis (such as a two-dimensional gel electrophoresis), or mass spectrometry (such as time-of-flight mass spectrometry, electrospray ionization mass spectrometry, capillary HPLC/MS and LC/MS/MS). Metabolites (metabolome) may be analyzed using NMR, capillary electrophoresis, LC/MS and/or LC/MS/MS.

When the presence/amount of a substance shows a significant difference before and after the appearance of an AD-associated symptom or pathology, such a substance may be considered as a biomarker of AD, which may then be used in early diagnosis (particularly a preclinical diagnosis) of AD. The identified biomarker may be further detected with a specific agent or a detection method. For example, when the biomarker is a protein or a peptide, it may be detected with an immunoassay using a specific antibody. When the biomarker is a nucleic acid molecule (such as a transcription product), it may be detected with Northern blot analysis using a specific probe, or with RT-PCR using specific primers.

Screening Methods and Uses

In another aspect, the present disclosure provides a method of screening for a substance, a device, and/or a composition useful in the treatment, prevention and/or prognosis of Alzheimer's disease, comprising applying a candidate substance, device and/or composition to the rat or living part thereof, the descendant, the cell line or primary cell culture, the tissue, and/or the cell according to the present disclosure, and determining an effect of said candidate substance, device and/or composition on one or more of the following: 1) an expression and/or accumulation of Aβ in the rat or living part thereof, the descendant, the cell line or primary cell culture, the tissue and/or the cell; 2) an expression and/or accumulation of an APP fragment (e.g., sAPP, CTF-β, CTF-α and/or AICD) in the rat or living part thereof, the descendant, the cell line or primary cell culture, the tissue and/or the cell; 3) phosphorylation of tau protein in the rat or living part thereof, the descendant, the cell line or primary cell culture, the tissue and/or the cell; 4) an oligomerization and/or aggregation of tau protein in said rat or living part thereof, said descendant, said cell line or primary cell culture, said tissue and/or said cell; 5) brain morphology and/or brain weight in said rat or living part thereof, said descendant, said cell line or primary cell culture, said tissue and/or said cell; 6) brain neurofibrillary tangle formation in the rat or living part thereof, the descendant, the cell line or primary cell culture, the tissue and/or the cell; 7) a learning function, a memory function, a cognitive function, a sensory function, a motor function, an emotional function and/or a synaptic function of the rat or the descendant; 8) brain lesion of the rat or living part thereof, the descendant and/or the tissue; 9) neuronal loss (such as neuronal cell loss), necrosome formation, neuronal death, neuronal apoptosis, neuronal necrosis, neuronal necroptosis, Neu-N positive neuron number and/or neurodegeneration in the rat or living part thereof, the descendant, the cell line or primary cell culture, the tissue and/or the cell; 10) gliosis, microglia activation, astrocyte activation, and/or inflammatory reaction in the rat or living part thereof, the descendant, the cell line or primary cell culture, the tissue and/or the cell; 11) oxidative stress and/or mitochondria dysfunction in the rat or living part thereof, the descendant, the cell line or primary cell culture, the tissue and/or the cell; 12) vascular dysfunction in the rat or living part thereof, the descendant, the cell line or primary cell culture, the tissue and/or the cell; 13) defeat of misfolded protein degradation, and/or autophage in the rat or living part thereof, the descendant, the cell line or primary cell culture, the tissue and/or the cell; and 14) brain glucose and/or lipid metabolism in the rat or living part thereof, the descendant and/or the tissue.

The method of screening may be an in vitro method, an ex vivo method, or an in vivo method.

In some embodiments, the accumulation of Aβ may comprise Aβ oligomerization and/or Amyloid plaque formation.

In some embodiments, the synaptic function may comprise synaptic transmission, synaptic plasticity, synaptic protein formation and/or function, and/or synaptic morphology.

In some embodiments, the inflammatory reaction may comprise a reaction through an innate immune cell. The innate immune cell may comprise a T cell, a B cell, an NK cell, a microphage, and/or a dendritic cell.

In some embodiments, the vascular dysfunction may comprise amyloid angiopathy and/or disruption of blood-brain barrier (BBB).

In another aspect, the present disclosure provides a use of the rat or the living part thereof, the descendant, the cell line or primary cell culture, the tissue, and/or the cell according to the present disclosure in the preparation of a system of screening for a substance, a device, a composition and/or a biomarker useful in the treatment, diagnosis, prevention, monitoring and/or prognosis of Alzheimer's disease.

The substance, device and/or composition useful in the treatment, prevention and/or prognosis of Alzheimer's disease may be a substance, device and/or composition that suppresses the accumulation of Aβ, suppresses the neurofibrillary tangle and/or suppresses brain lesion such as neurodegeneration and inflammatory reaction. The substance, device and/or composition may be useful as a candidate drug or device for the treatment, prevention and/or prognosis of Alzheimer's disease.

In the method, a candidate substance, device and/or composition may be applied to the rat of the present disclosure, its living part, its descendant, or a cell/tissue derived therefrom and then, Aβ accumulation in the brain, the brain neurofibrillary tangle and/or brain lesion (such as neurodegeneration and inflammatory reactions) may be examined.

A candidate substance may be a synthetic compound, a peptide, a protein, a DNA library or a nucleic acid molecule in the library, a tissue extract or cell culture supernatant of an animal (e.g., a mammal, such as a mouse, a rat, a pig, cattle, a sheep, a monkey, or a human being), an extract or a cultured product from a plant or a microorganism, or any mixtures thereof.

In the present disclosure, the device may comprise a medical device, such as a medical device alleged to be effective in the treatment, diagnosis, prevention, monitoring and/or prognosis of Alzheimer's disease.

In the present disclosure, the composition may comprise a mixture derived from one or more organisms. The organism may be a plant, an animal and/or a microorganism. For example, the composition may comprise a tissue homogenate and/or a blood sample. In some embodiments, the composition may comprise extracts from one or more plants. For example, the composition may comprise a candidate traditional Chinese medicine.

In the method, after treating the rat of the present disclosure, its living part, its descendant, or a cell/tissue derived therefrom with the candidate substance, device and/or composition, the brain or brain tissue/cell may be isolated from the treated rat, its living part or descendant. Then, the brain or brain tissue/cell may be homogenized using a suitable buffer (such as a phosphate-buffered saline) to obtain a homogenized solution. A soluble fraction and/or an insoluble fraction may then be isolated from the homogenized solution. Afterwards, the isolated soluble fraction and/or insoluble fraction may be examined with an immunoassay, e.g., using an anti-Aβ antibody and/or an anti-APP antibody. In some embodiments, the amount of Aβ42 and Aβ40 can be measured. In some embodiments, the ratio of Aβ42/Aβ40 can be calculated as well.

In some cases, after isolating the brain or brain tissue/cell, a frozen section or a paraffin-embedded section of the brain or brain tissue/cell may be prepared. Then, APP/Aβ deposition may be evaluated, e.g., by immunostaining the brain section with an anti-APP antibody and/or an anti-Aβ antibody. In addition, synapse abnormality may be evaluated by immunostaining the brain section with an antibody against a marker protein of the presynapse or the dendrite. Morphological abnormality of cell skeleton proteins may be evaluated by immunostaining the brain section with an antibody against the phosphorylated tau. Neuronal cell death may be evaluated with Nissl body staining or HE staining (e.g., as described in Am. J. Pathol., vol. 165, pages 1289-1300, (2004)). The results may be compared with that of a control group (e.g., wherein the candidate substance, device and/or composition has not been applied, or a blank control buffer has been applied instead of the candidate substance, device and/or composition).

Comparing to the results obtained from the control group, after applying the candidate substance, device and/or composition, if the total amount of Aβ decreases, the amount of Aβ42 decreases and/or the ratio of Aβ42/Aβ40 decreases, then, the candidate substance, device and/or composition may be selected for further study (e.g., as a potential therapeutic agent/device/composition for treating AD, or for suppressing the accumulation of Aβ).

Comparing to the results obtained from the control group, after applying the candidate substance, device and/or composition, if amyloid deposition decreases, neurofibrillary tangle decreases, synapse abnormality (collapse) decreases, neuronal cell death decreases and/or inflammatory reaction decreases, then, the candidate substance, device and/or composition may be selected for further study (e.g., as a potential therapeutic agent/device/composition for treating AD, for suppressing the accumulation of Aβ, for suppressing neurofibrillary tangle, for suppressing brain lesion (e.g., neurodegeneration) or inflammatory reaction).

A learning function, a memory function, a cognitive function, synaptic function (e.g., synaptic transmission, synaptic plasticity, synaptic protein formation and/or function, and/or synaptic morphology), sensory function (e.g., olfactory sensation, auditory sensation, gustation, tactile sensation, etc.), a motor function (e.g., local motor function, muscle function, etc.), an emotional function (e.g., depression level) may also be compared between the group treated with the candidate substance, device and/or composition and the control group, e.g., by conducting animals' behavioral analysis. For example, comparing to the results obtained from the control group, after applying the candidate substance, device and/or composition, if a significant improvement in learning and memory impairment, synaptic function, sensory function, motor function and/or emotional function is observed, then the candidate substance, device and/or composition may be selected for further study (e.g., as a potential therapeutic agent/device/composition for treating learning and memory disorder).

In some cases, the method of screening may also be performed using tissues and/or cells derived from the rat according to the present disclosure, such as neuronal cells, brain regions or other tissues comprising or corresponding to the lesion of AD or parts thereof (e.g., olfactory bulb, amygdaloid nucleus, basal ganglia, hippocampus, thalamus, hypothalamus, cerebral cortex, medulla oblongata, central nervous system, peripheral nervous system, spinal cord, cerebellum, skin tissue, muscle tissue, and/or visceral organ). For example, the tissues and/or cells may be cultured in vitro or ex vivo, then, the candidate substance, device and/or composition may be applied to the cultured tissues and/or cells, after being incubated for an appropriate period of time (e.g., a few hours, a few days, a few weeks or a few months), the tissues or cells may be examined with a method as described above for the brain tissue/cells isolated from the treated rat.

In another aspect, the present disclosure provides a screening method for a substance having an affinity for APP or Aβ. For example, a candidate substance may be applied to the rat of the present disclosure or a living part thereof, then, a presence of the candidate substance in an area of Aβ accumulation may be examined. A candidate substance having a specific affinity for APP or Aβ may be used in early diagnosis of AD.

In another aspect, the present disclosure provides a method of screening for a biomarker useful in the diagnosis and/or monitoring of Alzheimer's disease. The method may comprise determining a presence and/or a level of a substance in a sample obtained from the rat or living part thereof or from the descendant according to the present disclosure, before and after detection of an indication of the Alzheimer's disease, and identifying a substance showing a change of the presence and/or level before and after the detection.

For example, in a method of screening for such a biomarker, a sample (e.g., cells, tissues, or other DNA- or RNA-containing sample, protein-containing sample and/or metabolite-containing sample) may be taken from the rat, its living part, or its descendant according to the present disclosure before and after the appearance of an AD-associated symptom (e.g., Aβ accumulation, neurofibrillary tangle, morphologically or functionally abnormal (collapsed) synapse, neuronal cell death, or impairment of memory and learning function). Then, a gene transcription product (transcriptome), a gene translation product (proteome) or a metabolite (metabolome) derived from the sample may be comprehensively assayed and a substance that changes before and after the appearance of an AD-associated symptom may be identified. In some embodiments, the sample may comprise a body fluid of the rat, such as the blood, plasma (e.g., plasma comprising an exosome), serum, urine, sweat, tear, saliva, semen and/or cerebral spinal fluid of the rat.

Gene transcription products (e.g., transcriptome) may be analyzed using nucleic acid microarray, such as a DNA microarray. Gene translation products (e.g., proteome) may be analyzed using gel electrophoresis (such as a two-dimensional gel electrophoresis), or mass spectrometry (such as time-of-flight mass spectrometry, electronspray ionization mass spectrometry, capillary HPLC/MS and LC/MS/MS). Metabolites (metabolome) may be analyzed using NMR, capillary electrophoresis, LC/MS and/or LC/NIS/MS.

When the presence/amount of a substance shows a significant difference before and after the appearance of an AD-associated symptom or pathology, such a substance may be considered as a biomarker of AD, which may then be used in early diagnosis (particularly a preclinical diagnosis) of AD. The identified biomarker may be further detected with a specific agent or a detection method. For example, when the biomarker is a protein or a peptide, it may be detected with an immunoassay using a specific antibody. When the biomarker is a nucleic acid molecule (such as a transcription product), it may be detected with Northern blot analysis using a specific probe, or with RT-PCR using specific primers.

Methods for Generating the Model Animal

In another aspect, the present disclosure provides a method for generating the rat or the living part thereof according to the present disclosure. The method may comprise knocking-in a heterologous nucleic acid sequence into an endogenous APP gene locus of a rat, e.g., to provide a chimeric APP gene in the rat. The knocking-in may substitute at least a part of an endogenous APP gene with a heterologous nucleic acid sequence encoding at least a part of the modified APP.

The at least part of the endogenous APP gene may comprise at least a part of exon 16 and at least a part of exon 17 of the endogenous APP gene. In some cases, the at least part of the endogenous APP gene may comprise at least a part of exon 16, at least a part of intron 16 and at least a part of exon 17 of the endogenous APP gene. The heterologous nucleic acid sequence may comprise a mutated exon 16 and a mutated exon 17. In some embodiments, the at least part of the endogenous APP gene may comprise exon 16 and exon 17 of the endogenous APP gene. In some cases, the at least part of the endogenous APP gene may comprise exon 16, intron 16 and exon 17 of the endogenous APP gene. In some embodiments, the heterologous nucleic acid sequence may comprise a mutated exon 16, an intron 16 and a mutated exon 17 of APP.

Mutations in the mutated exon 16 and mutated exon 17 may introduce multiple amino acid substitutions in their encoded polypeptides (e.g., the protein product they encode), and the multiple amino acid substitutions may comprise an amino acid substitution at the following residues: K670, M671, I716 and E693. For example, the multiple amino acid substitutions may comprise an amino acid substitution of K670, an amino acid substitution of M671, an amino acid substitution of I716 and an amino acid substitution of E693. The multiple amino acid substitutions may further comprise the following amino acid substitutions: G676R, F681Y and R684H. In some embodiments, the multiple amino acid substitutions comprise the substitution K670N, M671L, I716F, and/or E693G. In some embodiments, the multiple amino acid substitutions comprise the substitutions K670N, M671L, I716F, E693G, G676R, F681Y and R684H.

In the method of the present disclosure for generating the model animal, nuclease agents may be utilized to aid in the modification of the target APP gene locus. Such a nuclease agent may promote homologous recombination between the donor nucleic acid molecule and the target genomic locus. In some embodiments, the nuclease agent comprises an endonuclease agent.

As used herein, the term "recognition site for a nuclease agent" generally refers to a DNA sequence at which a nick or double-strand break may be induced by a nuclease agent. The recognition site for a nuclease agent can be endogenous (or native) to the cell or the recognition site can be exogenous to the cell. In some embodiments, the recognition site may be exogenous to the cell and thereby is not naturally occurring in the genome of the cell. In further embodiments, the exogenous or endogenous recognition site may be present only once in the genome of the host cell. In specific embodiments, an endogenous or native site that occurs only once within the genome may be identified. Such a site can then be used to design nuclease agents that will produce a nick or double-strand break at the endogenous recognition site.

The length of the recognition site can vary, and includes, for example, recognition sites that are at least 4, 6, 8, 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length. In one embodiment, each monomer of the nuclease agent may recognize a recognition site of at least 9 nucleotides. In other embodiments, the recognition site may be from about 9 to about 12 nucleotides in length, from about 12 to about 15 nucleotides in length, from about 15 to about 18 nucleotides in length, or from about 18 to about 21 nucleotides in length, and any combination of such subranges (e.g., 9-18 nucleotides). The recognition site could be palindromic, that is, the sequence on one strand reads the same in the opposite direction on the complementary strand. It is recognized that a given nuclease agent can bind the recognition site and cleave that binding site or alternatively, the nuclease agent can bind to a sequence that is the different from the recognition site. Moreover, the term recognition site may comprise both the nuclease agent binding site and the nick/cleavage site irrespective whether the nick/cleavage site is within or outside the nuclease agent binding site. In another variation, the cleavage by the nuclease agent can occur at nucleotide positions immediately opposite each other to produce a blunt end cut or, in other cases, the incisions can be staggered to produce single-stranded overhangs, also called "sticky ends", which can be either 5' overhangs, or 3' overhangs.

Any nuclease agent that induces a nick or double-strand break into a desired recognition site can be used in the methods of the present disclosure. A naturally-occurring or native nuclease agent can be employed so long as the nuclease agent induces a nick or double-strand break in a desired recognition site. Alternatively, a modified or engineered nuclease agent can be employed. An "engineered nuclease agent" comprises a nuclease that is engineered (modified or derived) from its native form to specifically recognize and induce a nick or double-strand break in the desired recognition site. Thus, an engineered nuclease agent can be derived from a native, naturally-occurring nuclease agent or it can be artificially created or synthesized. The modification of the nuclease agent can be as little as one amino acid in a protein cleavage agent or one nucleotide in a nucleic acid cleavage agent. In some embodiments, the engineered nuclease may comprise a nick or double-strand break in a recognition site, wherein the recognition site was not a sequence that would have been recognized by a native (non-engineered or non-modified) nuclease agent. Producing a nick or double-strand break in a recognition site or other DNA can be referred to herein as "cutting" or "cleaving" the recognition site or other DNA.

In some embodiments, the nuclease agent may be a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases may be created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See, WO 2010/079430; Morbitzer et al. (2010) PNAS 10.1073/pnas.1013133107; Scholze & Boch (2010) Virulence 1:428-432; Christian et al. Genetics (2010) 186:757-761; Li et al. (2010) Nuc. Acids Res. (2010) doi:10.1093/nar/gkq704; and Miller et al. (2011) Nature Biotechnology 29:143-148; all of which are herein incorporated by reference.

In some embodiments, the nuclease agent may be a zinc-finger nuclease (ZFN). For example, each monomer of the ZFN may comprise 3 or more zinc finger-based DNA binding domains, wherein each zinc finger-based DNA binding domain may bind to a 3 bp subsite. In other embodiments, the ZFN may be a chimeric protein comprising a zinc finger-based DNA binding domain operably linked to an independent nuclease. In some embodiments, the independent endonuclease may be a FokI endonuclease. In some embodiments, the nuclease agent may comprise a first ZFN and a second ZFN, wherein each of the first ZFN and the second ZFN is operably linked to a FokI nuclease, wherein the first and the second ZFN recognize two contiguous target DNA sequences in each strand of the target DNA sequence separated by about 6 bp to about 40 bp cleavage site or about a 5 bp to about 6 bp cleavage site, and wherein the FokI nucleases dimerize and make a double strand break. See, for example, US20060246567; US20080182332; US20020081614; US20030021776; WO/2002/057308A2; US20130123484; US20100291048; and, WO/2011/017293A2, each of which is herein incorporated by reference.

In some embodiments, the nuclease agent may be a meganuclease. Meganucleases have been classified into four families based on conserved sequence motifs, the families are the LAGLIDADG (SEQ ID NO: 13), GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates. Meganuclease domains, structure and function are known, see for example, Guhan and Muniyappa (2003) Crit. Rev Biochem Mol Biol 38:199-248; Lucas et al., (2001) Nucleic Acids Res 29:960-9; Jurica and Stoddard, (1999) Cell Mol Life Sci 55:1304-26; Stoddard, (2006) Q Rev Biophys 38:49-95; and Moure et al., (2002) Nat Struct Biol 9:764.

In some embodiments, the nuclease agent employed in the methods of the present disclosure may employ a CRISPR/Cas system. Such systems can employ, for example, a Cas9 nuclease, which in some instances, may be codon-optimized for the desired cell type in which it is to be expressed. The system may further employ a fused crRNA-tracrRNA construct that functions with the codon-optimized Cas9. This single RNA may be often referred to as a small guide RNA or sgRNA. Within an sgRNA, the crRNA portion may be identified as the "nucleotide sequence hybridizing to the target sequence of the endogenous APP gene" (or a "targeting sequence") and the tracrRNA may be often referred to as the "scaffold". Briefly, a short DNA fragment containing the targeting sequence may be inserted into an sgRNA expression plasmid. The sgRNA expression plasmid may comprise the targeting sequence (in some embodiments around 20 nucleotides), a form of the tracrRNA sequence (the scaffold) as well as a suitable promoter that is active in the cell and necessary elements for proper processing in eukaryotic cells (such as rat cells). The sgRNA expression cassette and the Cas9 expression cassette may then be introduced into the cell. See, for example, Mali P et al. (2013) Science 2013 Feb. 15; 339(6121):823-6; Jinek M et al. Science 2012 Aug. 17; 337(6096):816-21; Hwang W Y et al. Nat Biotechnol 2013 March; 31(3):227-9; Jiang W et al. Nat Biotechnol 2013 March; 31(3):233-9; and, Cong L et al. Science 2013 Feb. 15; 339(6121):819-23, each of which is herein incorporated by reference.

In some embodiments of the method, the knocking-in may comprise contacting the genome of a stem cell or a zygote of a rat with the following in the presence of a donor nucleic acid molecule comprising the heterologous nucleic acid sequence: 1) a CRISPR associated (Cas) protein; and 2) one or more ribonucleic acid (RNA) sequences that comprise: i) a portion complementary to a portion of the endogenous APP gene upstream of exon 16 (or a first crRNA); ii) a portion complementary to a portion of the endogenous APP gene downstream of exon 17 (or a second crRNA); and iii) a binding site for the Cas protein.

In some embodiments of the method, the knocking-in may further comprise maintaining the cell or zygote under conditions in which the one or more RNA sequences hybridize to the portion of the endogenous APP gene upstream of exon 16 and the portion of the endogenous APP gene downstream of exon 17, and the Cas protein cleaves the endogenous APP gene nucleic acid sequence upon the hybridization of the one or more RNA sequences.

In some embodiments of the method, the knocking-in may further comprise substituting at least a part of the endogenous APP gene with the heterologous nucleic acid sequence encoding at least a part of the modified APP.

The Cas protein may be a type I Cas protein. In some embodiments, the Cas protein may be a type II Cas protein. In some embodiments, the type II Cas protein may be Cas9.

In some embodiments of the method, the stem cell may be selected from the group consisting of: an embryonic stem cell, a somatic stem cell, a totipotent stem cell, a unipotent stem cell and an induced pluripotent stem cell.

In some embodiments of the method, the binding site for the Cas protein may comprise a tracrRNA sequence.

In some embodiments of the method, the Cas protein may be introduced into the cell or zygote of the rat in the form of a protein, a messenger RNA(mRNA) encoding the Cas protein, or a DNA encoding the Cas protein.

In some embodiments of the method, the one or more RNA sequences may be introduced into the cell or zygote in the form of one or more RNA molecules or one or more DNA molecules encoding the RNA sequences.

In some embodiments of the method, the portion complementary to a portion of the endogenous APP gene upstream of exon 16 or the portion complementary to a portion of the endogenous APP gene downstream of exon 17 may be encoded by a nucleic acid molecule comprising a sequence as set forth in any one of SEQ ID NOs: 3-12.

In some embodiments of the method, the portion complementary to a portion of the endogenous APP gene upstream of exon 16 may be encoded by a nucleic acid molecule comprising a sequence as set forth in SEQ ID NO: 3.

In some embodiments of the method, the portion complementary to a portion of the endogenous APP gene downstream of exon 17 may be encoded by a nucleic acid molecule comprising a sequence as set forth in SEQ ID NO: 4.

The modified APP may comprise an amino acid sequence as set forth in SEQ ID NO:2.

In some embodiments, the method may further comprise identifying a genetically modified stem cell or zygote of the rat comprising the knocked-in heterologous nucleic acid sequence.

In some embodiments, the method may further comprise introducing the genetically modified stem cell or zygote of the rat into a host rat embryo.

In some embodiments, the method may further comprise gestating the host rat embryo in a surrogate mother; wherein the surrogate mother produces a rat progeny comprising a modified APP gene locus that comprises the heterologous nucleic acid sequence (e.g., in the chimeric APP) knocked-in. The heterologous nucleic acid sequence may be capable of being transmitted through the germline.

The donor nucleic acid molecule comprising the heterologous nucleic acid sequence may also comprise a 5' homologous arm and a 3' homologous arm. The 5' homologous arm and the 3' homologous arm may flank the heterologous nucleic acid sequence encoding at least a part of the modified APP. A homologous arm in the donor nucleic acid molecule (e.g., the 5' homologous arm or the 3' homologous arm) may be of any length that is sufficient to promote a homologous recombination event with a corresponding region in the endogenous APP gene locus, for example, at least 5 bps, at least 50 bps, at least 100 bps, at least 150 bps, at least 200 bps, at least 300 bps, at least 400 bps, at least 500 bps, at least 600 bps, at least 700 bps, at least 750 bps, at least 800 bps, at least 850 bps, at least 900 bps, at least 1 kb, at least 1.5 kb, at least 5 kb in length or greater. In some embodiments, the donor nucleic acid molecule comprises a 5' homologous arm that may be about 800-900 bps in length and a 3' homologous arm that may be about 800-950 bps in length.

As used herein, a homologous arm and a target site (i.e., a cognate genomic region, or a corresponding region within the endogenous APP gene locus) match or correspond to one another when the two regions share a sufficient level of sequence identity to one another to act as substrates for a homologous recombination reaction. By "homology", it is meant that the DNA sequences either are identical or share a certain sequence identity to a corresponding or matching sequence. The sequence identity between a given target site and the corresponding homologous arm found in the donor nucleic acid molecule can be any degree of sequence identity that allows for homologous recombination to occur. For example, the amount of sequence identity shared by the homologous arm of the donor nucleic acid molecule (or a fragment thereof) and the target site (or a fragment thereof) can be at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or at least 100%, such that the sequences undergo homologous recombination.

For example, in the donor nucleic acid molecule, the heterologous nucleic acid sequence encoding at least a part of the modified APP may be flanked by: 1) a first homologous arm (or a 5' homologous arm) corresponding to a first region of the endogenous APP gene locus upstream of exon 16; and 2) a second homologous arm (or a 3' homologous arm) corresponding to a second region of the endogenous APP gene locus downstream of exon 17. As such, the donor nucleic acid molecule thereby aids in the integration of the heterologous nucleic acid sequence into the endogenous APP gene locus of the rat genome through a homologous recombination event that occurs between the homologous arms and their corresponding regions within the endogenous APP gene locus.

When nuclease agents (e.g., the Cas protein) are employed, the cognate genomic regions corresponding to the 5' and 3' homologous arms of a donor nucleic acid molecule are located in sufficient proximity to the nuclease target sites so as to promote the occurrence of a homologous recombination event between the cognate genomic regions and the homologous arms upon a nick or double-strand break at the recognition site. For example, the nuclease target sites can be located anywhere between the cognate genomic regions corresponding to the 5' and 3' homologous arms. In some embodiments, the recognition site is immediately adjacent to at least one or both of the corresponding cognate genomic regions.

The donor nucleic acid molecule may also comprise a selection cassette or a reporter gene. The selection cassette may comprise a nucleic acid sequence encoding a selection marker, wherein the nucleic acid sequence is operably linked to a promoter. The promoter may be active in a prokaryotic cell of interest and/or active in a eukaryotic cell of interest. Such promoters may be an inducible promoter, a promoter that is endogenous to the reporter gene or the cell, a promoter that is heterologous to the reporter gene or to the cell, a cell-specific promoter, a tissue-specific promoter or a developmental stage-specific promoter. In some embodiments, the selection marker may be selected from the group consisting of: Ampicilin resistance gene (Ampr), neomycin phosphotransferase (neor), hygromycin B phosphotransferase (hygr), puromycin-N-acetyltransferase (puror), blasticidin S deaminase (bsrr), xanthine/guanine phosphoribosyl transferase (gpt) and herpes simplex virus thymidine kinase (HSV-k) and a combination thereof. The selection marker of the donor nucleic acid molecule may be flanked by the 5' and 3' homologous arms or found either 5' or 3' to the homologous arms.

In some embodiments, the donor nucleic acid molecule may comprise a reporter gene operably linked to a promoter, wherein the reporter gene encodes a reporter protein selected from the group consisting of: LacZ, mPlum, mCherry, tdTomato, mStrawberry, J-Red, DsRed, mOrange, mKO, mCitrine, Venus, YPet, enhanced yellow fluorescent protein (EYFP), Emerald, enhanced green fluorescent protein (EGFP), CyPet, cyan fluorescent protein (CFP), Cerulean, T-Sapphire, luciferase, alkaline phosphatase and a combination thereof. Such reporter genes can be operably linked to a promoter active in the cell. Such promoters can be an inducible promoter, a promoter that may be endogenous to the report gene or the cell, a promoter that may be heterologous to the reporter gene or to the cell, a cell-specific promoter, a tissue-specific promoter or a developmental stage-specific promoter.

In the one or more RNA sequences, the portion complementary to a portion of the endogenous APP gene upstream of exon 16, the portion complementary to a portion of the endogenous APP gene downstream of exon 17, and the binding site for the Cas protein (e.g., the tracrRNA) may be comprised in the same RNA molecule or in different RNA molecules. They may be introduced together in the form of a single transcript or may be introduced separately into the stem cell or zygote of the rat.

In some embodiments, the Cas protein, the RNA portion complementary to a portion of the endogenous APP gene upstream of exon 16, the RNA portion complementary to a portion of the endogenous APP gene downstream of exon 17, and the binding site for the Cas protein (e.g., the tracrRNA) may be introduced into the stem cell or zygote of the rat as a protein-RNA complex.

In some embodiments, the DNA encoding the Cas protein may be in the form of a first expression construct comprising a first promoter operably linked to a nucleic acid encoding the Cas protein.

In some embodiments, the DNA encoding the RNA portion complementary to a portion of the endogenous APP gene upstream of exon 16 may be in the form of a second expression construct comprising a second promoter operably linked to a nucleic acid encoding said RNA portion.

In some embodiments, the DNA encoding the RNA portion complementary to a portion of the endogenous APP gene downstream of exon 17 may be in the form of a third expression construct comprising a third promoter operably linked to a nucleic acid encoding said RNA portion.

In some embodiments, the DNA encoding the binding site for the Cas protein (e.g., the tracrRNA) may be in the form of a fourth expression construct comprising a fourth promoter operably linked to a nucleic acid encoding the binding site for the Cas protein (e.g., the tracrRNA).

The first, second, third and fourth promoters may be active in the stem cell or zygote of the rat.

In some embodiments, the first, second, third and/or fourth expression constructs may be in a single nucleic acid molecule.

In some embodiments, the DNA encoding the Cas protein may be in the form of a first expression construct comprising a first promoter operably linked to a nucleic acid encoding the Cas protein; the DNA encoding the RNA portion complementary to a portion of the endogenous APP gene upstream of exon 16 and the DNA encoding the binding site for the Cas protein (e.g., the tracrRNA) may be in the form of a second expression construct comprising a second promoter operably linked to a nucleic acid encoding the RNA portion and the binding site in a single transcript. The first and the second promoters may be active in the stem cell or zygote of the rat. In some cases, the first and the second expression constructs may be in a single nucleic acid molecule.

In some embodiments, the DNA encoding the Cas protein may be in the form of a first expression construct comprising a first promoter operably linked to a nucleic acid encoding the Cas protein; the DNA encoding the RNA portion complementary to a portion of the endogenous APP gene downstream of exon 17 and the DNA encoding the binding site for the Cas protein (e.g., the tracrRNA) may be in the form of a second expression construct comprising a second promoter operably linked to a nucleic acid encoding the RNA portion and the binding site in a single transcript. The first and the second promoters may be active in the stem cell or zygote of the rat. In some cases, the first and the second expression constructs are in a single nucleic acid molecule.

In some embodiments, the portion of the endogenous APP gene upstream of exon 16 and/or the portion of the endogenous APP gene downstream of exon 17 may be immediately flanked (e.g., in the 3' end) by a Protospacer Adjacent Motif (PAM) sequence.

In some cases, the stem cell or zygote of the rat may be a rat embryonic stem (ES) cell. For example, the stem cell of the rat may be derived from a DA strain or an ACI strain. In some embodiments, the stem cell of the rat may be characterized by expression of at least one pluripotency marker selected from the group consisting of: Dnmt3L, Eras, Err-beta, Fbxo15, Fgf4, Gdf3, Klf4, Lef1, LIF receptor, Lin28, Nanog, Oct4, Sox15, Sox2, Utf1 and a combination thereof. In some embodiments, the stem cell of the rat may be characterized by one or more of the following features: (a) lack of expression of one or more pluripotency markers may be selected from the group consisting of: c-Myc, Ecat1 and Rexo1; (b) lack of expression of one or more mesodermal markers may be selected from the group consisting of Brachyury and Bmpr2; (c) lack of expression of one or more endodermal markers may be selected from the group consisting of Gata6, Sox17 and Sox7; or (d) lack of expression of one or more neural markers may be selected from the group consisting of Nestin and Pax6.

In some embodiments, the knocking-in may comprise injecting the donor nucleic acid molecule comprising the heterologous nucleic acid sequence of the present disclosure into a fertilized egg of a rat.

EXAMPLES

The following examples are set forth so as to provide those of ordinary skill in the art with a complete disclosure and description of how to make and use the present invention and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Construction of Donor Nucleic Acid Molecule

After searching the genomic DNA of rat App from NCBI database, the App gene was found to span about 216.3 kb on the reverse strand of chromosome 11. The Gene ID (From database NCBI) is: 54226. There are 2 transcripts of this gene (From Ensembl, Protein ID is ENSRNOP00000041613 and ENSRNOP00000040243, respectively). The various domains and features of the rat APP gene were analyzed.

Then, rat App genomic DNA was isolated, which included exon 16, intron 16 and exon 17. The fragment including exon 16 and exon 17 is about 4 kb. Then, the Aβ sequence in the rat APP was humanized by introducing mutations leading to the substitutions G676R, F681Y, and R684H. Furthermore, Swedish double mutations (K670N substitution and M671L substitution) were introduced into exon 16, and Beyreuther/Iberian (I716F substitution) and Arctic (E693G substitution) mutations were introduced into exon 17. FIG. 1 provides a scheme indicating the mutations introduced to obtain the modified rat APP. The donor vector was prepared using an endotoxin-free plasmid DNA kit.

Figure 5:
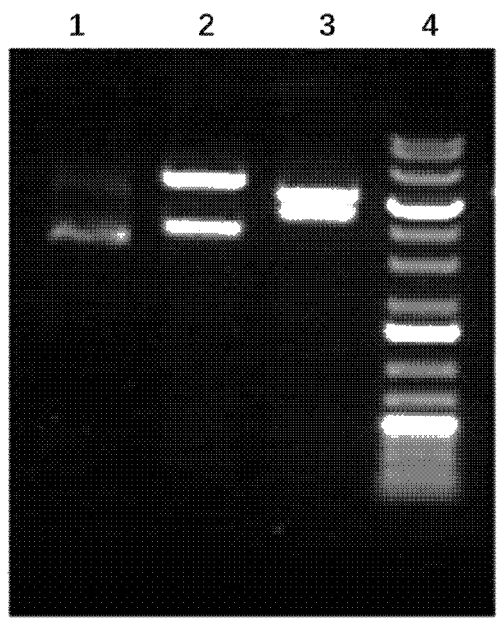
FIG. 5 illustrates enzymatic digesting results of targeting vectors.
Figure 24:
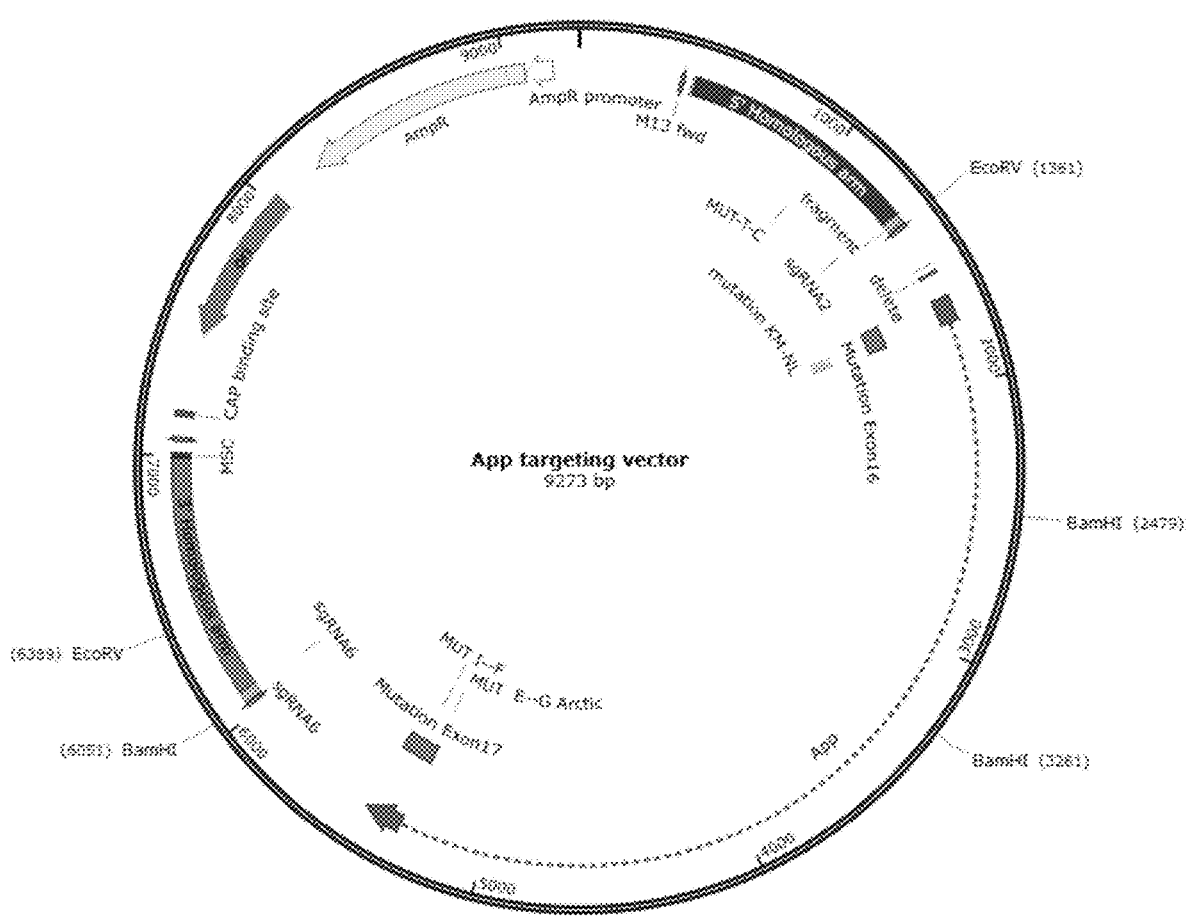
FIG. 24 illustrates a schematic map of an APP targeting vector of the present disclosure.

The mutated nucleic acid sequences were confirmed by DNA sequencing, as well as by enzyme digestion. As shown in FIG. 5, lane 1 was loaded with control sequences, lane 2 was loaded with digestion products of HindIII (expected size was 3620 bp and 5633 bp, respectively), lane 3 was loaded with digestion products of EcoRV (expected size was 4245 bp and 5028 bp, respectively), and lane 4 was loaded with DNA markers. The donor nucleic acid molecule comprises a 5' homologous arm of 889 bp upstream of exon 16, and a 3' homologous arm of 902 bp downstream of exon 17. A scheme of an APP targeting vector comprising the donor nucleic acid molecule is shown in FIG. 24.

Example 2

CRISPR Construction and Activity Assay

Figure 2:
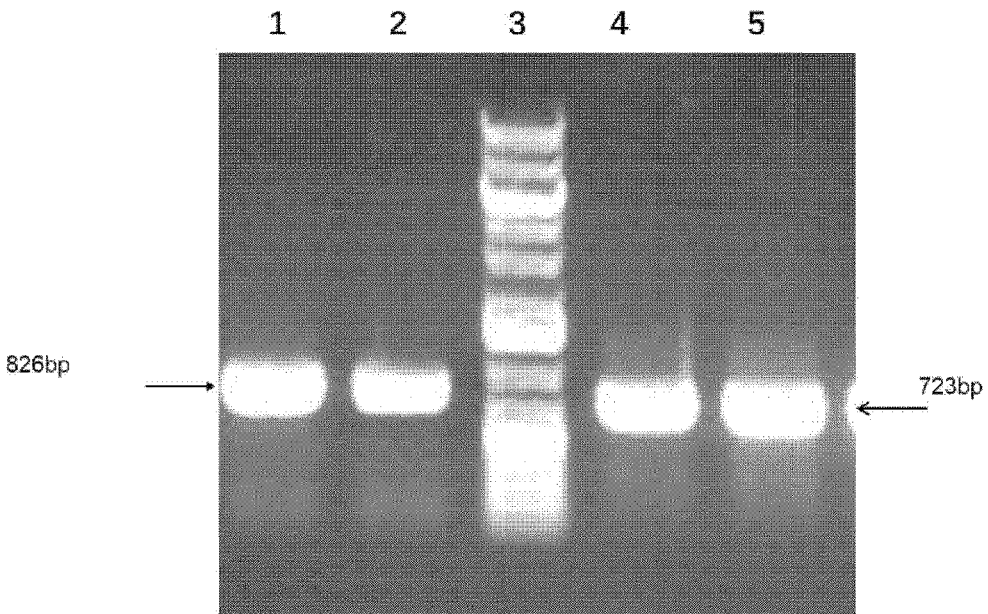
FIG. 2 shows sequencing results of potential CRISPR RNA targeting sites.

The target gene sequence (i.e., target App gene sequence) may be different in different rat strains. Thus, to make sure of the efficiency of Cas9/sgRNA and to ensure consistent DNA sequences between sgRNA target and the sequences obtained from rat tail targets, PCR and DNA sequencing were performed with genomic DNAs obtained from rat tails. The results are shown in FIG. 2. Lane 1 and lane 2 were loaded with PCR amplification products of upstream target sequences, lane 3 was loaded with DNA marker, lane 4 and lane 5 were loaded with PCR amplification products of downstream target sequences.

In can be seen that the sequences obtained from the PCR products obtained in rat tails were the same as those recorded in the NCBI and Ensembl databases.

SgRNAs were designed to be around the insertion sites (which were in the intron regions), insertion of heterologous fragments containing enzymatic restriction sites is easy to identify.

Figures 3A, 3B:
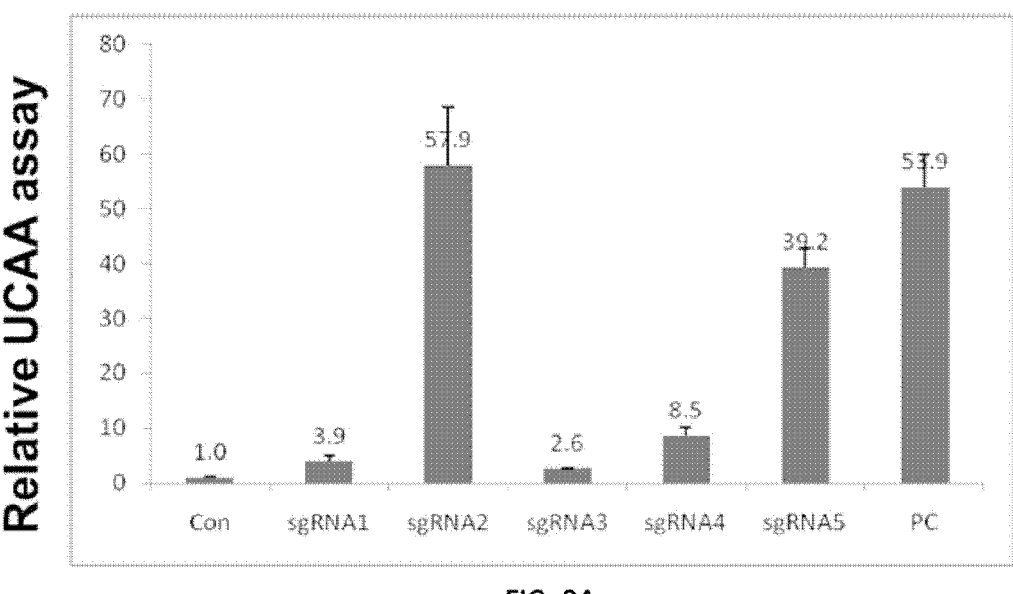
FIGS. 3A-3B illustrate the activity of various sgRNAs.

10 different sgRNA sequences were designed, and the sequences they target (e.g., hybridize to) are as set forth in SEQ ID NO: 3-12, respectively. DNA oligos of these sgRNAs were synthesized and ligated into the pCS(puro) vector, respectively. The activity of these 10 different sgRNAs was evaluated using the universal CRISPR activity Assay (UCA, Beijing Biocytogen Co. Ltd.). The results are shown in FIGS. 3A-3B. It can be seen that among the 10 sgRNAs, sgRNA2 (its target sequence is as set forth in SEQ ID NO: 3) and sgRNA6 (its target sequence is as set forth in SEQ ID NO: 4) have shown the highest relatively activity and were chosen to be used in generating the knock-in rats.

Figure 4:
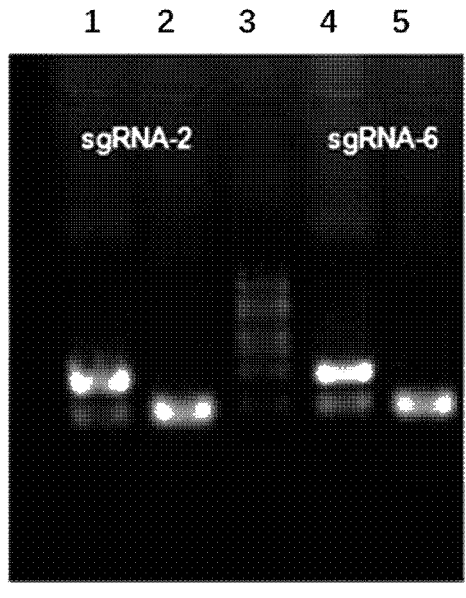
FIG. 4 illustrates sequencing results of ligated sgRNAs.

Then, sgRNA2 and sgRNA6 were ligated into a vector with T7 promoter, respectively, to obtain in vitro transcribed sgRNAs to be used in microinjection. The transcribed sgRNA2 and sgRNA6 (65° C., 5 mins) were confirmed, as shown in FIG. 4. Lane 1 was loaded with in vitro transcribed sgRNA-2 (denatured), lane 2 was loaded with in vitro transcribed sgRNA-2 (undenatured), lane 3 was loaded with DNA marker, lane 4 was loaded with in vitro transcribed sgRNA-6 (denatured) and lane 5 was loaded with in vitro transcribed sgRNA-6 (undenatured).

Similarly, Cas9 mRNA was transcribed with T7 RNA polymerase in vitro. Briefly, the T7 promoter sequence was added to the Cas9 templates by PCR amplification. T7-Cas9 PCR products were gel purified and used as the template for in vitro transcription with the MEGAshortscript T7 kit (Life Technologies) according to the kit protocol. Cas9 mRNA was purified using the MEGAclear kit and eluted with RNase-free water.

Example 3

Injection of Cas9/sgRNA and the Donor Nucleic Acid Molecule

All animal experiments were carried out according to the recommendations of AAALAC (Association for Assessment and Accreditation of Laboratory Animal Care International). The IACUC (Institutional Animal Care and Use Committee) of Tsinghua University approved animal protocol (15-LB5) used in this study. Rats were maintained on a standard 12 h light/12 h dark cycle and were housed in groups of one to two. Food and water were provided ad libitum unless otherwise noted.

Selected single cell zygotes of the rats were transferred into prepared strips M2 medium and were arranged in a row (about 30-50 eggs/row). Injection dish was placed on the stage of an inverted microscope, so that the droplets M2 elongated in the vertical direction of the operator, i.e., the y-axis. The in vitro transcribed Cas9 mRNA, sgRNA2 and sgRNA6 (obtained according to Example 2), as well as the APP targeting vector comprising the donor nucleic acid molecule (obtained according to Example 1) were injected into the rat zygotes. The needles were removed quickly after cytoplasm loosing. After injection, the zygotes were transferred to a Petri dish containing M16 medium and were then placed at 37° C., 5% carbon dioxide for 0.5 to 1.0-hour to recover.

The injected zygotes were then transplanted into the pseudopregnant recipient. About 19-21 days after the transplantation, the rats born were the F0 rats. The results are summarized in Table 1 below.

TABLE 1

|   | Strain | No. of Zygotes | No. of pups | No. of founder |
|---|--------|----------------|-------------|----------------|
| 1 | SD | 60 | 10 | 1 female |
| 2 | SD | 131 | 24 | 0 |

Example 4

Genotyping of the F0 Rats

The F0 rats obtained in Example 3 were sexually matured at an age of about 8 weeks.

Figure 6A:
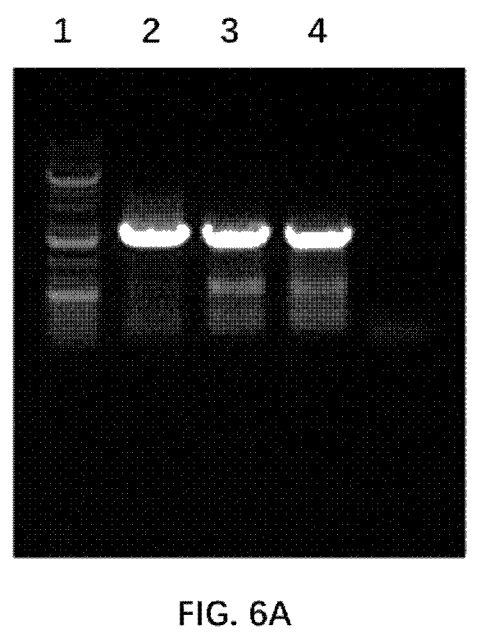
Figure 6B:
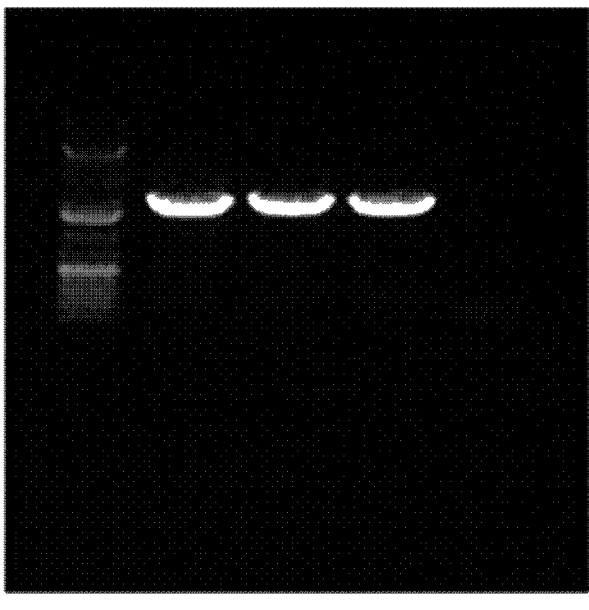

The genotypes of the F0 rats were determined using PCR, and the results for amplifying the 5' junction integration and the 3' junction integration are shown in FIGS. 6A and 6B, respectively. In FIG. 6A, lane 1 was loaded with DNA marker, lane 2 was loaded with 5' junction PCR products from F0 pup No. 7, lane 3 was loaded with 5' junction PCR products from F0 pup No. 27, lane 4 was loaded with 5' junction PCR products from wildtype rat, and lane 5 was loaded with a negative control. In FIG. 6B, lane 1 was loaded with DNA marker, lane 2 was loaded with 3' junction PCR products from F0 pup No. 7, lane 3 was loaded with 3' junction PCR products from F0 pup No. 27, lane 4 was loaded with 3' junction PCR products from wildtype rat, and lane 5 was loaded with a negative control.

These results indicate that F0 pup No. 7 carries the desired chimeric APP gene and was chosen for later experiments.

Example 5

Genotyping of the F1 Rats

Figure 7:
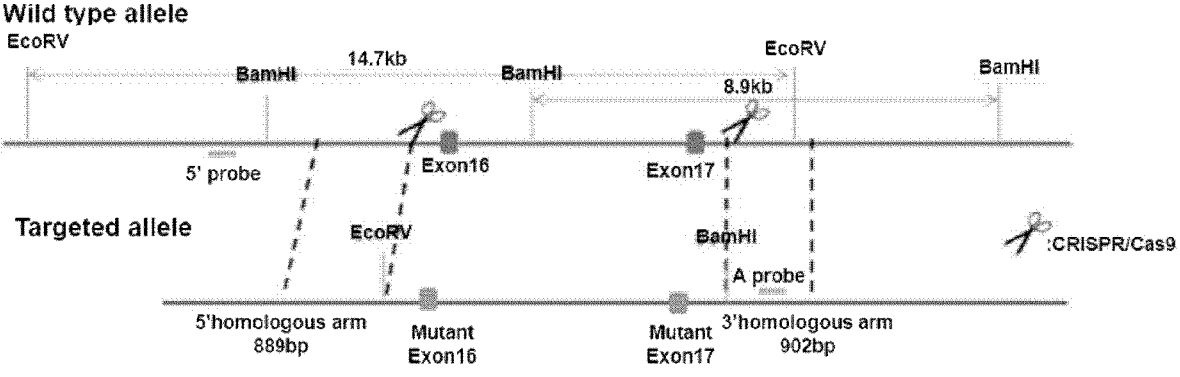
FIG. 7 illustrates a scheme of the knocking-in strategy.

The F0 pup No. 7 obtained in Example 4 was crossed with wildtype RD rats, to obtain F1 rats. To verify the correct recombination in F1 rats, Southern blotting was performed and at the same time 5' Probe and A-Probe was used for further confirmation. A scheme of the gene editing strategy is illustrated in FIG. 7.

Figure 9:
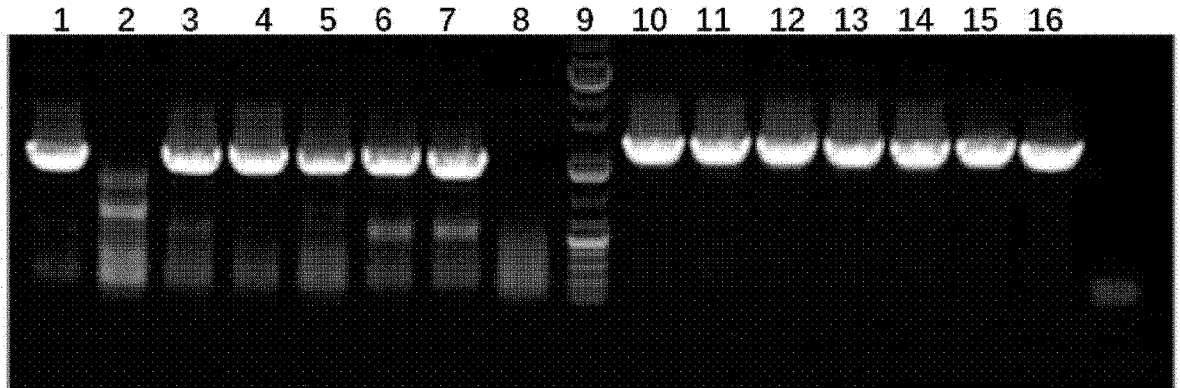
FIG. 9 illustrates results of genotype identification in F1 rats.
Figure 10A:
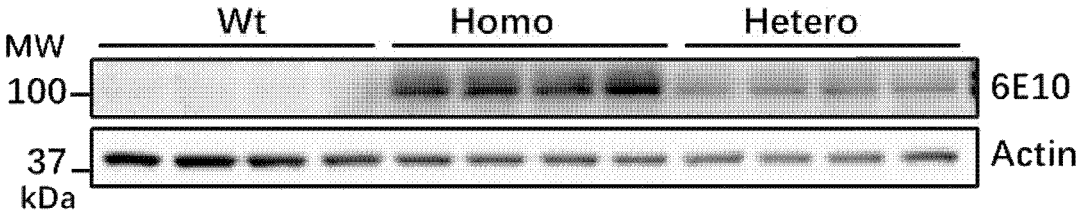
FIGS. 10A-10B illustrate detection of human APP expression.
Figure 10B:
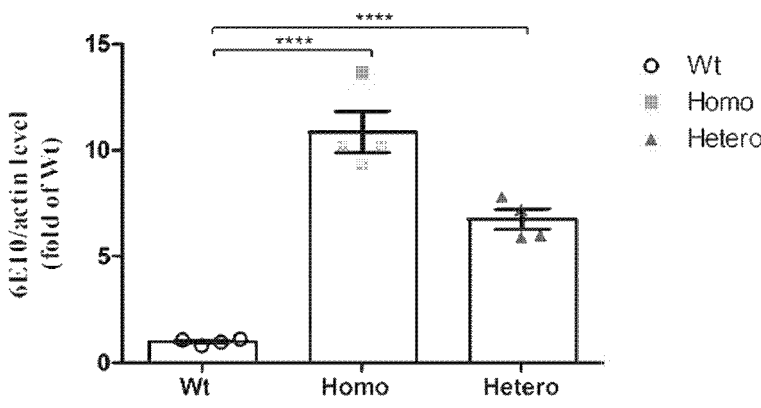
Figure 11:
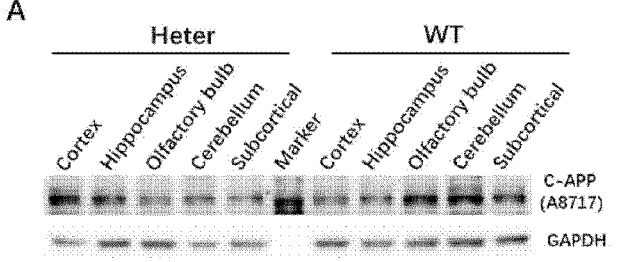
FIGS. 11A-11B illustrate detection of APP expression in different parts of the rats.
Figure 11:
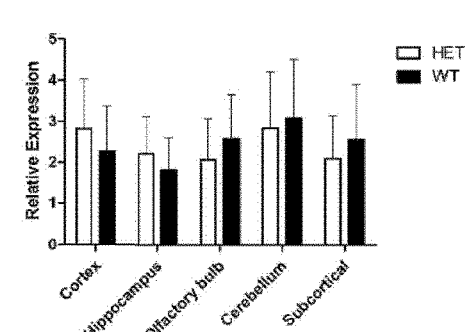
Figure 12:
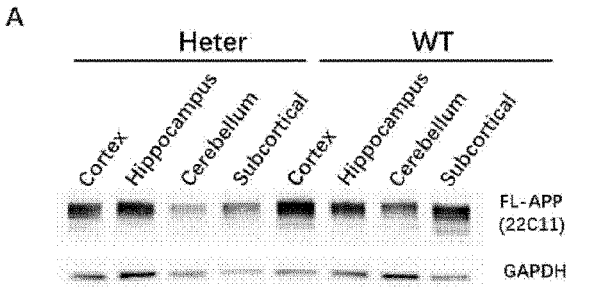
FIGS. 12A-12B illustrate detection of full-length APP expression in different parts of the rats.
Figure 12:
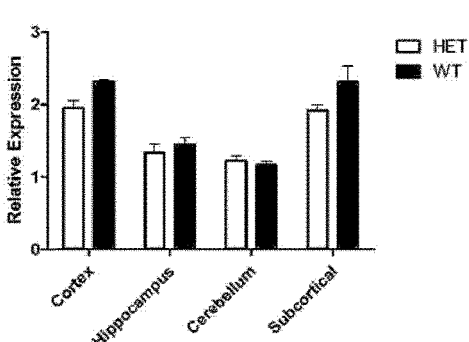
Figure 13:
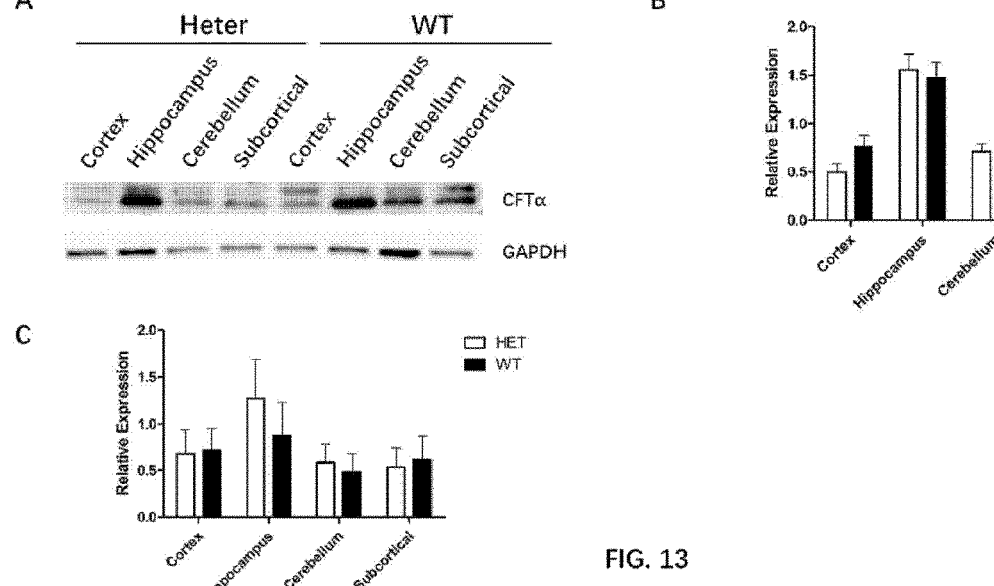
FIGS. 13A-13C illustrate expression of APP-derived fragments.

The genotypes of the F1 rats were determined using PCR, and the results for amplifying the 5' junction integration and the 3' junction integration are shown in FIG. 9. In FIG. 9, lane 1 was loaded with 5' junction PCR products from F1 pup No. 3, lane 2 was loaded with 5' junction PCR products from F1 pup No. 9, lane 3 was loaded with 5' junction PCR products from F1 pup No. 10, lane 4 was loaded with 5' junction PCR products from F1 pup No. 12, lane 5 was loaded with 5' junction PCR products from F1 pup No. 14, lane 6 was loaded with a positive control, lane 7 was loaded with 5' junction PCR products from a wildtype rat, lane 8 was loaded with blank control, lane 9 was loaded with a DNA marker, lane 10 was loaded with 3' junction PCR products from F1 pup No. 3, lane 11 was loaded with 3' junction PCR products from F1 pup No. 9, lane 12 was loaded with 3' junction PCR products from F1 pup No. 10, lane 13 was loaded with 3' junction PCR products from F1 pup No. 12, lane 14 was loaded with 3' junction PCR products from F1 pup No. 14, lane 15 was loaded with a positive control, lane 16 was loaded with 3′ junction PCR products from a wildtype rat, and lane 17 was loaded with blank control.

The genotypes of the F1 rats were also examined using Southern blot. Briefly, genomic DNA was obtained from the F1 rats, digested with EcoRV and BamH1 respectively, and the digestion products were examined using Southern blot. The expected products are shown in Table 2 below.

TABLE 2

|  | Probe | Wild type | Targeted |
|---|---|---|---|
| EcoRV | 5′ | 14.7kb | 9.8kb |
| BamHI | A | 8.9kb | 5.6kb |

Figure 8:
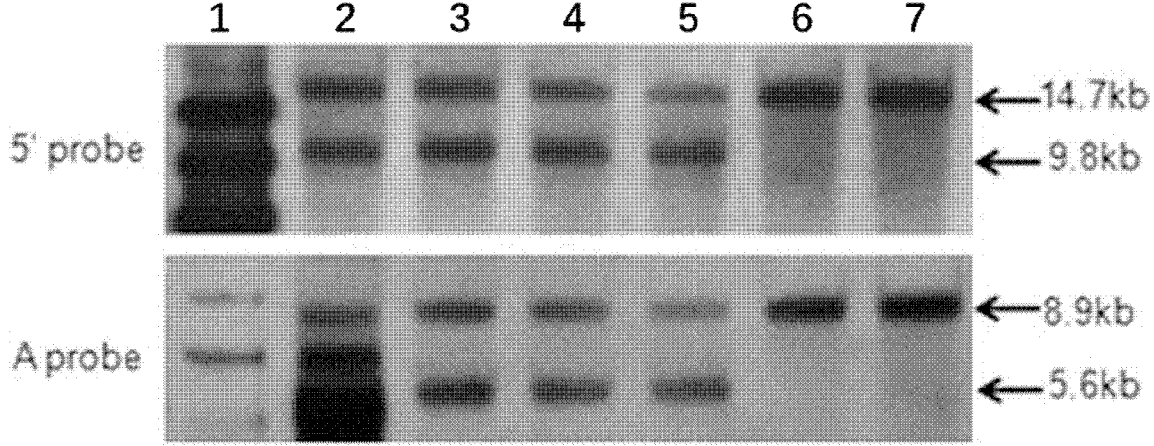
FIG. 8 illustrates results of genotype identification in F1 rats by Southern Blot.

The results of Southern blot analysis are shown in FIG. 8. Lane 1 shows the DNA marker, lane 2 shows the result from F1 pup No. 3, lane 3 shows the result from F1 pup No. 10, lane 4 shows the result from F1 pup No. 12, lane 5 shows the result from F1 pup No. 14, lane 6 and lane 7 show the result from wildtype rat. It can be seen that F1 pup No. 10 and F1 pup No. 12 were the knock-in rats desired (i.e., carrying the desired chimeric App gene).

Example 6

Examining Expression of APP and APP-Derived Fragments in the Knock-In Rats

Western Blotting was used to detect the expression of human App in the knock-in rats obtained in Example 5 (i.e., the F1 rats). Briefly, brain tissues of the rats were homogenized in RIPA (50 mM Tris HCl pH 8.0, 150 mM NaCl, 1% NP-40, 0.5% sodium deoxycholate, CA630, 1% EDTA, 0.1% SDS) buffer with protease inhibitors (Roche Diagnostics). Tissue debris was isolated and discarded by centrifugation at 14,000 r.p.m. for 15 min. Lysates were quantitated using BCA protein assay kit (Thermo Fisher) and equal amounts of protein were loaded on a SDS-PAGE gels. Protein was transferred from acrylamide gels to PVDF membranes (Immobilon-P, Millipore) at 90V for 100 min. Membranes were blocked using bovine serum albumin (BSA, 5% w/v) diluted in TBS-T for 1 h. After blocking, membranes were incubated overnight at 4° C. in BSA (2.5% w/v) in TBS-T with the following appropriate primary antibodies: anti-Human Aβ1-12 (6E10, 1:1000, Covance, 39320), anti-APP-CTF (1:1,000, Sigma, A8717), anti-APP N terminus (1:1000, Millipore, 22C11), and anti-β-actin (1:5000, Abcam, ab9485). The next day, the blots were washed three times with TBS-T for 15 min and incubated in the specific secondary antibodies (1:5000, Invitrogen-|Thermo Fisher Scientific, 31462 and 31432) for 1 hr at room temperature under constant agitation. After washing, the membrane was either probed with enhanced chemiluminescence (ECL) Western blotting substrate (Thermo Fisher Scientific, 34080) and with detection of luminescence (Tanon). Signal intensities were quantified using ImageJ and data analyzed using GraphPad.

The results are shown in FIGS. 10A-10B, 11A-11B, 12A-12B and 13A-13C. It can be seen that human APP is expressed in the knock-in rats. In addition, the level of full length APP, as well as its various fragments (such as CTF-α, CTF-β and AICD) was comparable in wildtype rats and the knock-in rats of the present application.

Accordingly, the knock-in rat models of the present application avoided the problem of APP overexpression in transgenic mice models. Moreover, the knock-in rat models of the present application expressed CTF-α, CTF-β and AICD at physiological levels.

Example 7

Examining Aβ Oligomer and Amyloid Plaque Formation in the Knock-In Rats

Aβ oligomer pathology was examined in the knock-in rats obtained in Example 5 (e.g., the F1 rats). Briefly, the rats were perfused with PBS and 4% paraformaldehyde under deep anaesthesia and the brains were post-fixed overnight in 4% paraformaldehyde. Brains were sectioned at 30 μm using a vibratome (Leica). Sections were permeabilized and blocked in PBS containing 0.2% Triton X-100 and 10% normal goat serum at room temperature for 2 h. Sections were incubated with anti-β-Amyloid antibody (1:1000, Cell Signaling Technology, 2454), and/or anti-β-Amyloid oligomer antibody (OMAB) (1:1000, Agrisera, AS10932), overnight at 4° C. 1-fluoro-2,5-bis(3-carboxy-4-hydroxystyryl) benzene (FSB) was used for detection of amyloidosis. The next day, the sections were washed 3 times in PBS and exposed to AlexaFluor 647 donkey anti-mouse IgG (1:500, Invitrogen) or Alexa Fluor 594 goat anti-mouse IgG (1:500, Invitrogen) secondary antibodies and cell nuclei visualized with Hoechst 33342 (1:5000, Sigma-Aldrich; 94403). The sections were imaged on an Olympus FluoView FV1000 BX2 upright confocal microscope.

Amyloid plaque formation was examined in the knock-in rats obtained in Example 5 (e.g., the F1 rats). Briefly, the paraffin-embedded and frozen rat brain sections were immunostained using antibodies specific to the N termini of Aβ (Aβ1-X and Aβ3(pE)-X9), the N-terminal region of Aβ (82E1, IBL), Aβ17-24 (4G8, Covance), AβX-40 (IBL), and/or AβX-42 (IBL). The tyramide signal amplification (PerkinElmer Life Sciences) was used, when necessary. 1-fluoro-2,5-bis(3-carboxy-4-hydroxystyryl) benzene (FSB) was used for detection of amyloidosis. Antigen retrieval was performed by autoclave (121° C. for 5 min) for 82E1 and 6E10 staining or by formic acid treatment (90% formic acid for 5 min at 20-25° C.) for immunohistochemistry of 4G8, AβX-40 and AβX-42 antibodies. The immunoreactive areas was calculated using MetaMorph imaging software (Universal Imaging). To reduce the variance among tissue sections, the average of data from at least four sections per mouse was used as an individual value.

Figure 14:
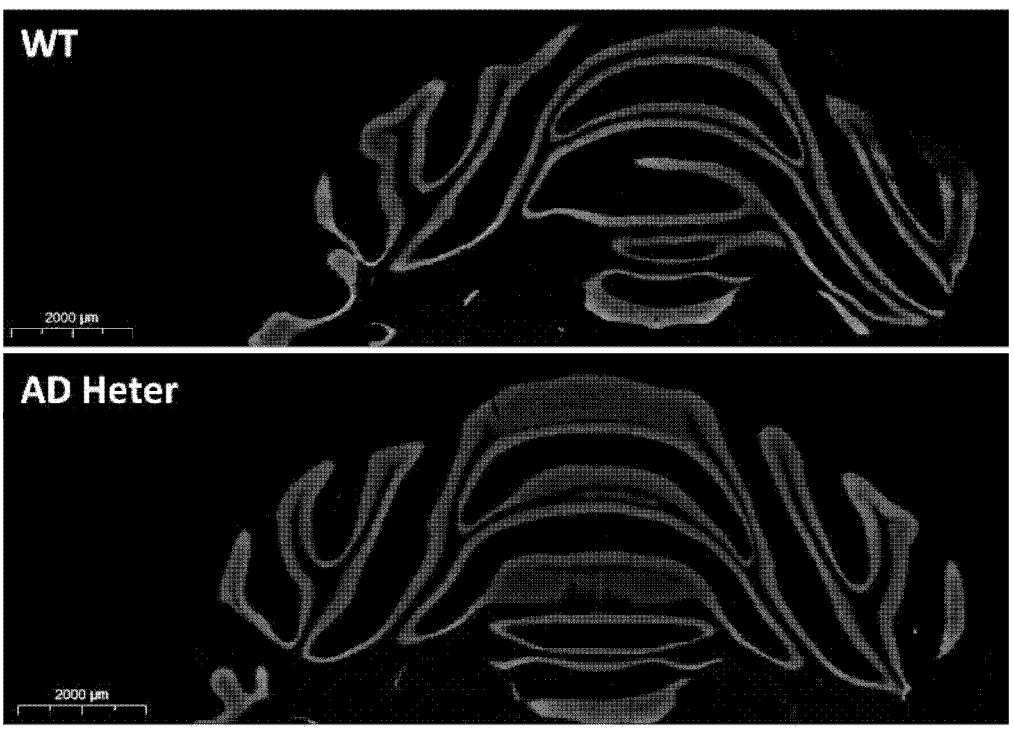
FIG. 14 illustrates lack of Amyloid plaques in the cerebellum of the rats.
Figure 15:
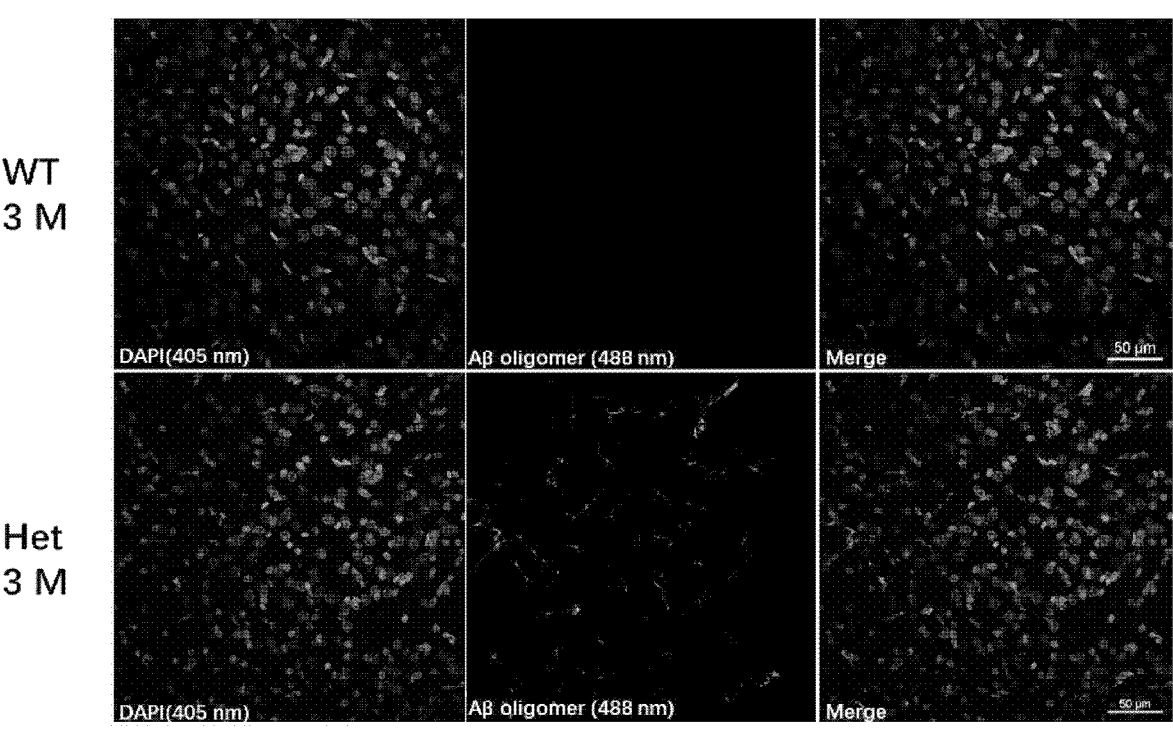
FIG. 15 illustrates Aβ oligomer formation in 3-month old wildtype rats and 3-month old rats of the present disclosure.
Figure 16A:
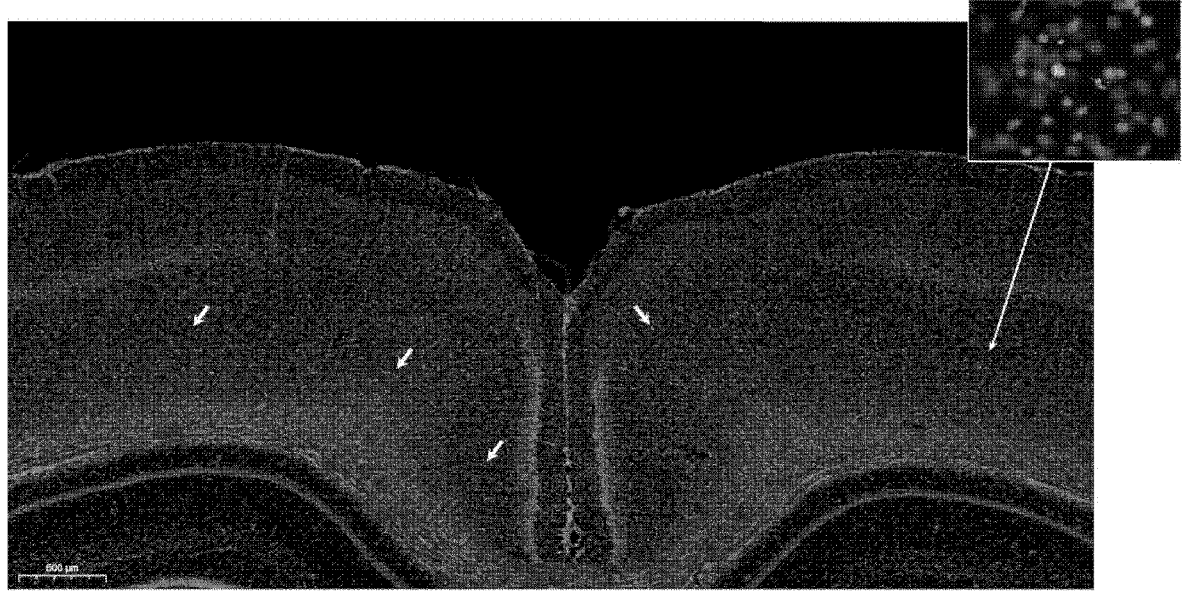
FIG. 16A illustrates Amyloid plaque formation in 4-month old rats of the present disclosure.
Figure 16B:
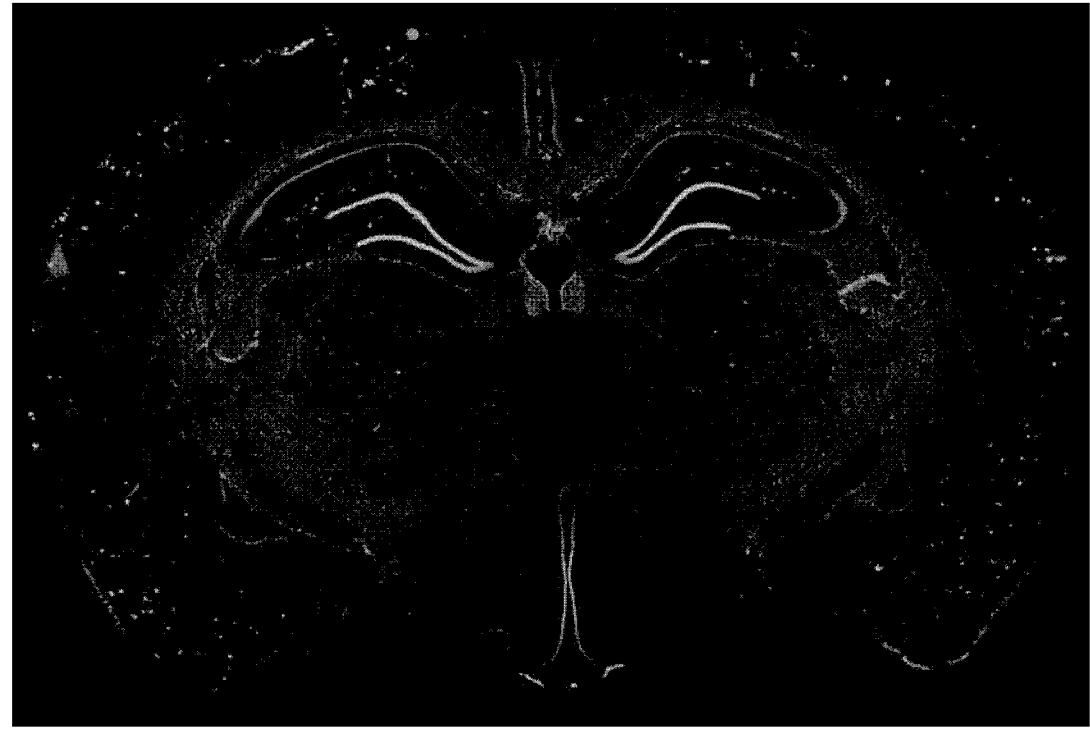
FIG. 16B illustrates Amyloid plaque formation in 6-month old rats of the present disclosure.
Figure 16C:
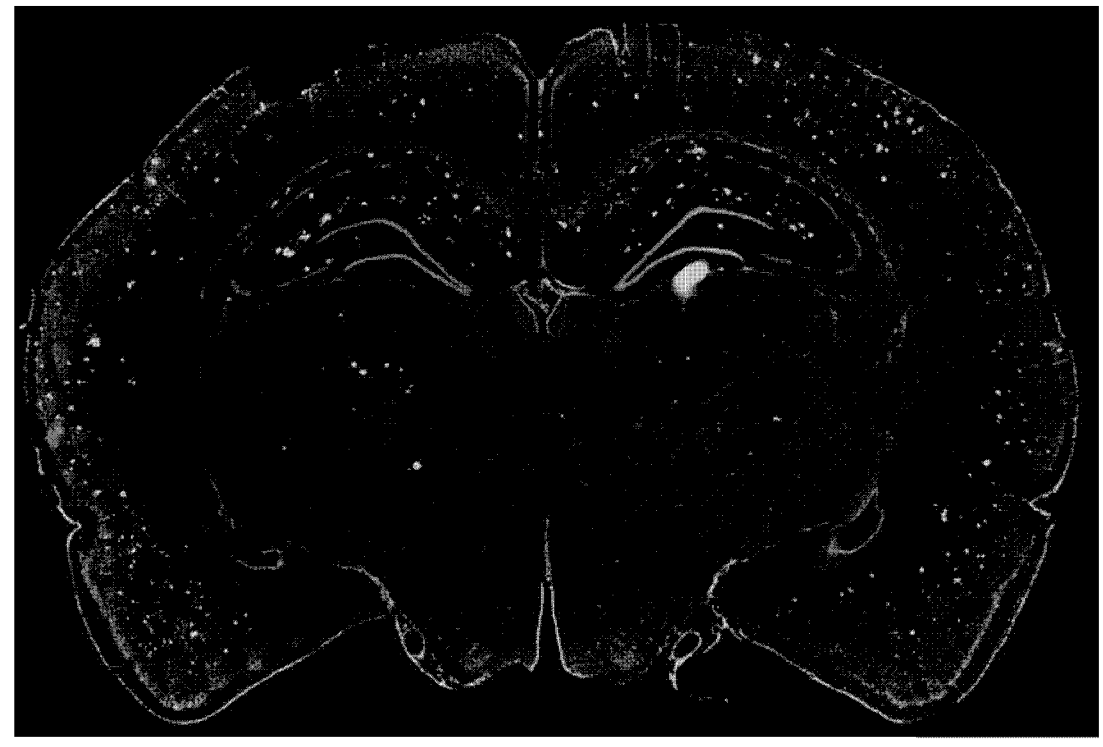
FIG. 16C illustrates Amyloid plaque formation in 10-month old rats of the present disclosure.
Figure 16D:
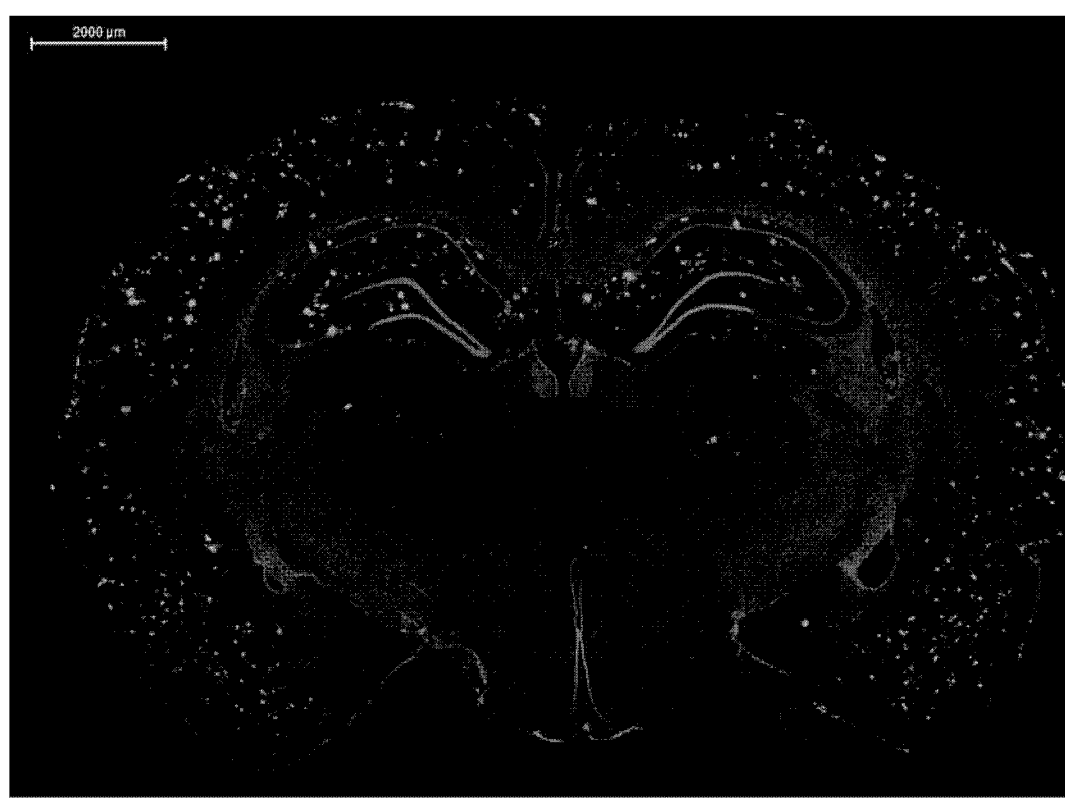
FIG. 16D illustrates Amyloid plaque formation in 14-month old rats of the present disclosure.
Figure 16E:
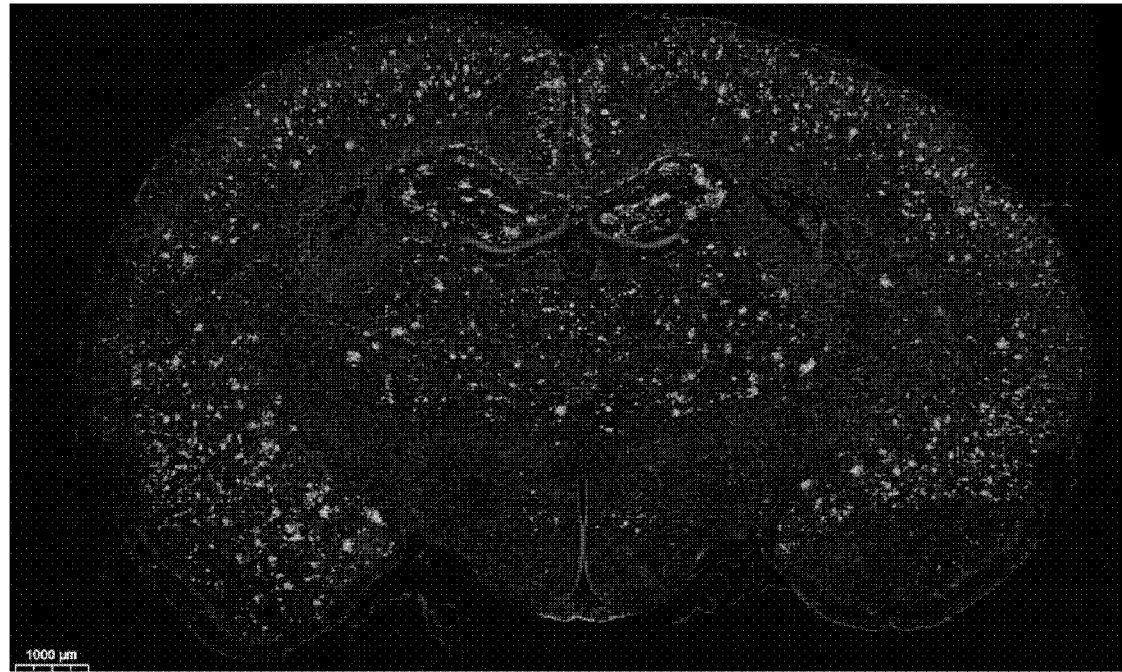
FIG. 16E illustrates Amyloid plaque formation in 22-month old rats of the present disclosure.
Figure 25:
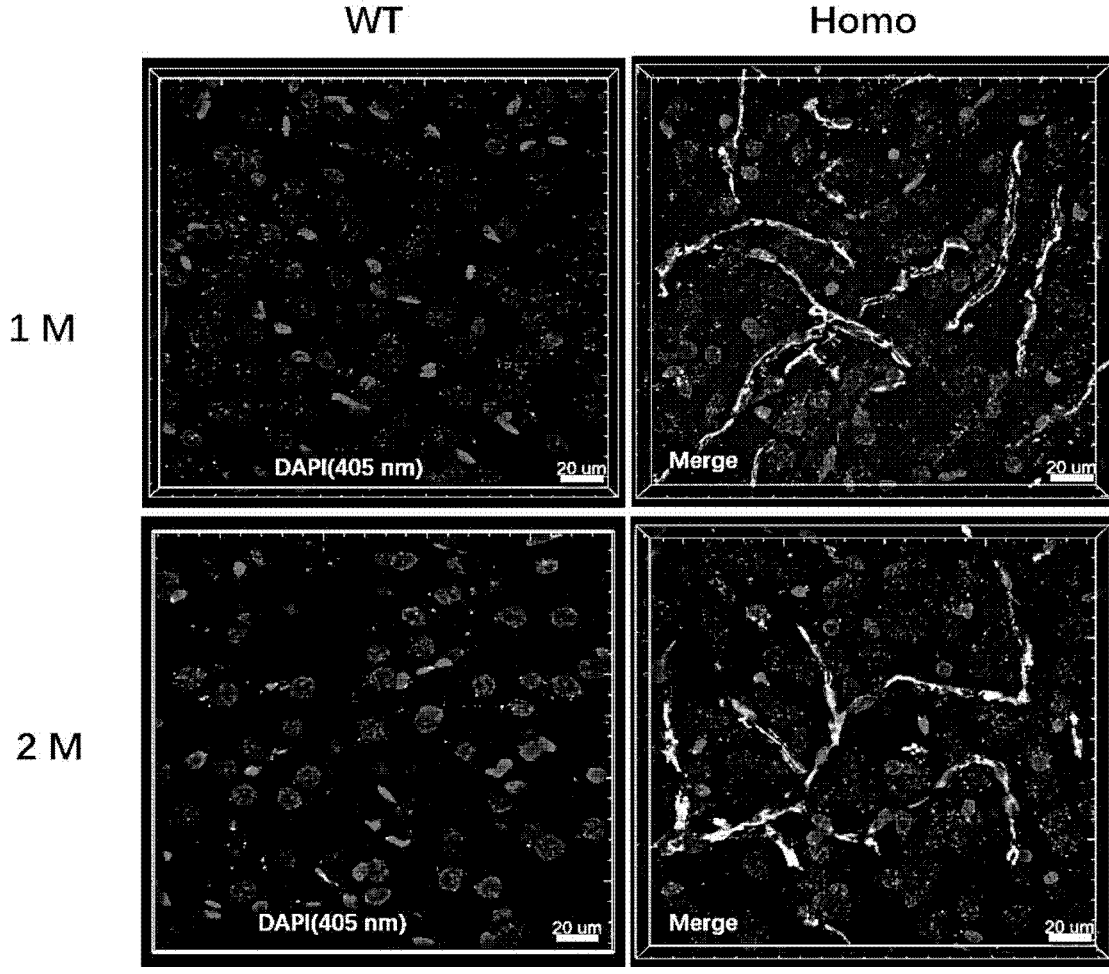
FIG. 25 illustrates Aβ oligomer formation in 1-month old wildtype rats and 1-month old rats of the present disclosure, and in 2-month old wildtype rats and 2-month old rats of the present disclosure.
Figure 26A:
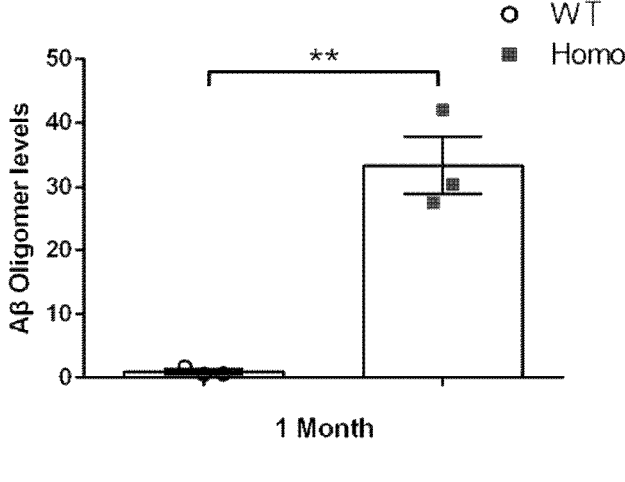
FIG. 26A illustrates Aβ oligomer levels in 1-month old wildtype rats and 1-month old rats of the present disclosure.
Figure 26B:
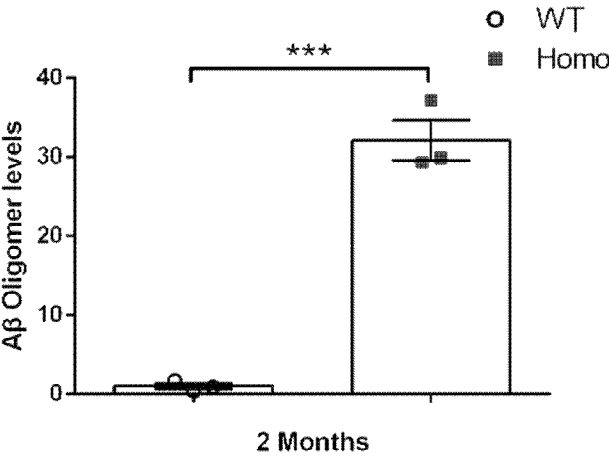
FIG. 26B illustrates Aβ oligomer levels in 2-month old wildtype rats and 2-month old rats of the present disclosure.

The results are shown in FIGS. 14, 15, 16A-16E, 25, 26A-26B, 27A-27F, 28, 29A-29F, 30, 31A-31F, and 32. It can be seen that Amyloid plaque formation was not seen in the cerebellum of the knock-in rat model of the present application (FIG. 14). Moreover, as shown in FIG. 15, Aβ oligomer pathology was detected in the App knock-in rat model of the present disclosure as early as 3-month old (heterozygous for the chimeric App gene). As shown in FIGS. 25 and 26A-26B, Aβ oligomer pathology was detected in the App knock-in rat model of the present disclosure as early as 1-month old when homozygous for the chimeric App gene. As shown in FIGS. 16A-16E and 30, Amyloid plaque formation was detected in the App knock-in rat model of the present disclosure as early as 4-month old (for rats heterozygous for the chimeric App gene), and more plaques were detected at 6 months, 10 months, 12 months, 14 months, 22 months and 36 months, respectively. As shown in FIGS. 27A-27F, Amyloid plaque formation was detected in the App knock-in rat model of the present disclosure as early as 1-month old (FIG. 27A, for rats homozygous for the chimeric App gene), and more plaques were detected at 2 months, 3 months, 6 months, 12 months and 22 months, respectively (FIGS. 27B-27F, for rats homozygous for the chimeric App gene).

Figure 28:
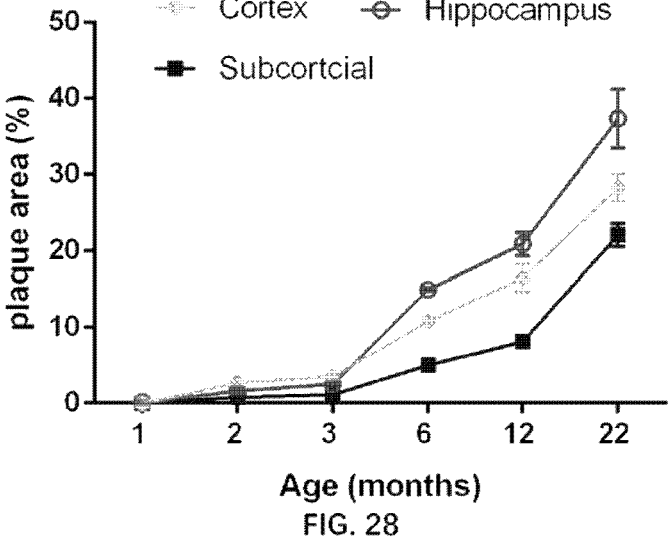
FIG. 28 illustrates Amyloid plaque area in different brain domains of the rats of the present disclosure.

As shown in FIG. 28, for rats of the present disclosure (e.g., when homozygous for the chimeric App gene), distribution of Amyloid plaques at 1-month, 2-month, 3-month, 6-month, 12-month and 22-month in the cortex, the hippocampus and the subcortical regions was consistent with the pattern observed in human AD patients.

Figure 27A:
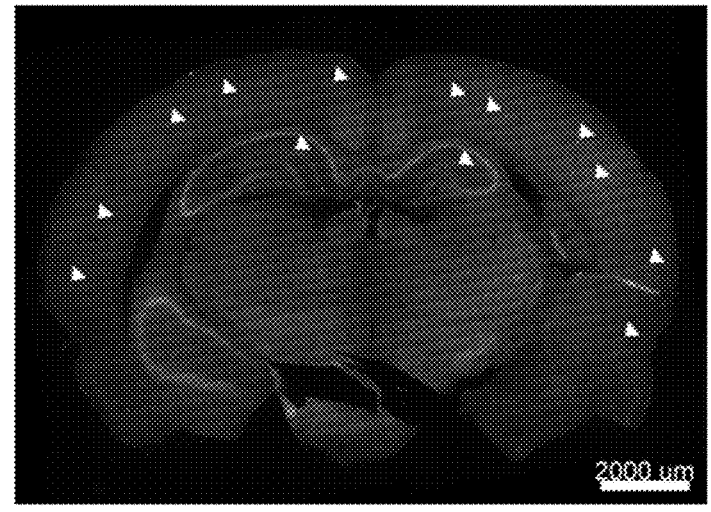
FIG. 27A illustrates Amyloid plaque formation in 1-month old rats of the present disclosure.
Figure 27B:
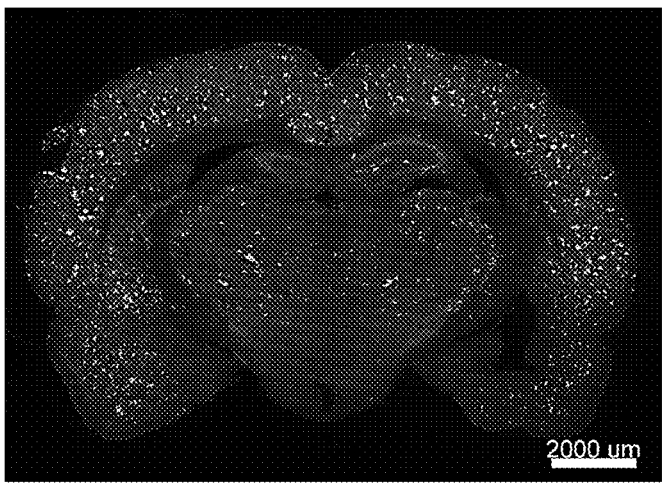
FIG. 27B illustrates Amyloid plaque formation in 2-month old rats of the present disclosure.
Figure 27C:
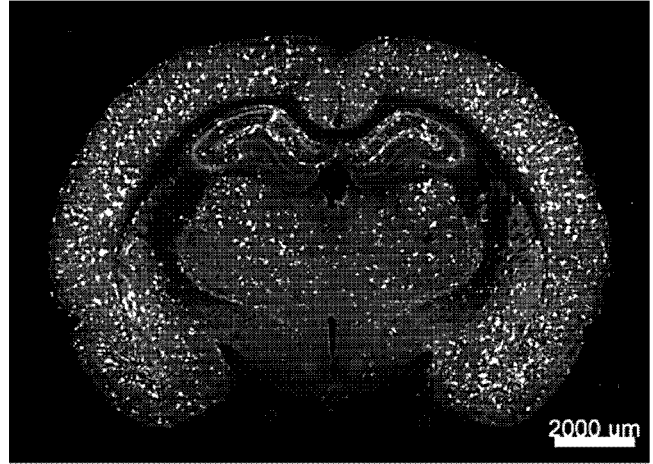
FIG. 27C illustrates Amyloid plaque formation in 3-month old rats of the present disclosure.
Figure 27D:
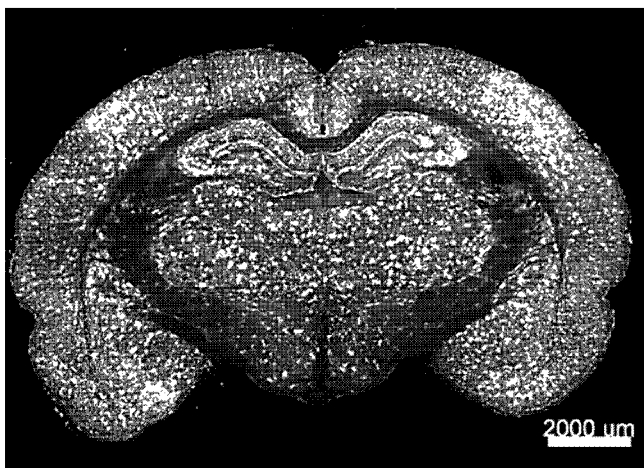
FIG. 27D illustrates Amyloid plaque formation in 6-month old rats of the present disclosure.
Figure 27E:
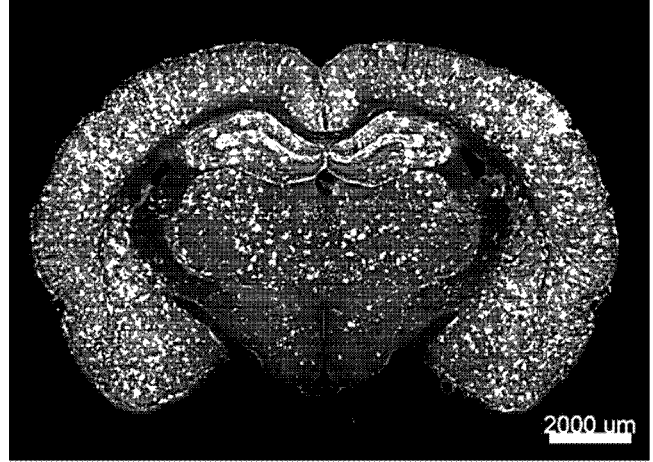
FIG. 27E illustrates Amyloid plaque formation in 12-month old rats of the present disclosure.
Figure 27F:
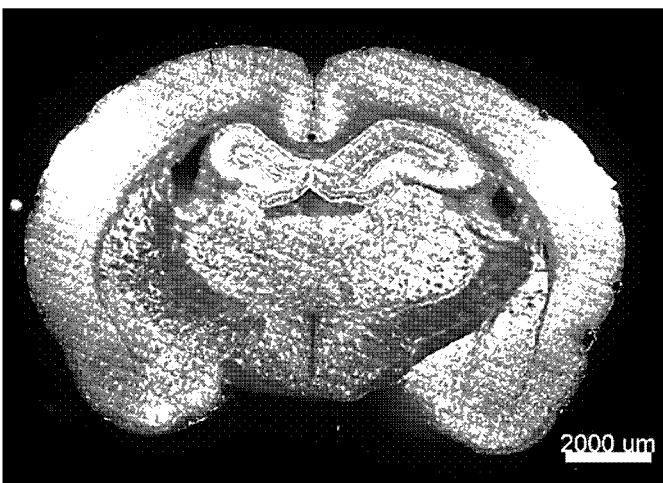
FIG. 27F illustrates Amyloid plaque formation in 22-month old rats of the present disclosure.
Figure 29A:
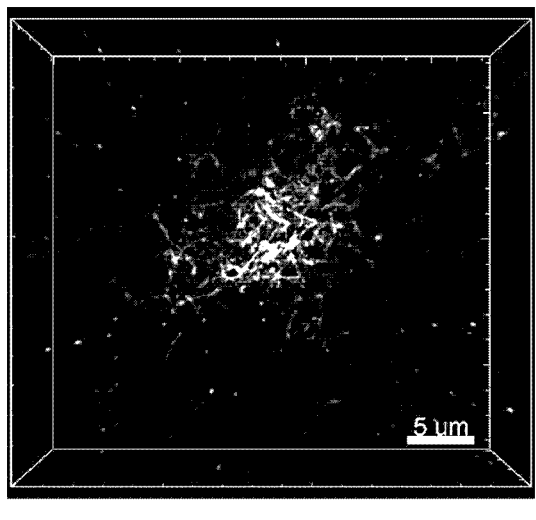
FIG. 29A illustrates super-resolution structure of a single Amyloid plaque in a 1-month old rat of the present disclosure.
Figure 29B:
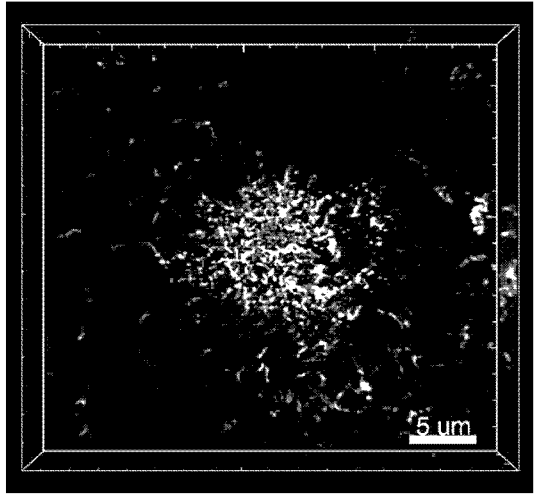
FIG. 29B illustrates super-resolution structure of a single Amyloid plaque in a 2-month old rat of the present disclosure.
Figure 29C:
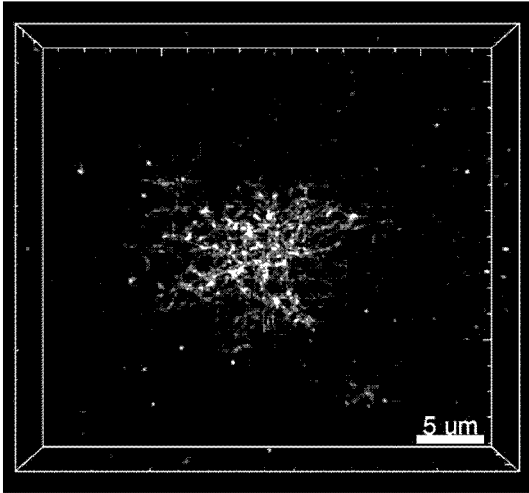
FIG. 29C illustrates super-resolution structure of a single Amyloid plaque in a 3-month old rat of the present disclosure.
Figure 29D:
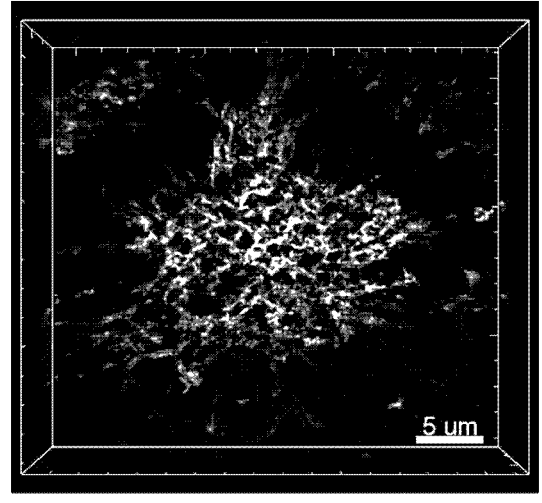
FIG. 29D illustrates super-resolution structure of a single Amyloid plaque in a 6-month old rat of the present disclosure.
Figure 29E:
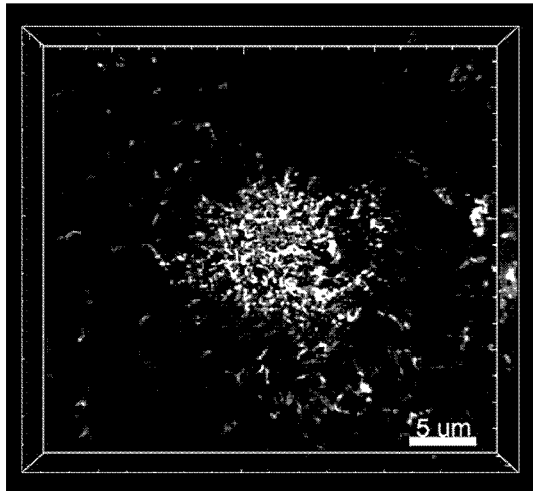
FIG. 29E illustrates super-resolution structure of a single Amyloid plaque in a 12-month old rat of the present disclosure.
Figure 29F:
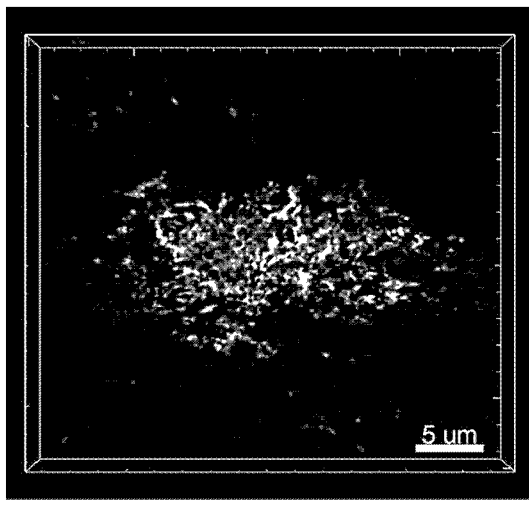
FIG. 29F illustrates super-resolution structure of a single Amyloid plaque in a 22-month old rat of the present disclosure.
Figure 30:
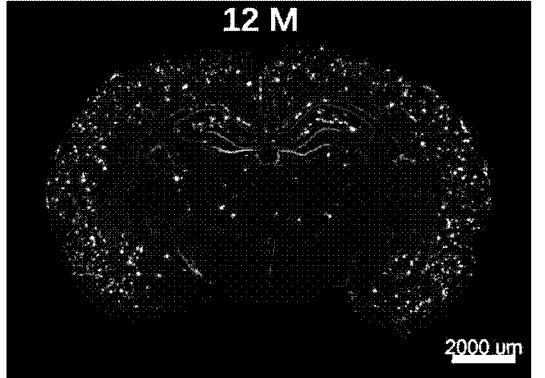
FIG. 30 illustrates Amyloid plaque formation in 12-month old rats of the present disclosure and 36-month old rats of the present disclosure.
Figure 30:
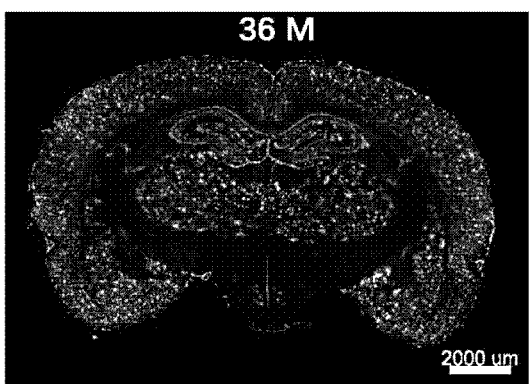
Figure 31A:
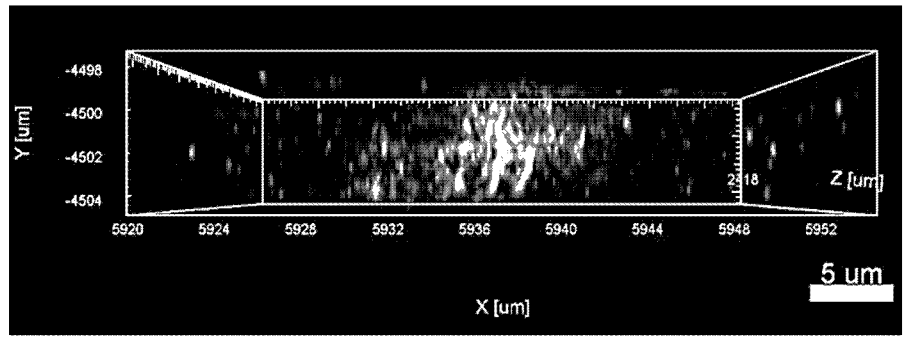
FIG. 31A illustrates the thickness of Amyloid plaque in 1-month old rats of the present disclosure.
Figure 31B:
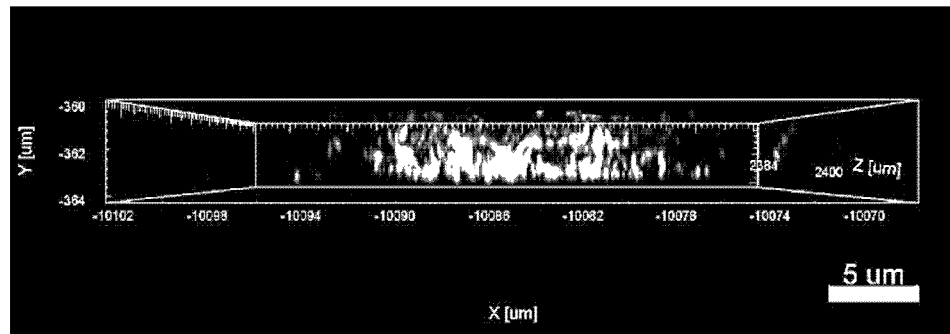
FIG. 31B illustrates the thickness of Amyloid plaque in 2-month old rats of the present disclosure.
Figure 31C:
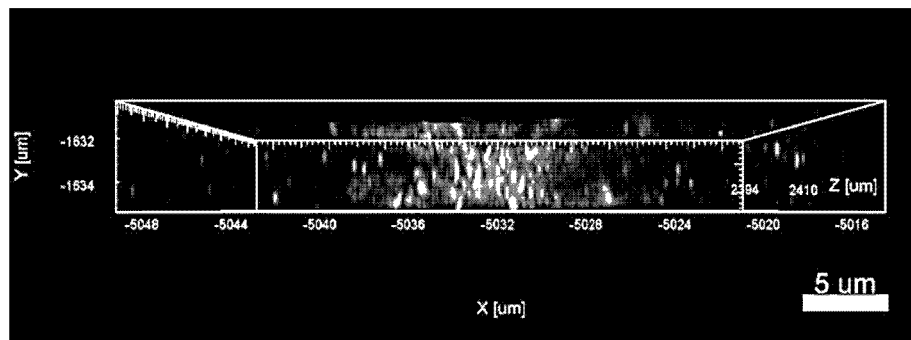
FIG. 31C illustrates the thickness of Amyloid plaque in 3-month old rats of the present disclosure.
Figure 31D:
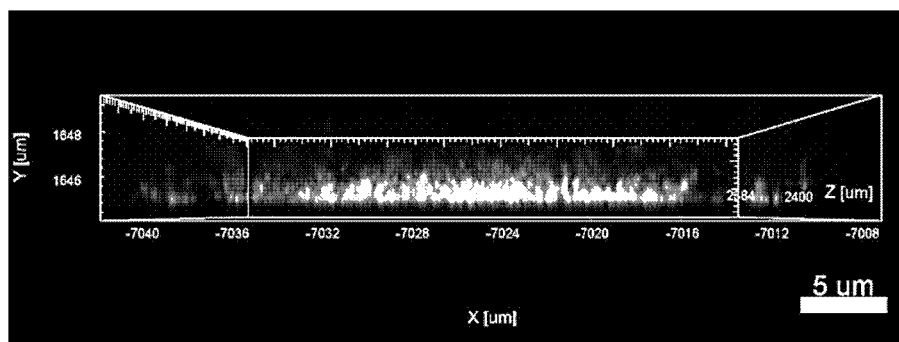
FIG. 31D illustrates the thickness of Amyloid plaque in 6-month old rats of the present disclosure.
Figure 31E:
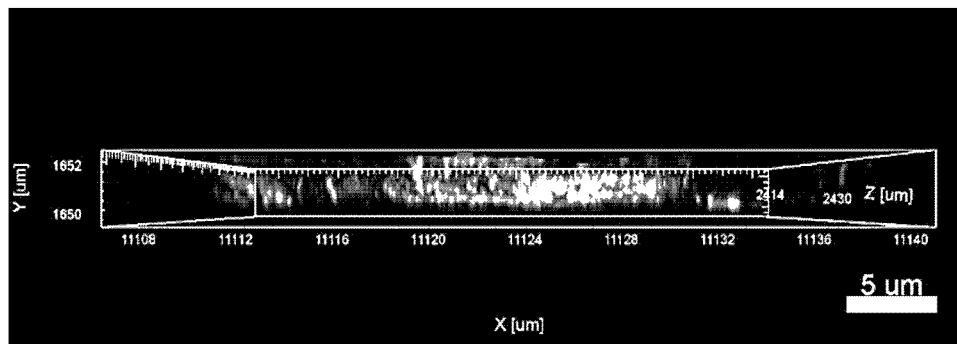
FIG. 31E illustrates the thickness of Amyloid plaque in 12-month old rats of the present disclosure.
Figure 31F:
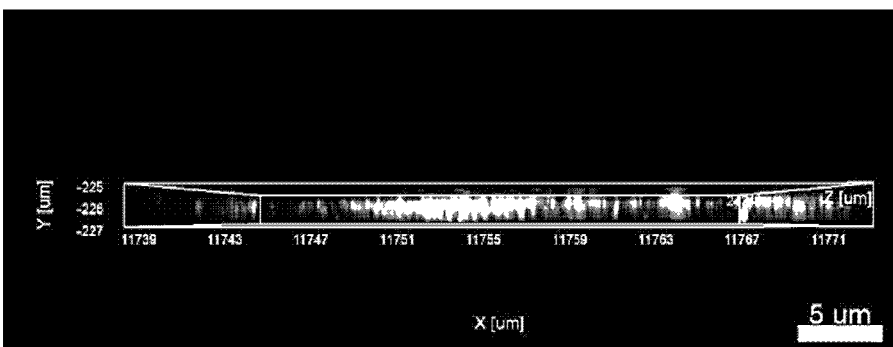
FIG. 31F illustrates the thickness of Amyloid plaque in 22-month old rats of the present disclosure.
Figure 32:
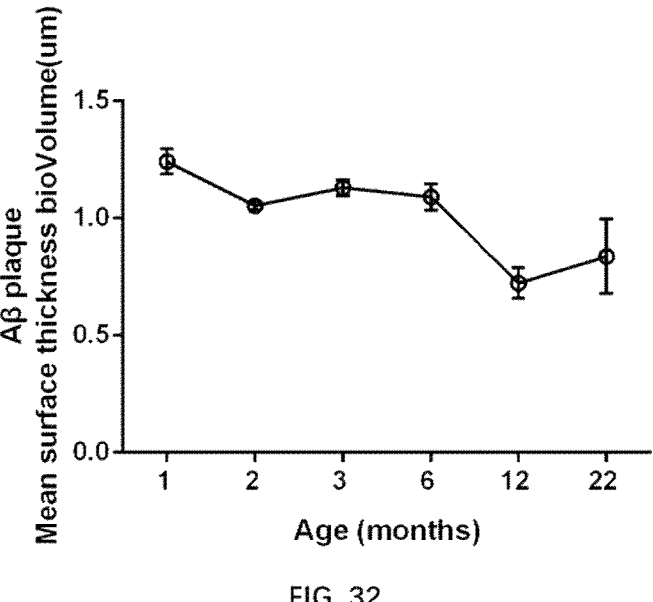
FIG. 32 illustrates mean thickness biovolume of Amyloid plaque in rats of the present disclosure.

FIGS. 29A-27F demonstrate the super-resolution structure of single amyloid plaques from a rat of the present disclosure (e.g., when homozygous for the chimeric App gene) at an age of 1-month, 2-month, 3-month, 6-month, 12-month and 22-month, respectively.

FIGS. 31A-31F and 32 demonstrate change of the thickness and density of the amyloid plaques along with age, in a rat of the present disclosure (e.g., when homozygous for the chimeric App gene) at an age of 1-month, 2-month, 3-month, 6-month, 12-month and 22-month, respectively. It can be seen that the amyloid plaques became thinner and denser when the rat grew older, for example, the amyloid plaques observed at the age of 22-month were significantly denser than those observed at a younger age (e.g., 1-month, 2-month, 3-month, 6-month, or 12-month).

Example 8

Hyper-Phosphorylation of Tau in the Knock-In Rat

Western Blotting was used to examine hyper-phosphorylation of tau in the knock-in rat model obtained in Example 5 (i.e., the F1 rats). Briefly, brain tissue was homogenized in RIPA (50 mM Tris HCl pH 8.0, 150 mM NaCl, 1% NP-40, 0.5% sodium deoxycholate, CA630, 1% EDTA, 0.1% SDS) buffer with protease inhibitors (Roche Diagnostics). Tissue debris was isolated and discarded by centrifugation at 14,000 r.p.m. for 15 min. Lysates were quantitated using BCA protein assay kit (Thermo Fisher) and equal amounts of protein were loaded on a SDS-PAGE gels. Protein was transferred from acrylamide gels to PVDF membranes (Immobilon-P, Millipore) at 90V for 100 min. Membranes were blocked using bovine serum albumin (BSA, 5% w/v) diluted in TBS-T for 1 h. After blocking, membranes were incubated overnight at 4° C. in BSA (2.5% w/v) in TBS-T with the following appropriate primary antibodies: anti-Human PHF-Tau(AT180) (1:500, Thermo Scientific, MN1040), anti-Human PHF-Tau(AT8) (1:500, Thermo Scientific, MN1020), anti-Tau(Tau5), and anti-β-actin (1:5000, Abcam, ab9485). The next day, the blots were washed three times with TBS-T for 15 min and incubated in the specific secondary antibodies (1:5000, Invitrogen/Thermo Fisher Scientific, 31462 and 31432) for 1 hr at room temperature under constant agitation. After washing, the membrane was either probed with enhanced chemiluminescence (ECL) Western blotting substrate (Thermo Fisher Scientific, 34080) and with detection of luminescence (Tanon). Signal intensities were quantified using ImageJ and data analyzed using GraphPad.

Figure 17A:
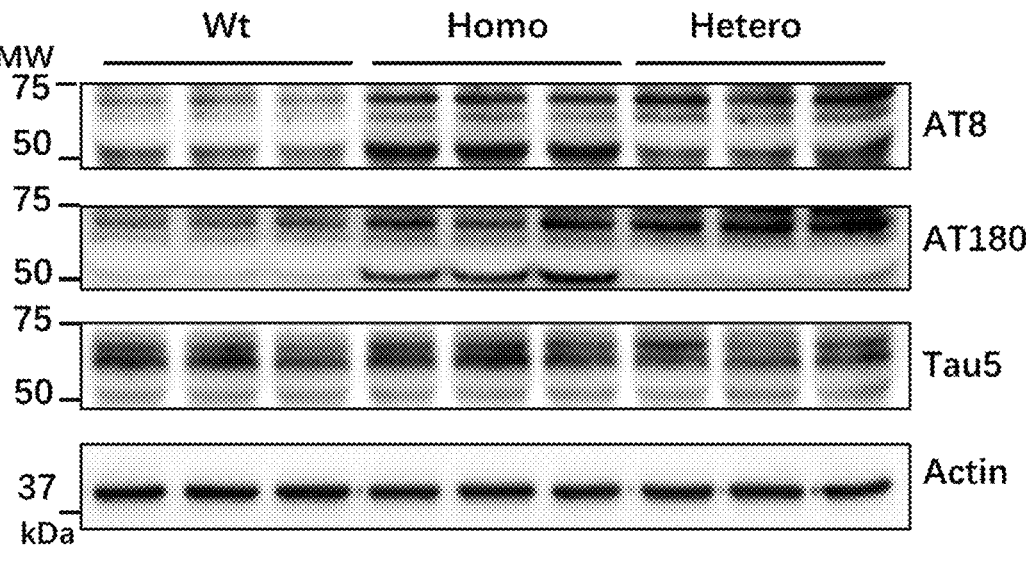
FIGS. 17A-17C illustrate hyper-phosphorylation of tau in wildtype rats and rats of the present disclosure.
Figure 17B:
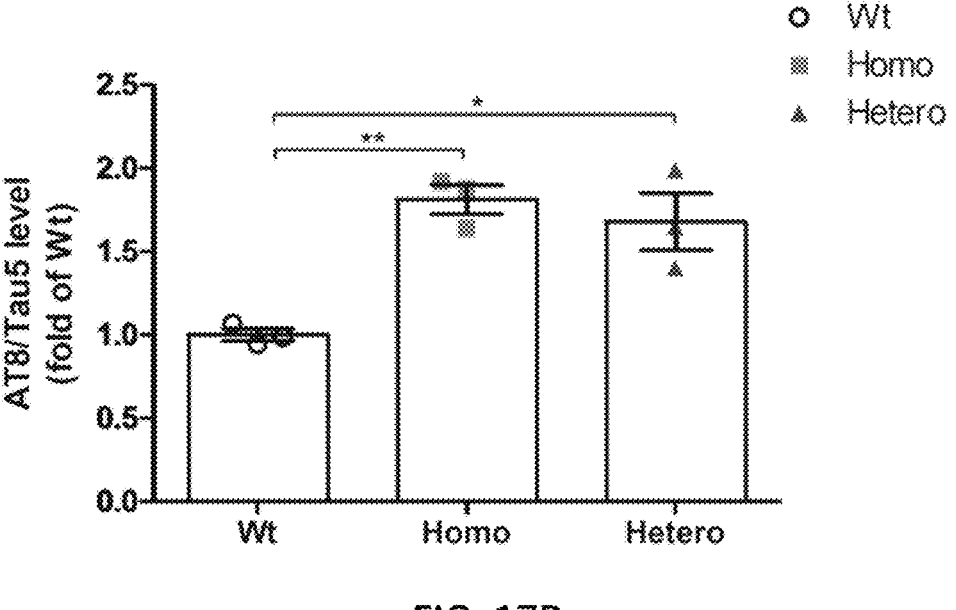
Figure 17C:
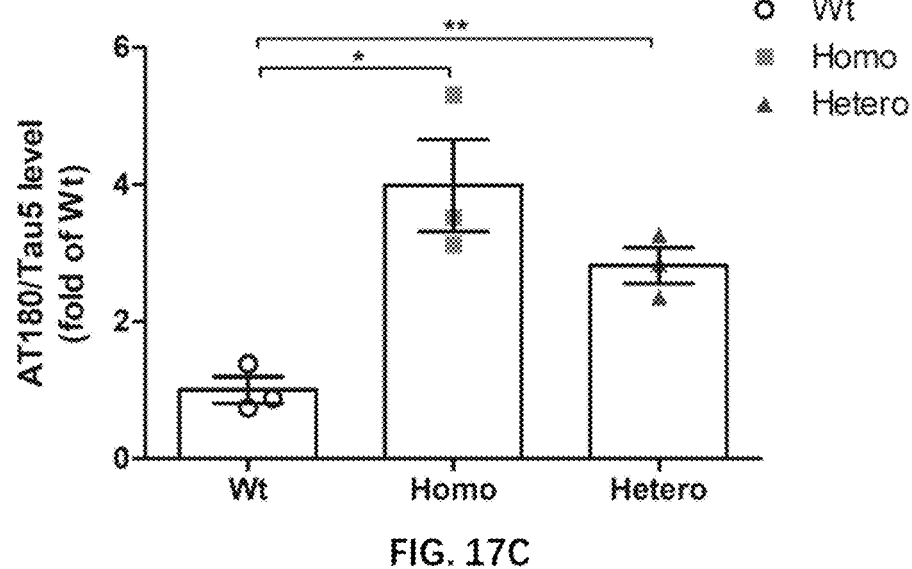
Figure 18A:
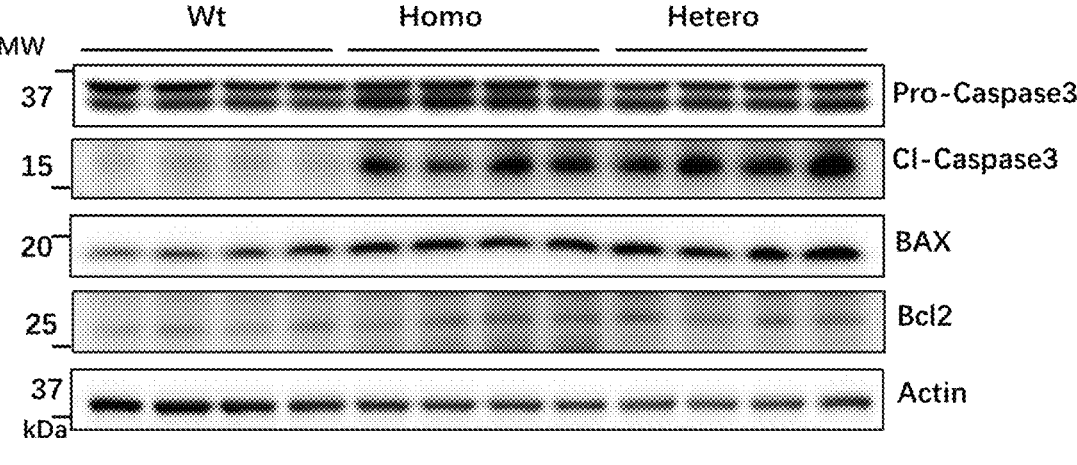
FIGS. 18A-18D illustrate apoptosis in the brain of wildtype rats and rats of the present disclosure.
Figure 18B:
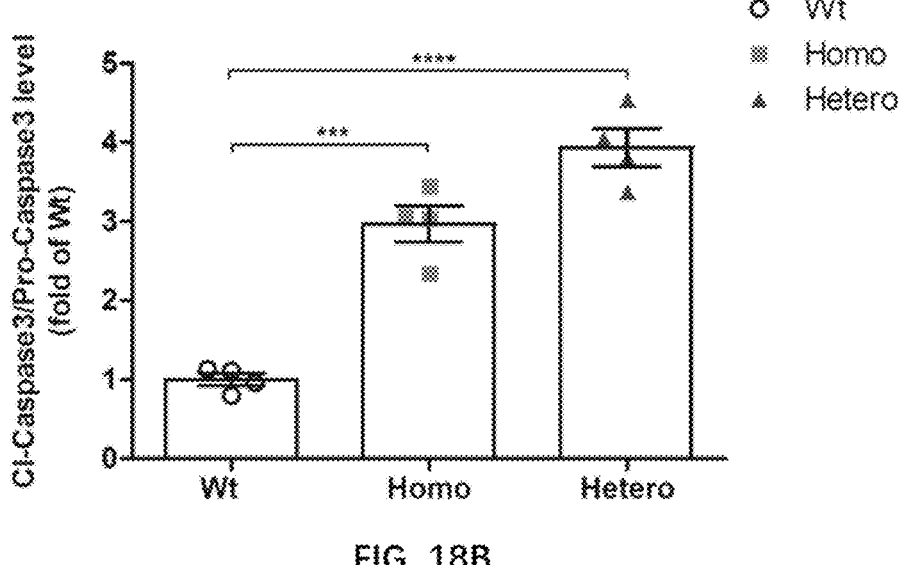
Figure 18C:
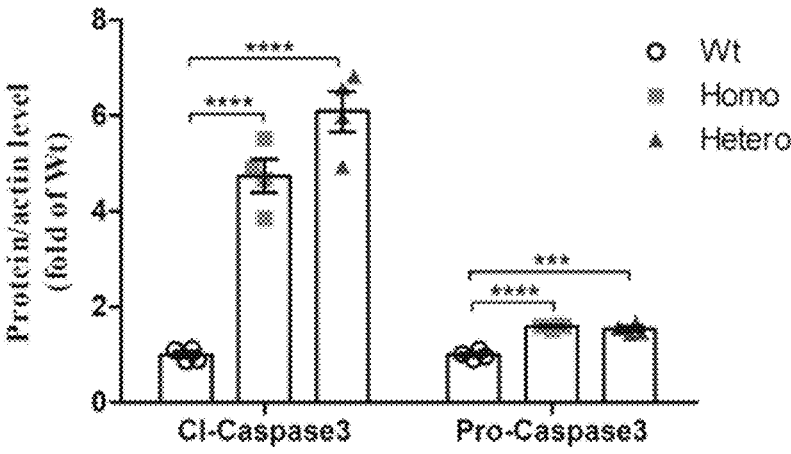
Figure 18D:
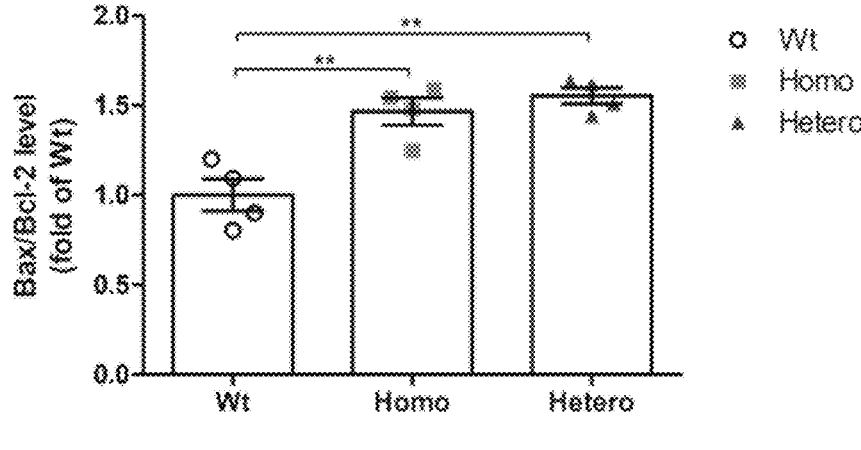
Figure 19A:
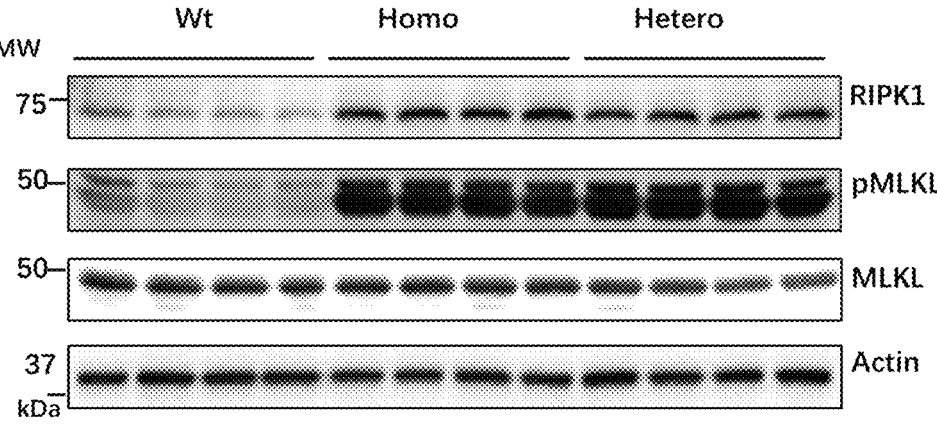
FIGS. 19A-19E illustrate necroptosis in the brain of wildtype rats and rats of the present disclosure.
Figure 19B:
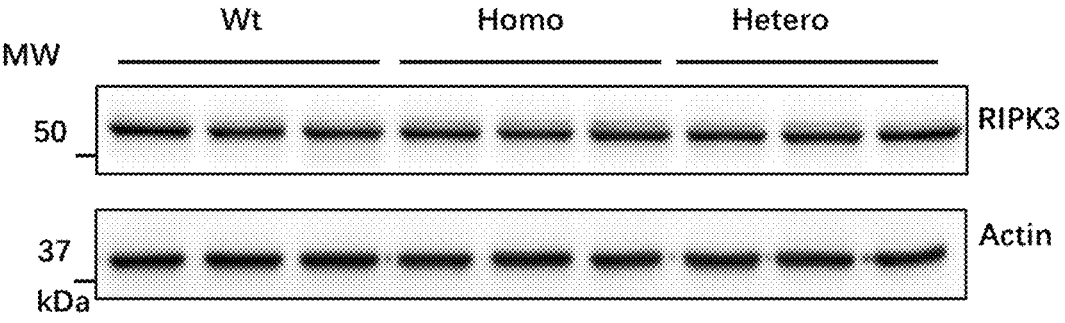
Figure 19C:
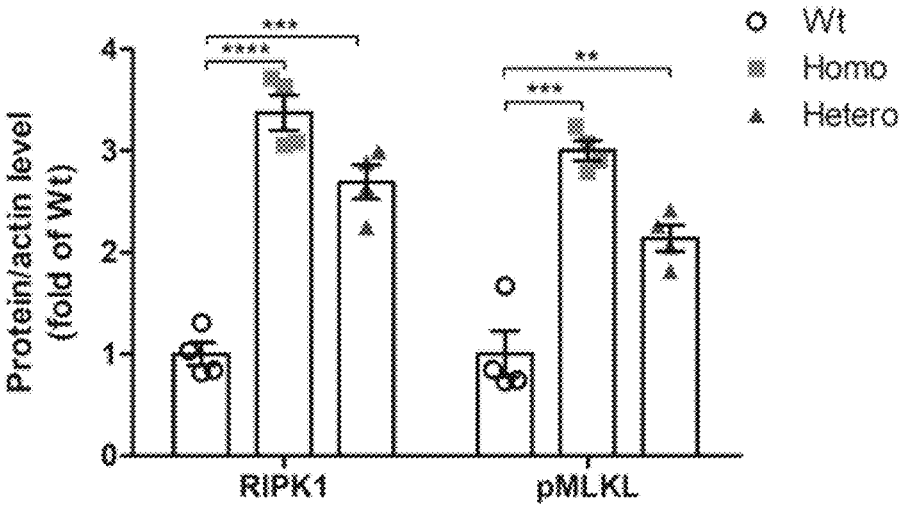
Figure 19D:
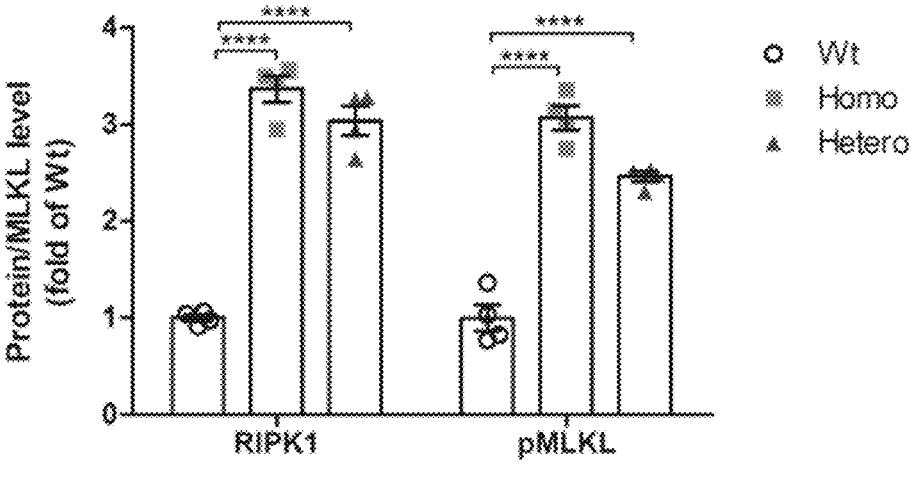
Figure 19E:
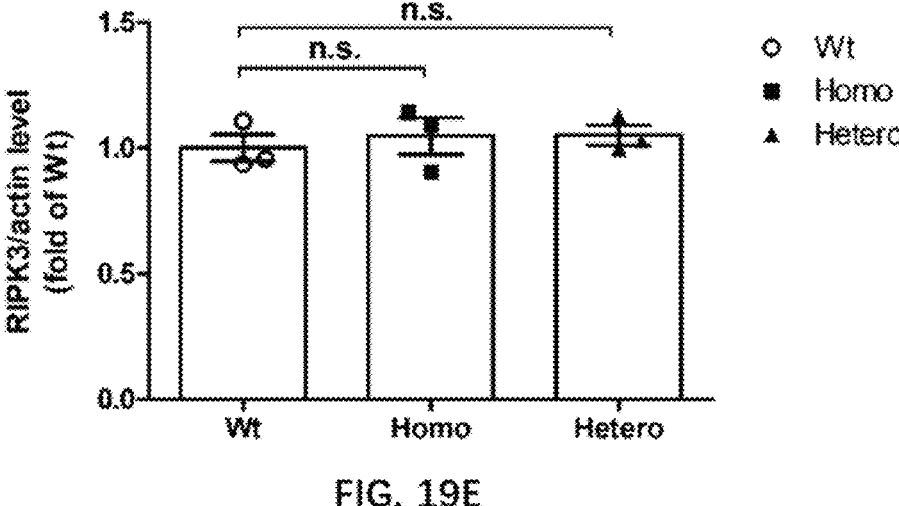
Figure 20A:
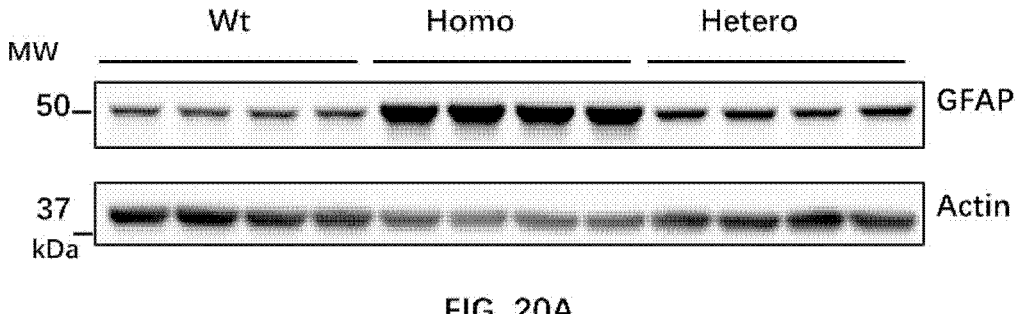
FIGS. 20A-20D illustrate microgliosis and astrocytosis in the brain of wildtype rats and rats of the present disclosure.
Figure 20B:
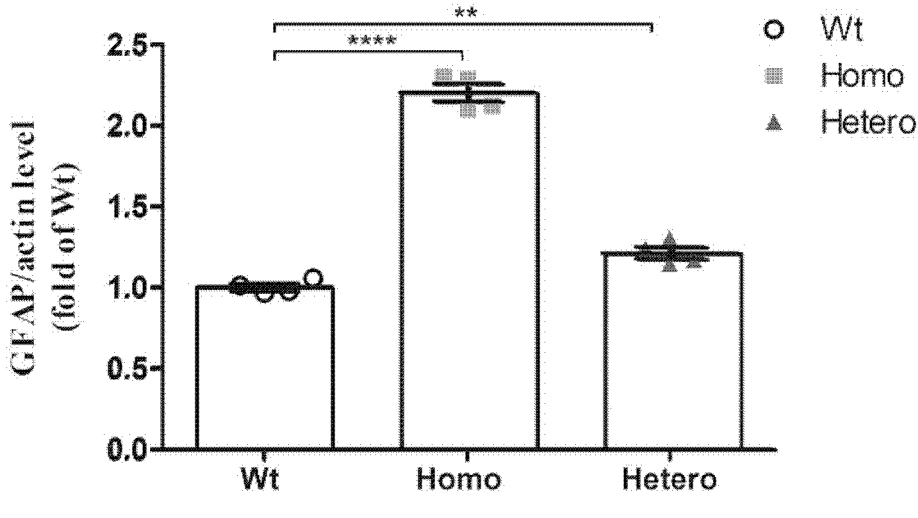
Figure 20C:
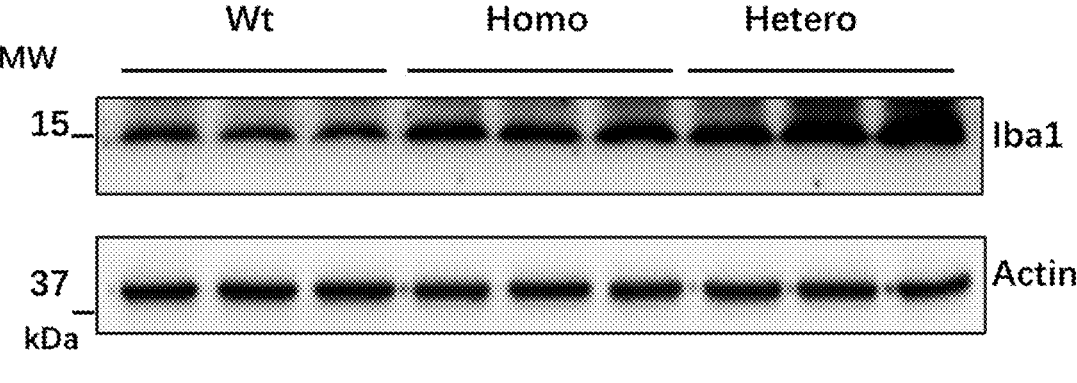
Figure 20D:
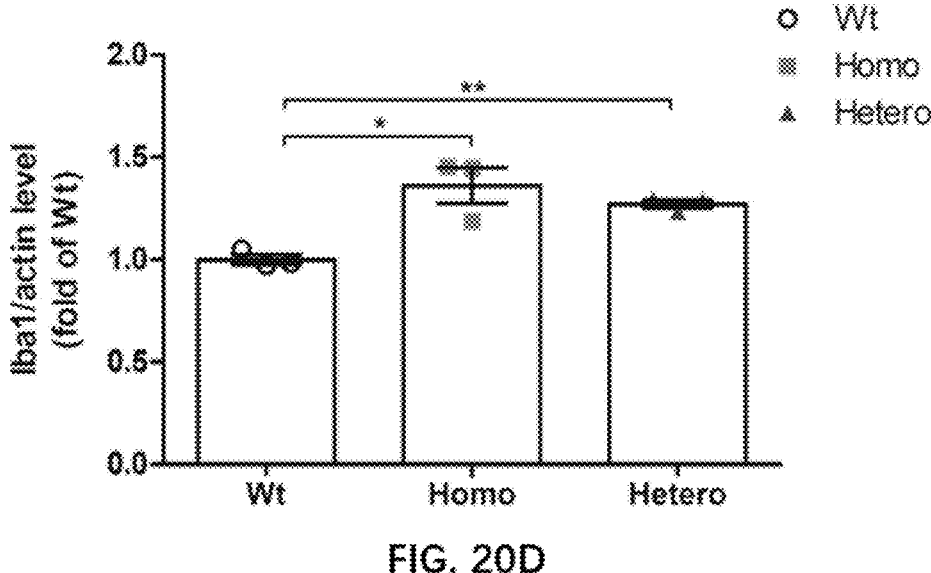
Figure 21:
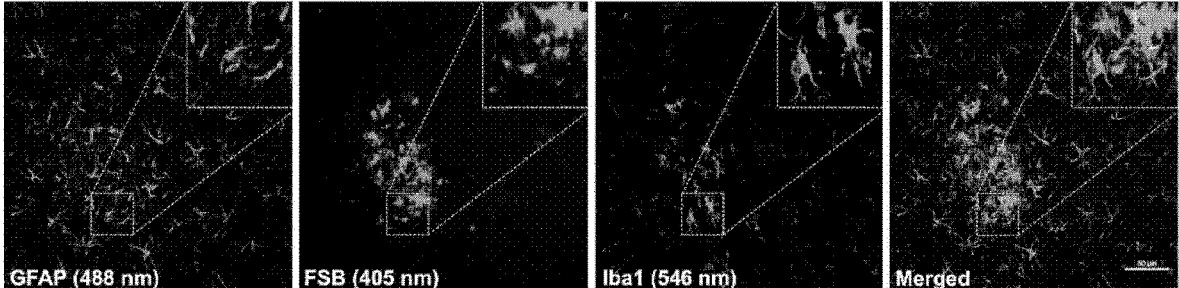
FIG. 21 illustrates association of microgliosis and astrocytosis with Amyloid plaques in the brain of the rats of the present disclosure.
Figure 22:
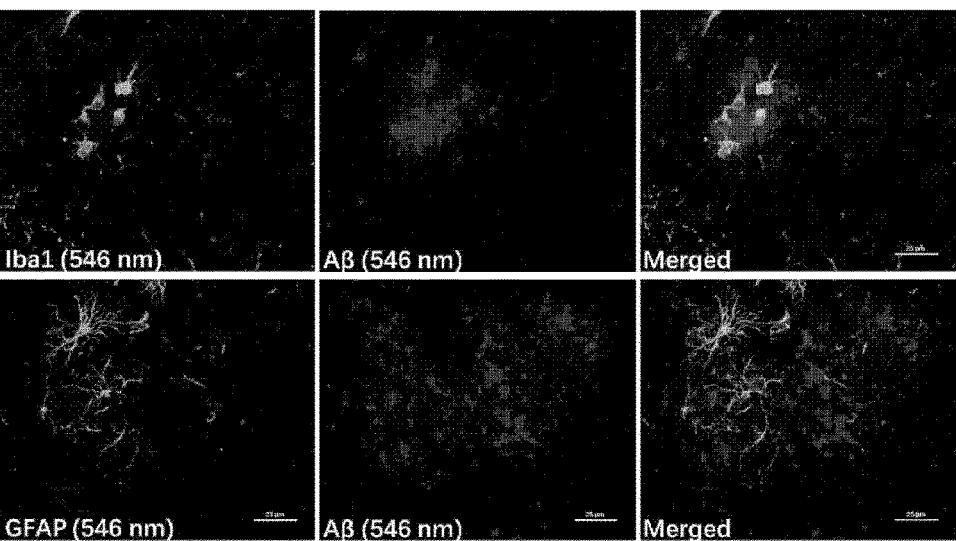
FIG. 22 illustrates association of microgliosis and astrocytosis with Amyloid plaques in the brain of the rats of the present disclosure.

The results are shown in FIGS. 17A-17C. It can be seen that in the knock-in rats (brain, 12 months) of the present disclosure, increased phosphorylation of Thr231 (detected by AT180 antibody) and Ser202 (by AT8 antibody) on tau protein was observed.

Example 9

Apoptosis in the Brain of the Knock-In Rat

Western Blotting was used to examine apoptosis of neuronal cells in the knock-in rat model obtained in Example 5 (i.e., F1 rats). Briefly, brain tissue was homogenized in RIPA (50 mM Tris HCl pH 8.0, 150 mM NaCl, 1% NP-40, 0.5% sodium deoxycholate, CA630, 1% EDTA, 0.1% SDS) buffer with protease inhibitors (Roche Diagnostics). Tissue debris was isolated and discarded by centrifugation at 14,000 r.p.m. for 15 min. Lysates were quantitated using BCA protein assay kit (Thermo Fisher) and equal amounts of protein were loaded on a SDS-PAGE gels. Protein was transferred from acrylamide gels to PVDF membranes (Immobilon-P, Millipore) at 90V for 100 min. Membranes were blocked using bovine serum albumin (BSA, 5% w/v) diluted in TBS-T for 1 h. After blocking, membranes were incubated overnight at 4° C. in BSA (2.5% w/v) in TBS-T with the following appropriate primary antibodies: anti-Caspase3 (1:1000, Cell Signaling Technology, 9665s), anti-Bax (1:1000, Abcam, ab196436), anti-Bcl-2 (1:500, Stata Crus, 7382), and anti-β-actin (1:5000, Abcam, ab9485). The next day, the blots were washed three times with TBS-T for 15 min and incubated in the specific secondary antibodies (1:5000, Invitrogen/Thermo Fisher Scientific, 31462 and 31432) for 1 hr at room temperature under constant agitation. After washing, the membrane was either probed with enhanced chemiluminescence (ECL) Western blotting substrate (Thermo Fisher Scientific, 34080) and with detection of luminescence (Tanon). Signal intensities were quantified using ImageJ and data analyzed using GraphPad.

The results are shown in FIGS. 18A-18D. It can be seen that in the knock-in rats of the present disclosure, the apoptosis makers such as Bax/Bcl-2 and Cl-caspase-3/Pro-caspase3, were increased significantly compared to corresponding wildtype rats. These results indicate neuronal loss in the knock-in rats of the present disclosure.

Example 10

Necroptosis in the Brain of the Knock-In Rats

Western Blotting was used to examine necroptosis of neuronal cells in the knock-in rat model obtained in Example 5 (i.e., F1 rats). Briefly, brain tissue was homogenized in RIPA (50 mM Tris HCl pH 8.0, 150 mM NaCl, 1% NP-40, 0.5% sodium deoxycholate, CA630, 1% EDTA, 0.1% SDS) buffer with protease inhibitors (Roche Diagnostics). Tissue debris was isolated and discarded by centrifugation at 14,000 r.p.m. for 15 min. Lysates were quantitated using BCA protein assay kit (Thermo Fisher) and equal amounts of protein were loaded on a SDS-PAGE gels. Protein was transferred from acrylamide gels to PVDF membranes (Immobilon-P, Millipore) at 90V for 100 min. Membranes were blocked using bovine serum albumin (BSA, 5% w/v) diluted in TBS-T for 1 h. After blocking, membranes were incubated overnight at 4° C. in BSA (2.5% w/v) in TBS-T with the following appropriate primary antibodies: anti-RIPK1 (1:1,000, BD Biosciences, 610459), anti-RIPK3 (1:500, Stata Crus, 374639), anti-MLKL (1:1000, EnoGene, E2A7412), anti-pMLKL (1:1000, Abcam, ab196436), anti-β-actin (1:5000, Abcam, ab9485). The next day, the blots were washed three times with TBS-T for 15 min and incubated in the specific secondary antibodies (1:5000, Invitrogen Thermo Fisher Scientific, 31462 and 31432) for 1 hr at room temperature under constant agitation. After washing, the membrane was either probed with enhanced chemiluminescence (ECL) Western blotting substrate (Thermo Fisher Scientific, 34080) and with detection of luminescence (Tanon). Signal intensities were quantified using ImageJ and data analyzed using GraphPad.

The results are shown in FIGS. 19A-19E. It can be seen that for RIPA fractions, RIPK1 and pMLKL levels were significantly higher in the knock-in rats of the present disclosure than that in wildtype rats. And consistent with previous reports in AD patients, RIPK3 levels were similar between the knock-in rats of the present disclosure and that in wildtype rats.

In addition, expression of necroptosis markers RIPK1, MLKL, and RIPK3 were examined in the knock-in rats obtained in Example 5 (e.g., the F1 rats). Briefly, the rats were perfused with PBS and 4% paraformaldehyde under deep anaesthesia and the brains were post-fixed overnight in 4% paraformaldehyde. Brains were sectioned at 30 μm using a vibratome (Leica). Sections were permeabilized and blocked in PBS containing 0.2% Triton X-100 and 10% normal goat serum at room temperature for 2 h. Sections were incubated overnight at 4° C. with the following primary antibodies: anti-RIPK1 (1:200, BD Biosciences, 610459), anti-RIPK3 (1:500, Stata Crus, 374639), anti-MLKL (1:200, EnoGene, E2A7412), and anti-pMLKL (1:200, Abcam, ab196436). 1-fluoro-2,5-bis(3-carboxy-4-hydroxystyryl) benzene (FSB) was used for detection of amyloidosis. The next day, the sections were washed 3 times in PBS and exposed to AlexaFluor 647 donkey anti-mouse IgG (1:500, Invitrogen) or Alexa Fluor 594 goat anti-mouse IgG (1:500, Invitrogen) secondary antibodies and cell nuclei visualized with Hoechst 33342 (1:5000, Sigma-Aldrich; 94403). The sections were imaged on an Olympus FluoView FV1000 BX2 upright confocal microscope. Image analysis using Image J and Imaris8 software, and statistical data analysis using Graphpad.

Figure 34:
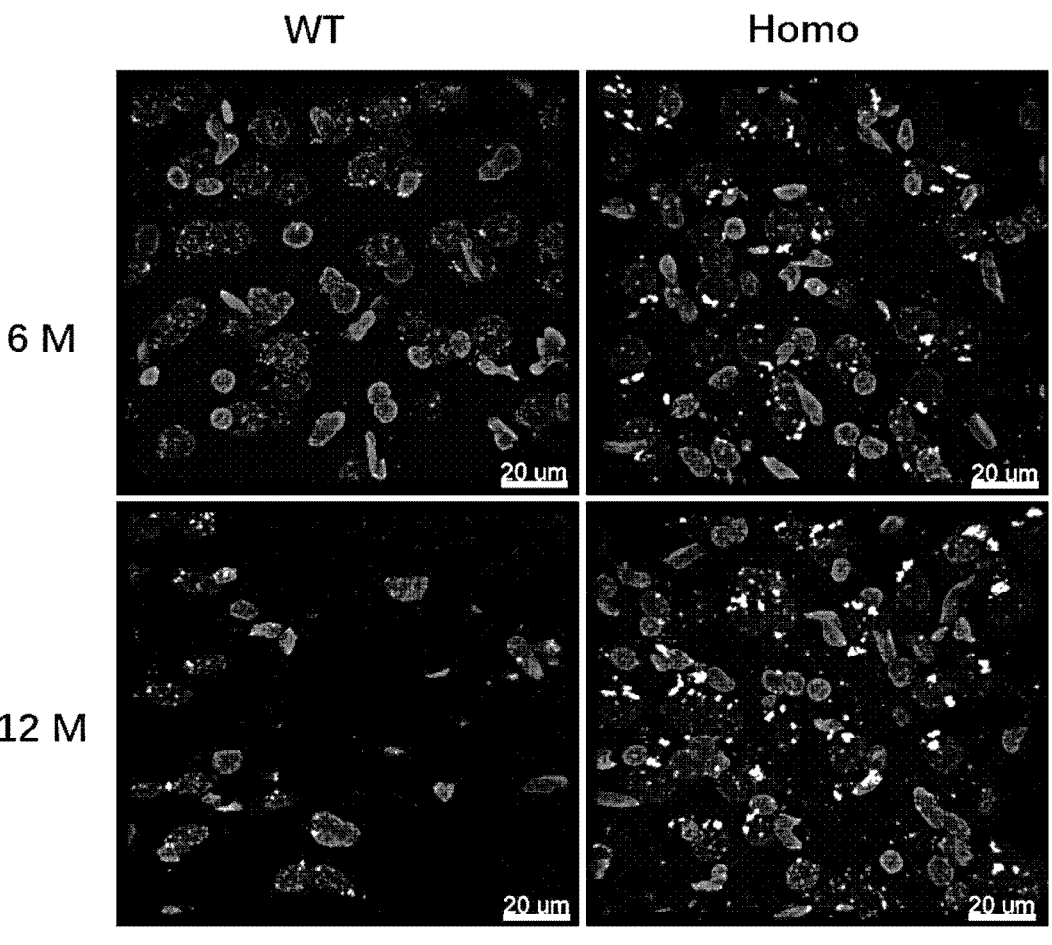
FIG. 34 illustrates RIPK1 expression in 6-month old wildtype rats and 6-month old rats of the present disclosure, and 12-month old wildtype rats and 12-month old rats of the present disclosure.
Figure 35A:
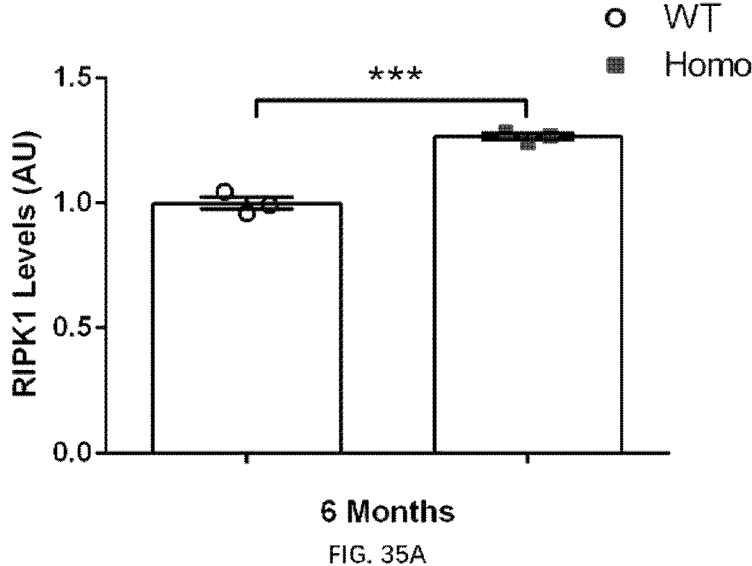
FIG. 35A illustrates RIPK1 expression in 6-month old wildtype rats and 6-month old rats of the present disclosure.
Figure 35B:
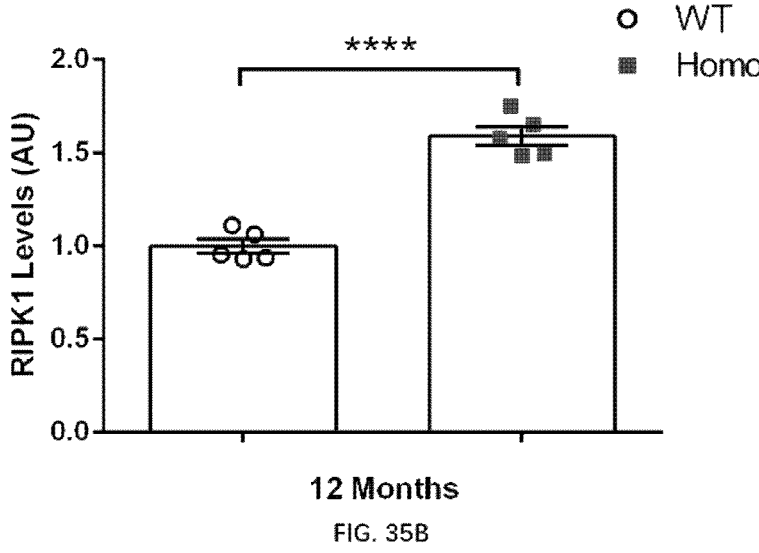
FIG. 35B illustrates RIPK1 expression in 12-month old wildtype rats and 12-month old rats of the present disclosure.

As shown in FIGS. 34, 35A and 35B, comparing to that observed in the corresponding wildtype rats, increased expression level of RIPK1 was observed in the knock-in rats of the present disclosure (e.g., in the rat brain, 6-month old and 12-month old respectively), e.g., when the rats were homozygous for the chimeric App gene.

Figure 36:
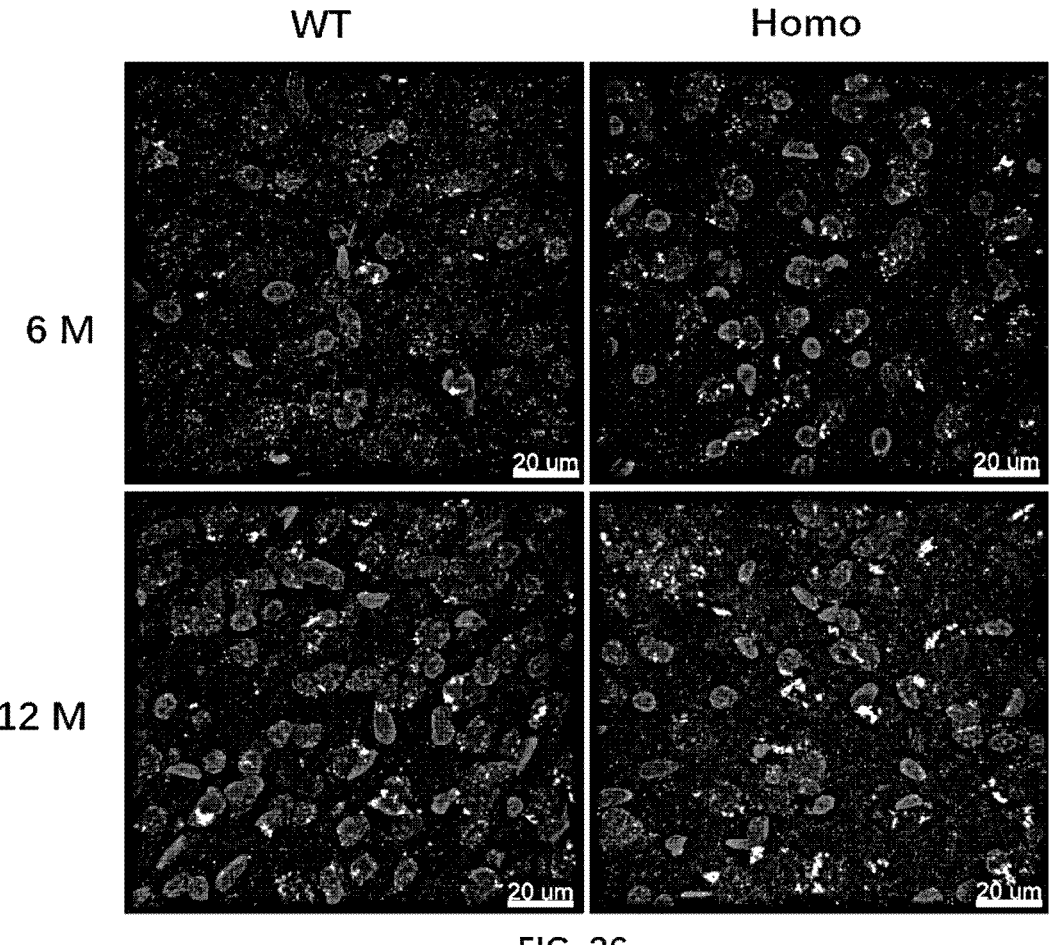
FIG. 36 illustrates RIPK3 expression 6-month old wildtype rats and 6-month old rats of the present disclosure, and 12-month old wildtype rats and 12-month old rats of the present disclosure.
Figure 37A:
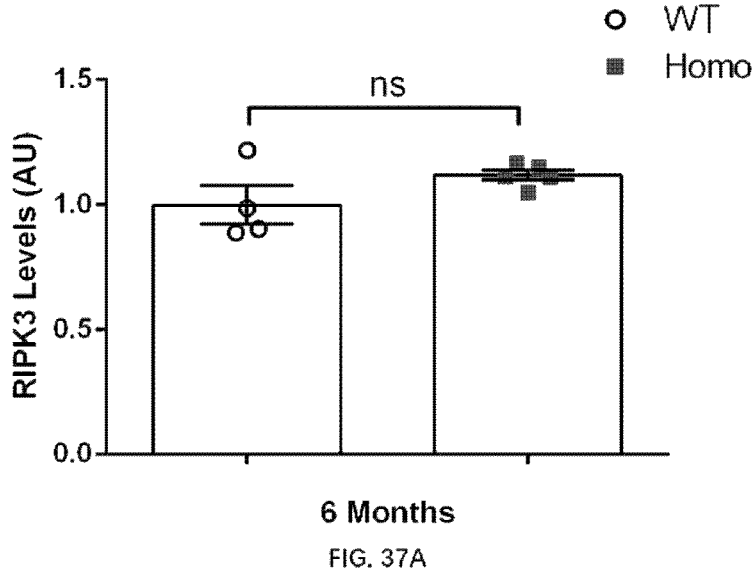
FIG. 37A illustrates RIPK3 expression in 6-month old wildtype rats and 6-month old rats of the present disclosure.
Figure 37B:
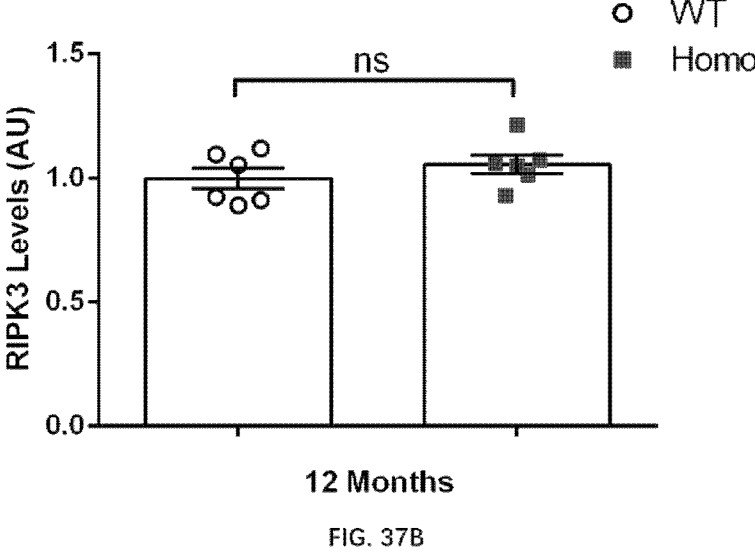
FIG. 37B illustrates RIPK3 expression in 12-month old wildtype rats and 12-month old rats of the present disclosure.

As shown in FIGS. 36, 37A and 37B, expression level of RIPK3 was similar between the knock-in rats of the present disclosure and that in wildtype rats (e.g., in the rat brain, 6-month old and 12-month old respectively), e.g., when the rats were homozygous for the chimeric App gene.

Figure 38A:
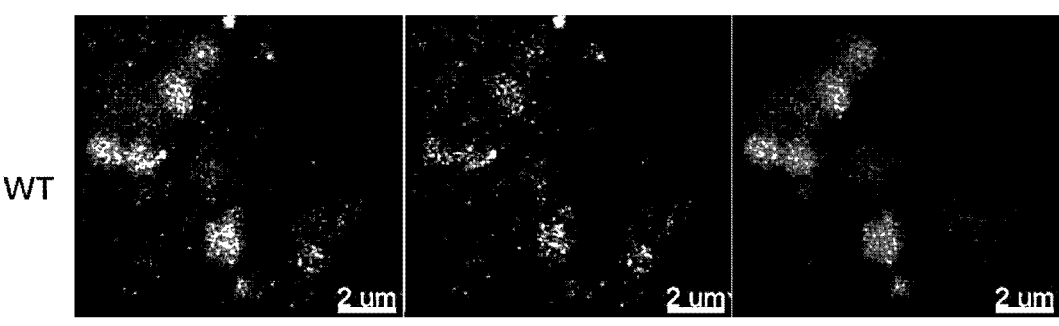
FIG. 38A-38B illustrate necrosome formation in 12-month old wildtype rats and 12-month old rats of the present disclosure, revealed by RIPK1 and RIPK3 expression and colocalization.
Figure 38B:
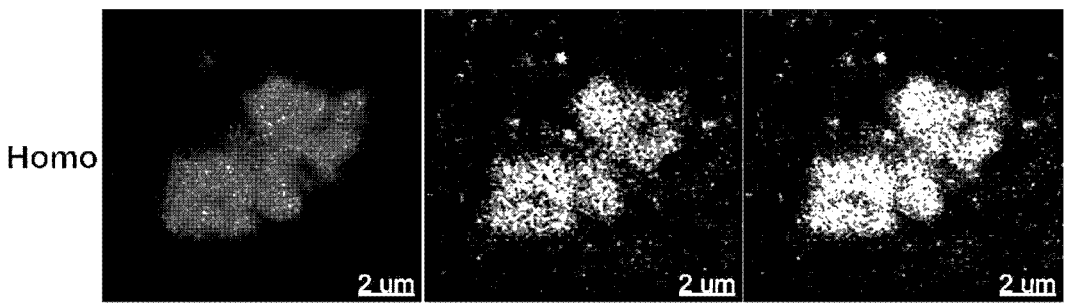
Figure 39:
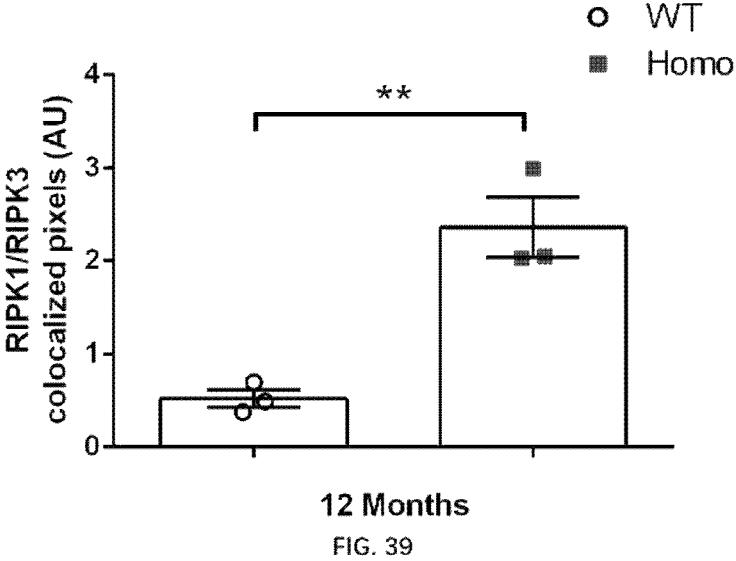
FIG. 39 illustrates RIPK1 and RIPK3 colocalization in 12-month old wildtype rats and 12-month old rats of the present disclosure.

In addition, as shown in FIGS. 38A, 38B and 39, comparing to that observed in the corresponding wildtype rats, increased colocalization of RIPK1 expression and RIPK3 expression was observed in the knock-in rats (e.g., in the rat brain, 12-month old) of the present disclosure, e.g., when the rats were homozygous for the chimeric App gene.

Figure 40A:
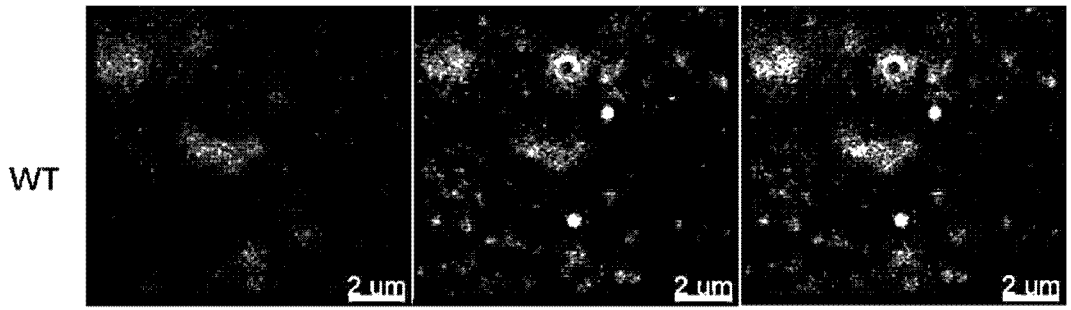
FIG. 40A-40B illustrate necrosome formation in 12-month old wildtype rats and 12-month old rats of the present disclosure, revealed by RIPK1 and MLKL expression and colocalization.
Figure 40B:
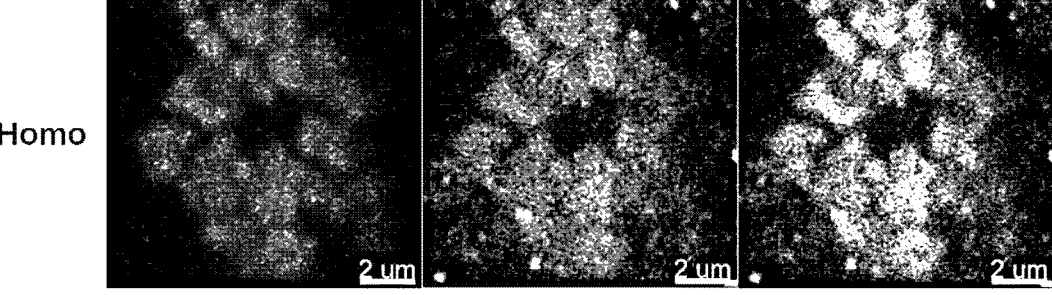
Figure 41:
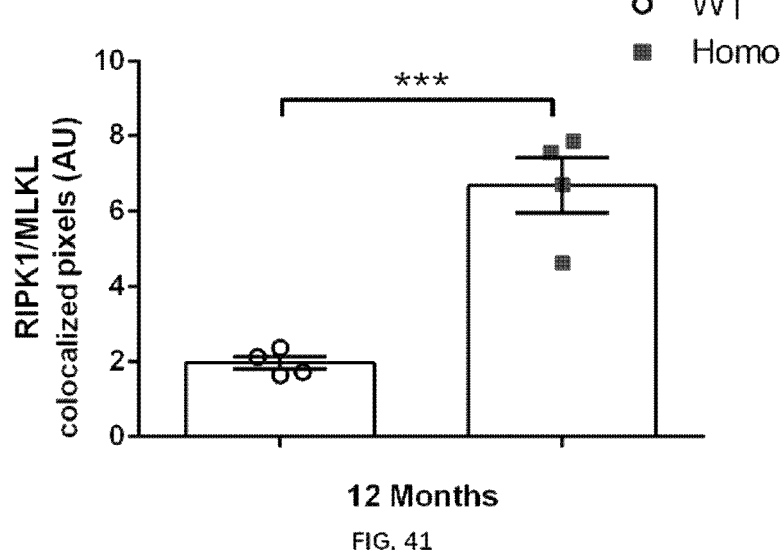
FIG. 41 illustrates RIPK1 and MLKL colocalization in 12-month old wildtype rats and 12-month old rats of the present disclosure.
Figure 42A:
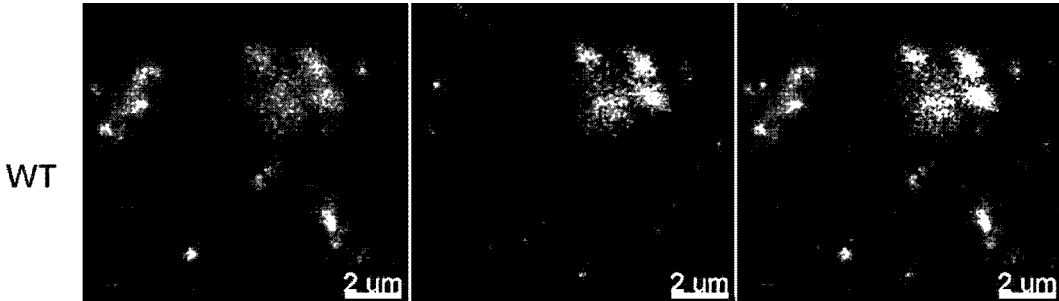
FIG. 42A-42B illustrate necrosome formation in 12-month old wildtype rats and 12-month old rats of the present disclosure, revealed by RIPK3 and MLKL expression and colocalization.
Figure 42B:
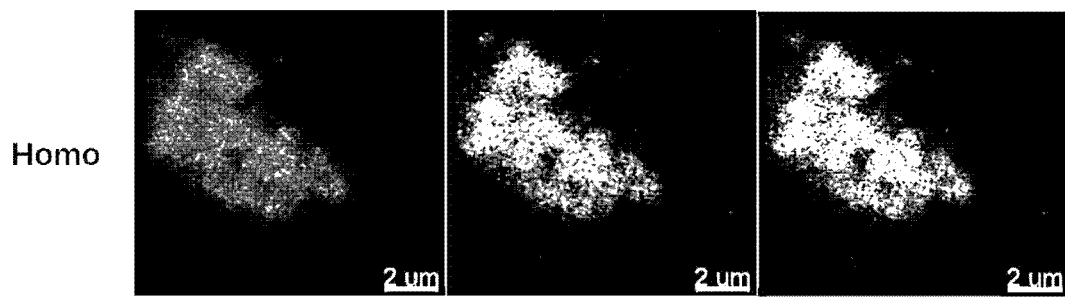
Figure 43:
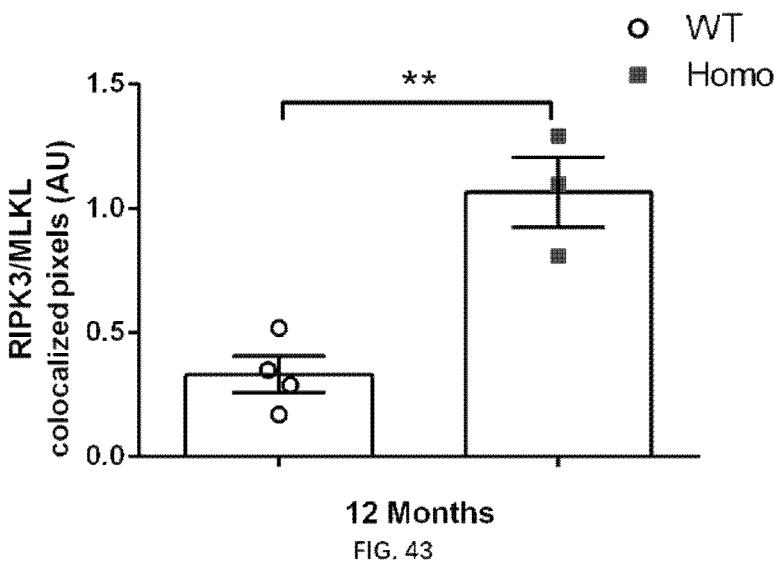
FIG. 43 illustrates RIPK3 and MLKL colocalization in the brain of 12-month old wildtype rats and 12-month old rats of the present disclosure.
Figures 44A, 44B:
FIG. 44A-44B illustrate RIPK1 and Iba1 colocalization in the brain of 6-month old wildtype rats and 6-month old rats of the present disclosure.
Figure 45:
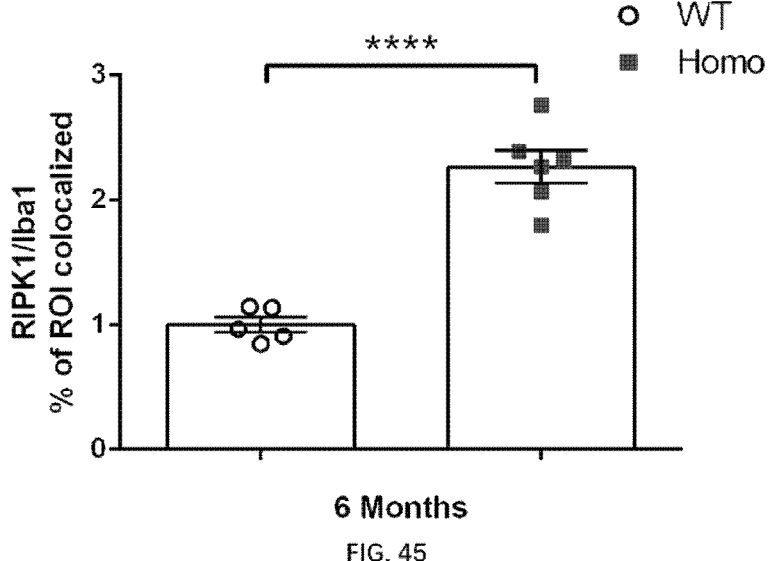
FIG. 45 illustrates RIPK1 and Iba1 colocalization in the brain of 6-month old wildtype rats and 6-month old rats of the present disclosure.
Figures 46A, 46B:
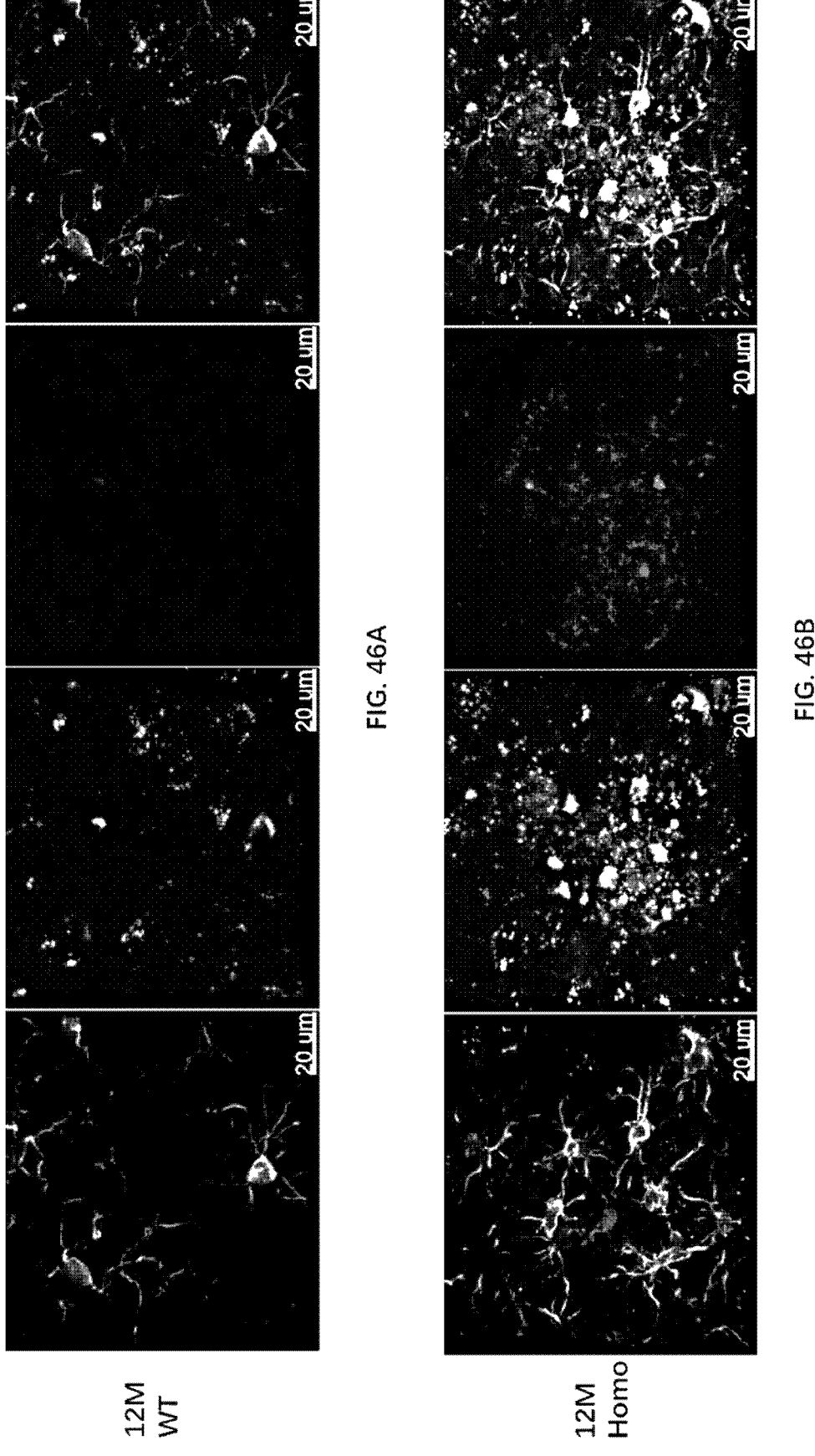
FIG. 46A-46B illustrate RIPK1 and Iba1 colocalization in the brain of 12-month old wildtype rats and 12-month old rats of the present disclosure.
Figure 47:
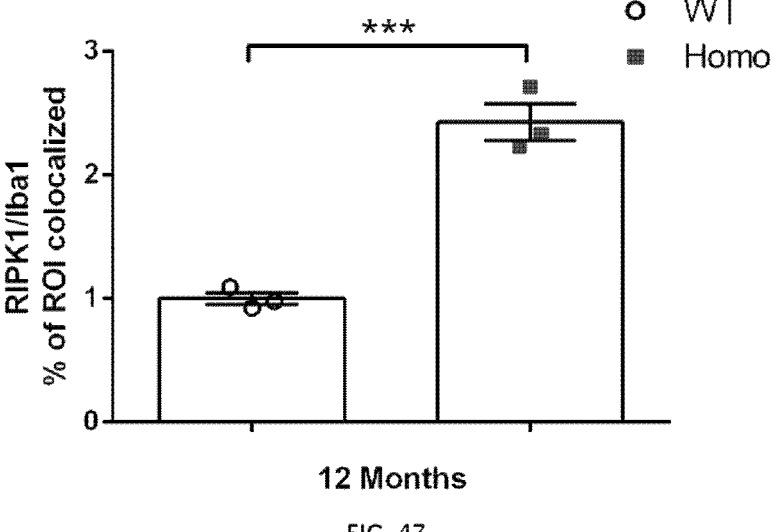
FIG. 47 illustrates RIPK1 and Iba1 colocalization in the brain of 12-month old wildtype rats and 12-month old rats of the present disclosure.
Figure 49:
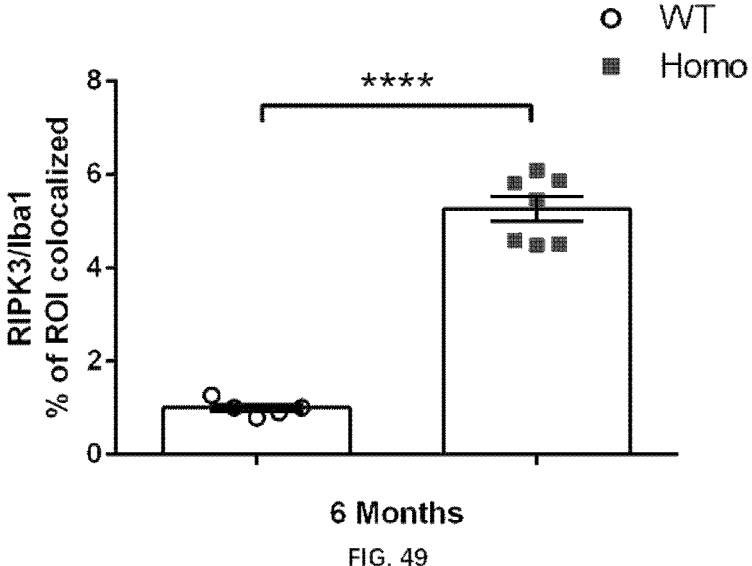
FIG. 49 illustrates RIPK3 and Iba1 colocalization in the brain of 6-month old wildtype rats and 6-month old rats of the present disclosure.
Figures 50A, 50B:
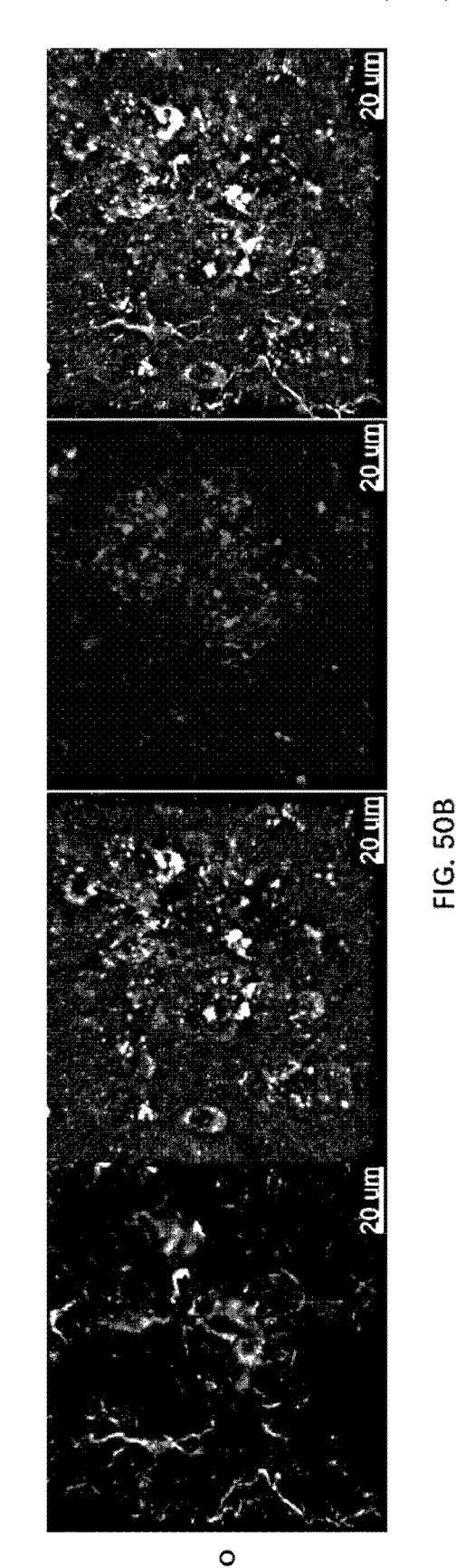
FIG. 50A-50B illustrate RIPK3 and Iba1 colocalization in the brain of 12-month old wildtype rats and 12-month old rats of the present disclosure.
Figure 51:
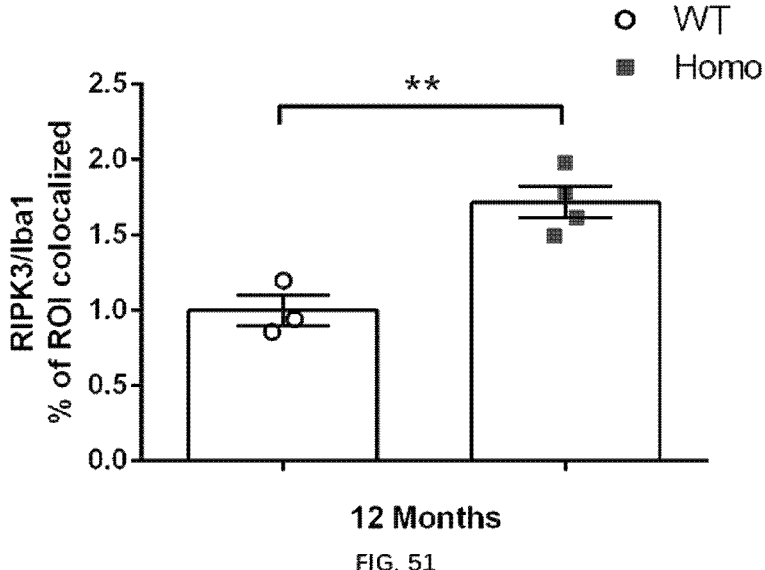
FIG. 51 illustrates RIPK3 and Iba1 colocalization in the brain of 12-month old wildtype rats and 12-month old rats of the present disclosure.

As shown in FIGS. 40A, 40B and 41, comparing to that observed in the corresponding wildtype rats, increased colocalization of RIPK1 expression and MLKL expression was observed in the knock-in rats (e.g., in the rat brain, 12-month old) of the present disclosure, e.g., when the rats were homozygous for the chimeric App gene. As shown in FIGS. 42A, 42B and 43, comparing to that observed in the corresponding wildtype rats, increased colocalization of RIPK3 expression and MLKL expression was observed in the knock-in rats (e.g., in the rat brain, 12-month old) of the present disclosure, e.g., when the rats were homozygous for the chimeric App gene, although as shown in FIGS. 36, 37A and 37B, expression level of RIPK3 was not increased in the knock-in rats of the present disclosure, as comparing to that of the wildtype rats. In addition, comparing to that observed in the corresponding wildtype rats, increased aggregation of MLKL was observed in the knock-in rats (e.g., in the rat brain, 12-month old) of the present disclosure, e.g., when the rats were homozygous for the chimeric App gene, and the MLKL was observed to be located close to the cell/tissue membrane. These results indicate increased formation of necrosomes in the knock-in rats of the present disclosure.

The results of this Example indicate neuronal loss (as revealed by necroptosis and formation of necrosomes) in the knock-in rats of the present disclosure, and the phenotypes are similar to those seen in human AD patients.

Example 11

Microgliosis and Astrocytosis in the Brain in the Knock-In Rat

Western Blotting was used to examine microgliosis and astrocytosis in the knock-in rat model obtained in Example 5 (i.e., F1 rats). Briefly, brain tissue was homogenized in RIPA (50 mM Tris HCl pH 8.0, 150 mM NaCl, 1% NP-40, 0.5% sodium deoxycholate, CA630, 1% EDTA, 0.1% SDS) buffer with protease inhibitors (Roche Diagnostics). Tissue debris was isolated and discarded by centrifugation at 14,000 r.p.m. for 15 min. Lysates were quantitated using BCA protein assay kit (Thermo Fisher) and equal amounts of protein were loaded on a SDS-PAGE gels. Protein was transferred from acrylamide gels to PVDF membranes (Immobilon-P, Millipore) at 90V for 100 min. Membranes were blocked using bovine serum albumin (BSA, 5% w/v) diluted in TBS-T for 1 h. After blocking, membranes were incubated overnight at 4° C. in BSA (2.5% w/v) in TBS-T with the following appropriate primary antibodies: anti-GFAP (MAB3402, Millipore), anti-Iba1 (Wako), anti-β-actin (1:5000, Abcam, ab9485). The next day, the blots were washed three times with TBS-T for 15 min and incubated in the specific secondary antibodies (1:5000, Invitrogen/Thermo Fisher Scientific, 31462 and 31432) for 1 hr at room temperature under constant agitation. After washing, the membrane was either probed with enhanced chemiluminescence (ECL) Western blotting substrate (Thermo Fisher Scientific, 34080) and with detection of luminescence (Tanon). Signal intensities were quantified using ImageJ and data analyzed using GraphPad.

The results are shown in FIGS. 20A-20D. It can be seen that for the GFAP staining reflecting the degree of microgliosis and for the Iba1 staining reflecting the degree of astrocytosis, both levels were significantly higher in the knock-in rats of the present disclosure than that in the wildtype rats.

Example 12

Immunohistochemistry of Astrocytes (GFAP), Aβ (FSB) and Microglia (Iba1) of the Knock-In Rats The immunohistochemistry of astrocytes (GFAP), Aβ (FSB) and microglia (Iba1) in the knock-in rats of the present disclosure (e.g., the F1 rats) were examined by immune-histochemical and histochemical studies. Briefly, the paraffin-embedded and frozen rat brain sections were immunostained using antibodies specific to Iba1 (Wako, 019-19741) and GFAP (MAB3402, Millipore). 1-fluoro-2, 5-bis(3-carboxy-4-hydroxystyryl) benzene (FSB) was used for detection of amyloidosis. The tyramide signal amplification (PerkinElmer Life Sciences) was used, when necessary. The immune-reactive areas were calculated using MetaMorph imaging software (Universal Imaging). To reduce the variance among tissue sections, the average of data from at least four sections per mouse was used as an individual value.

The results are shown in FIGS. 21, 22, 53, 54A, 54B, 55A and 55B. It can be seen that comparing to those observed in the corresponding wildtype rats, microgliosis and astrocytosis were significantly increased in the knock-in rats (brain, 6-month, 12-month, or 22-month) of the present disclosure. In addition, microgliosis and astrocytosis are associated with the Amyloid plaques.

Example 13

Synaptic Degeneration in the Knock-In Rats

Synaptic degeneration in the knock-in rats of the present disclosure (e.g., the F1 rats) was examined by immune-histochemical and histochemical studies. Briefly, paraffin-embedded and frozen rat brain sections were immunostained using antibodies specific to PSD-95 (NeuroMab, 73-028), synaptophysin (conjugated with FITC; clone SY38, PRO-GEN) and DAPI (Gibco, D1306). 1-fluoro-2,5-bis(3-car-boxy-4-hydroxystyryl) benzene (FSB) was used for detection of amyloidosis. The tyramide signal amplification (PerkinElmer Life Sciences) was used, when necessary. The immune-reactive areas were calculated using MetaMorph imaging software (Universal Imaging). To reduce the variance among tissue sections, the average of data from at least four sections per mouse was used as an individual value.

Figure 23:
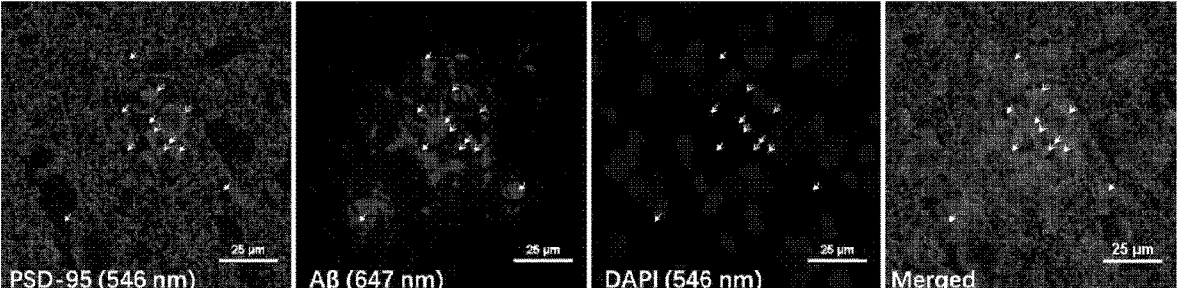
FIG. 23 illustrates synaptic degeneration in the brain of the rats of the present disclosure.
Figures 52A, 52B:
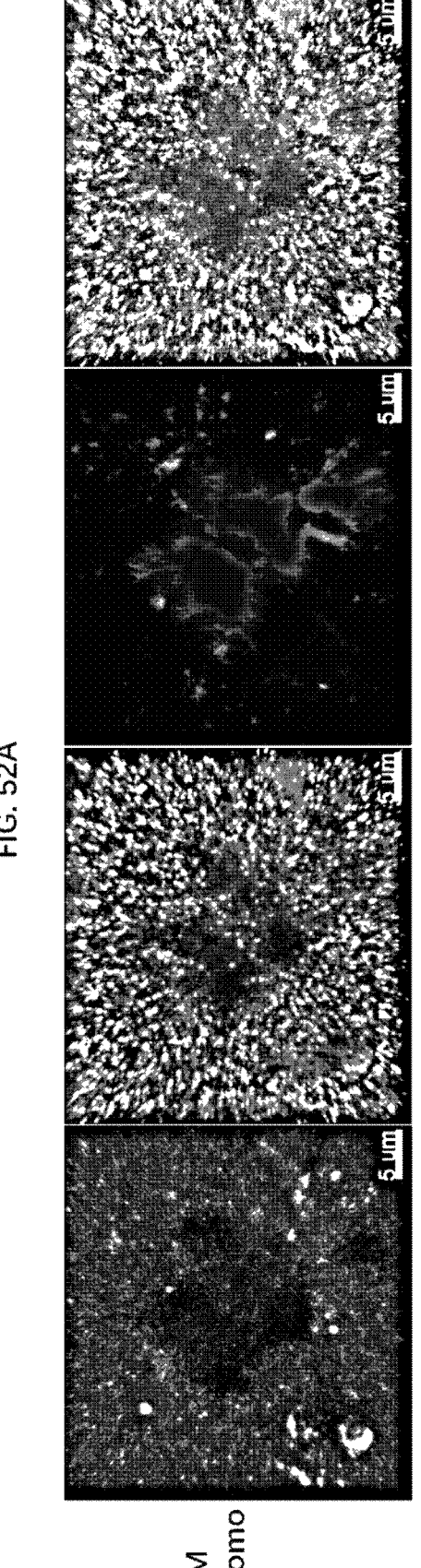
FIG. 52A-52B illustrate synaptic degeneration in the brain of 9-month old wildtype rats and 9-month old rats of the present disclosure.
Figure 53:
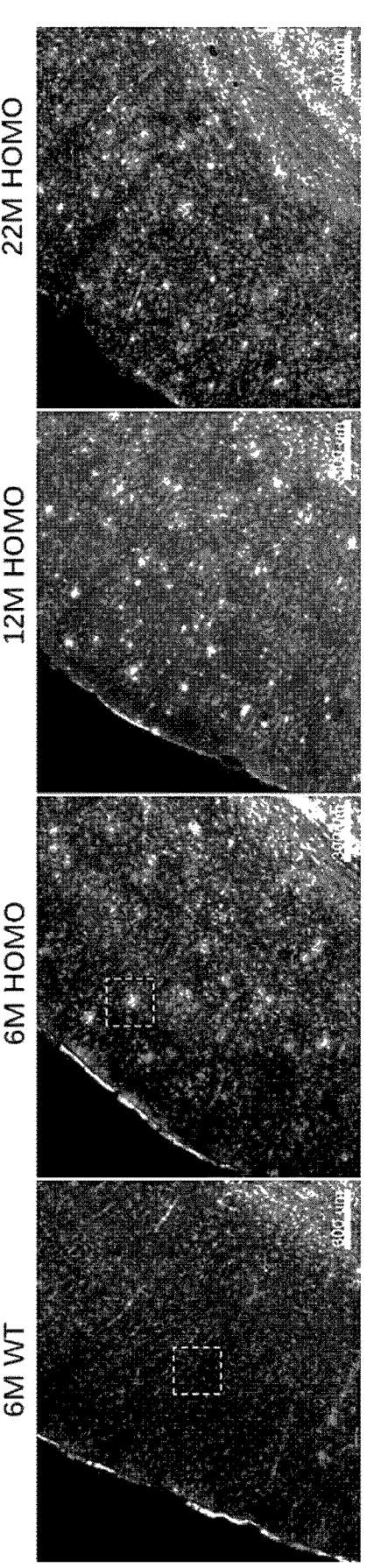
FIG. 53 illustrates microgliosis and astrocytosis in the brain of 6-month old wildtype rats, 6-month old rats of the present disclosure, 12-month old wildtype rats and 12-month old rats of the present disclosure.
Figures 54A, 54B:
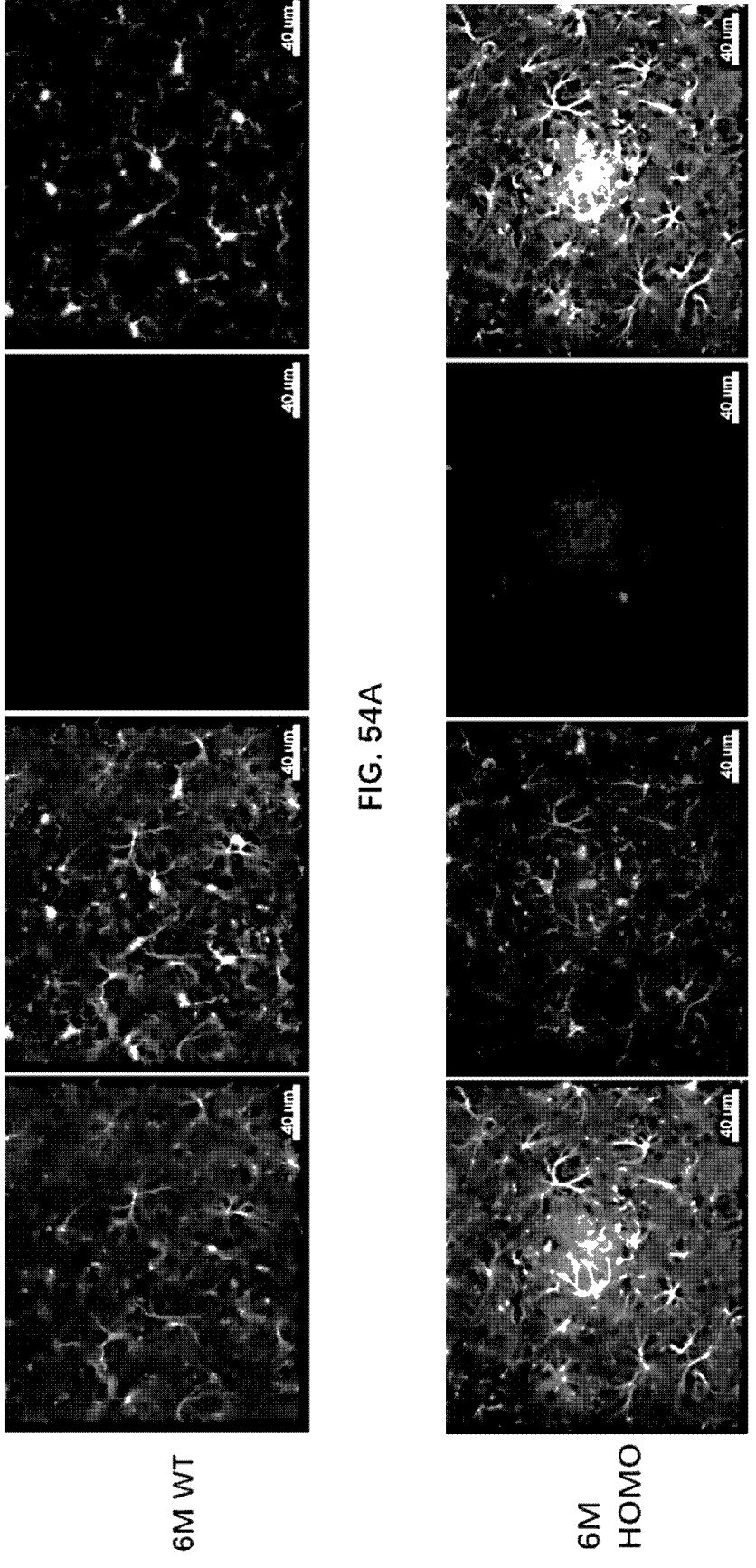
FIG. 54A-54B illustrate microgliosis and astrocytosis in the brain of 6-month old wildtype rats and 6-month old rats of the present disclosure.
Figure 55A:
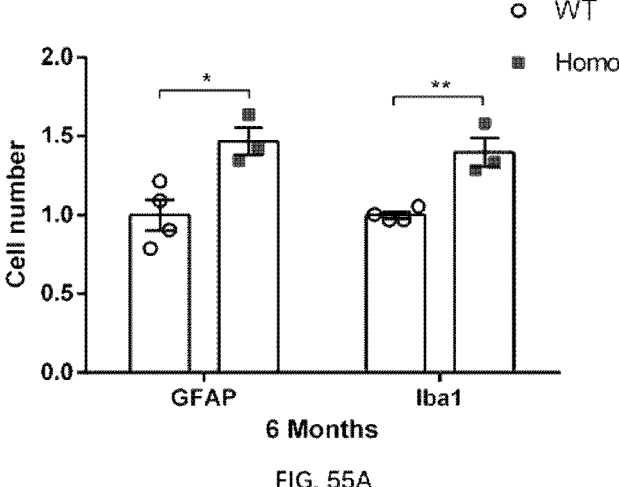
FIG. 55A-55B illustrate microgliosis and astrocytosis in the brain of 6-month old wildtype rats, 6-month old rats of the present disclosure, 12-month old wildtype rats and 12-month old rats of the present disclosure.
Figure 55B:
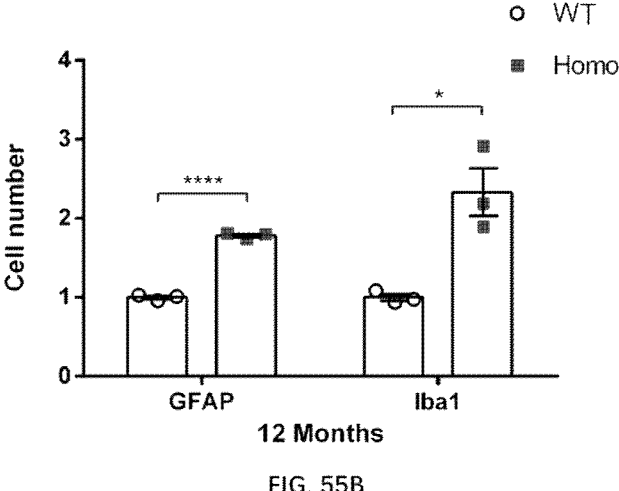

The results are shown in FIG. 23. It can be seen that synaptic degeneration was observed in the knock-in rats of the present disclosure, as revealed by swelling and hollowing of postsynaptic density (PSD-95) in the brain of these rats. In addition, as shown in FIGS. 52A and 52B, synaptic degeneration was observed in the knock-in rats (e.g., 9-month old, homozygous for the chimeric App gene) of the present disclosure, as revealed by swelling and hollowing of postsynaptic density, shown with anti-PSD-95 staining and anti-synaptophysin staining in the brain of these rats. Further, the observed swelling and hollowing of postsynaptic density colocalized with the amyloid plaques.

Example 14

Oligomerization and Aggregation of Tau

Conformational alteration of tau protein was examined in the knock-in rats obtained in Example 5 (e.g., the F1 rats). Briefly, the rats were perfused with PBS and 4% paraformaldehyde under deep anaesthesia and the brains were post-fixed overnight in 4% paraformaldehyde. Brains were sectioned at 30 μm using a vibratome (Leica). Sections were permeabilized and blocked in PBS containing 0.2% Triton X-100 and 10% normal goat serum at room temperature for 2 h. Sections were incubated overnight at 4° C. with the following primary antibodies: anti-MC1 (1:20; a gift from P. Davies, Albert Einstein College of Medicine, New York, New York, USA) and anti-MAP-2 (1:1000; Abcam; ab32454). The next day, the sections were washed 3 times in PBS and exposed to AlexaFluor 647 donkey anti-mouse IgG (1:500, Invitrogen) or Alexa Fluor 594 goat anti-mouse IgG (1:500, Invitrogen) secondary antibodies and cell nuclei visualized with Hoechst 33342 (1:5000, Sigma-Aldrich; 94403). The sections were imaged on an Olympus FluoView FV1000 BX2 upright confocal microscope. Image analysis using Image J and Imaris8 software, and statistical data analysis using Graphpad.

Figures 33A, 33B:
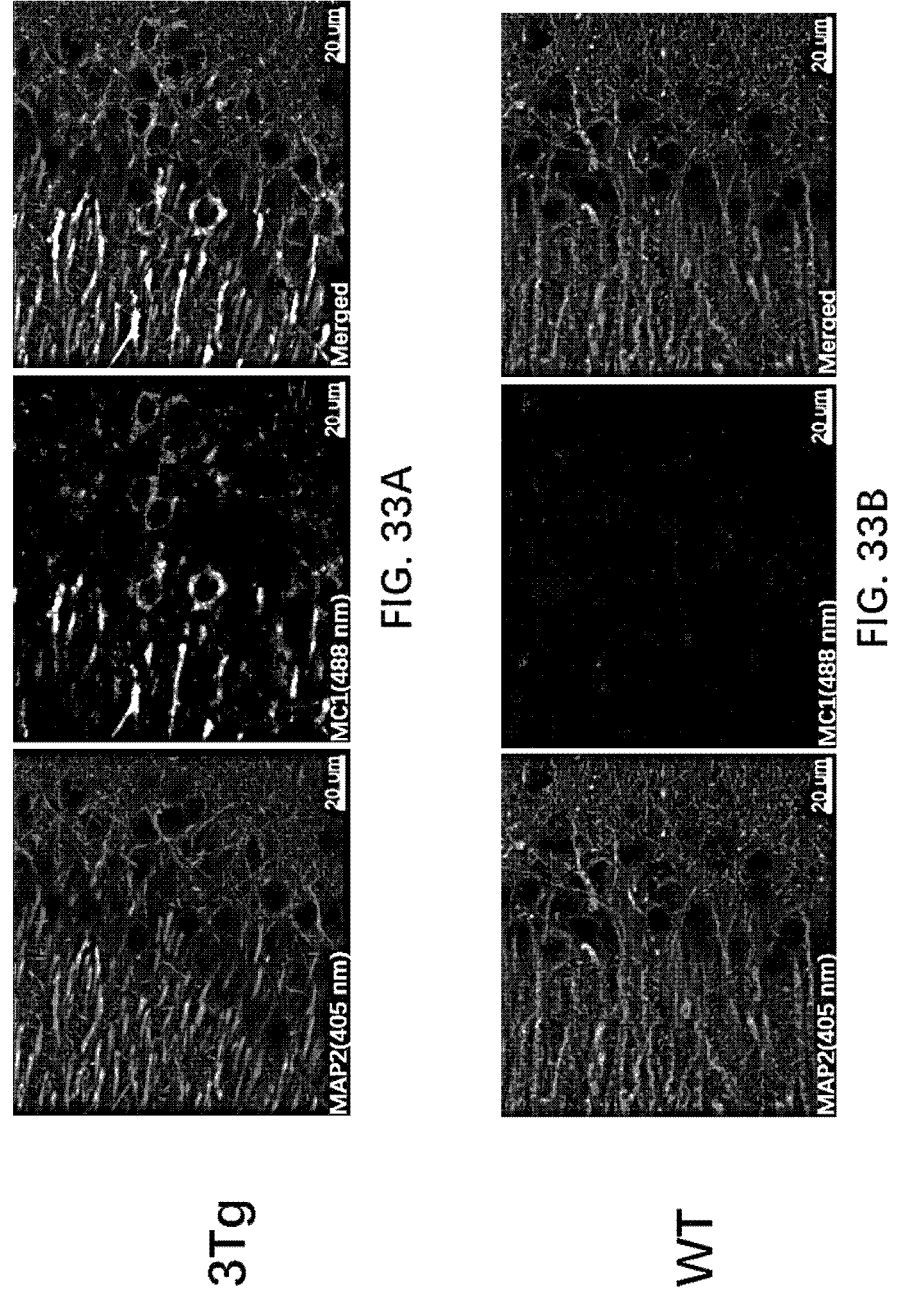
FIG. 33A-33C illustrate aggregation of tau protein in 12-month old 3Tg mouse, 22-month old wildtype rats and 22-month old rats of the present disclosure.
Figure 33C:
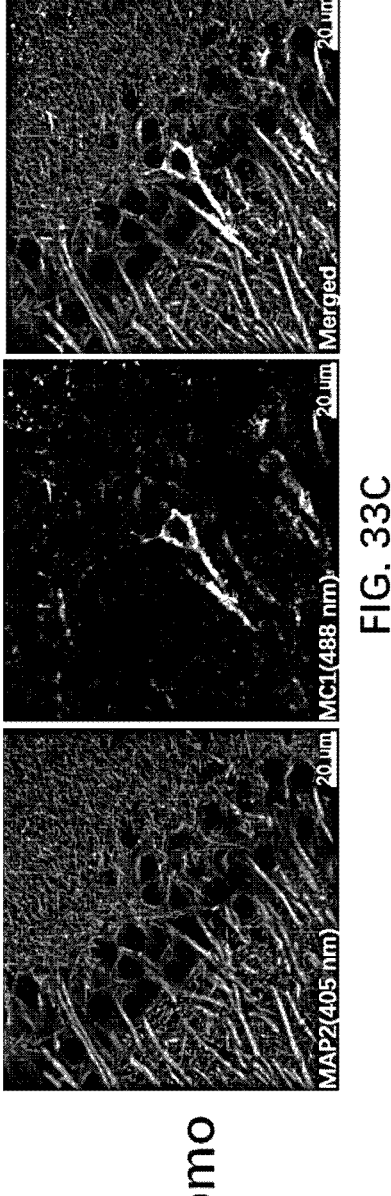

As shown in FIGS. 33A-33C, aggregation of tau proteins was observed in the knock-in rats of the present disclosure (e.g., at an age of 22-month, when homozygous for the chimeric App gene). Further, the aggregated tau proteins (as revealed with anti-MC1 staining) colocalized with the tubulin/microtubules (as revealed with anti-MAP2 staining). Similar results were observed in the triply transgenic mouse (see FIG. 33A, 3×Tg-AD mouse, serving as a positive control). However, no aggregation of tau protein was observed in the corresponding wildtype rats (see FIG. 33C).

Example 15

Colocalization of Necrosomes and Microglia

Colocalization of cell necroptosis and microglia formation was examined in the knock-in rats obtained in Example 5 (e.g., the F1 rats). Briefly, the rats were perfused with PBS and 4% paraformaldehyde under deep anaesthesia and the brains were post-fixed overnight in 4% paraformaldehyde. Brains were sectioned at 30 μm using a vibratome (Leica). Sections were permeabilized and blocked in PBS containing 0.2% Triton X-100 and 10% normal goat serum at room temperature for 2 h. Sections were incubated overnight at 4° C. with the following primary antibodies: anti-RIPK1 (1:200, BD Biosciences, 610459), anti-RIPK3 (1:500, Stata Crus, 374639), and anti-Iba1 (1:1000, Wako, 019-19741). 1-fluoro-2,5-bis(3-carboxy-4-hydroxystyryl)benzene (FSB) was used for detection of amyloidosis. The next day, the sections were washed 3 times in PBS and exposed to AlexaFluor 647 donkey anti-mouse IgG (1:500, Invitrogen) or Alexa Fluor 594 goat anti-mouse IgG (1:500, Invitrogen) secondary antibodies and cell nuclei visualized with Hoechst 33342 (1:5000, Sigma-Aldrich; 94403). The sections were imaged on an Olympus FluoView FV1000 BX2 upright confocal microscope. Image analysis using Image J and Imaris8 software, and statistical data analysis using Graph-pad.

As shown in FIGS. 44A-44B, 45, 46A-46B, 47, 48A-48B, 49, 50A-50B, and 51, comparing to that observed in the corresponding wildtype rats, increased colocalization of RIPK1 expression and Iba1 expression, as well as increased colocalization of RIPK3 expression and Iba1 expression were observed in the knock-in rats (e.g., in the rat brain, 6-month old and 12-month old) of the present disclosure, e.g., when the rats were homozygous for the chimeric App gene. These results indicate that necrosome formation and microglia formation occur in the same region/cell of the brain, similar to the phenotypes observed in human AD patients.

Example 16

Neuronal Cell Loss in the Knock-In Rats

Neuronal cell loss was also examined in the knock-in rats obtained in Example 5 (e.g., the F1 rats). Briefly, the rats were perfused with PBS and 4% paraformaldehyde under deep anaesthesia and the brains were post-fixed overnight in 4% paraformaldehyde. Brains were sectioned at 30 μm using a vibratome (Leica). Sections were permeabilized and blocked in PBS containing 0.2% Triton X-100 and 10% normal goat serum at room temperature for 2 hours. Sections were incubated overnight at 4° C. with anti-NeuN (1:1000;

Merck; MAB377). The next day, the sections were washed 3 times in PBS and exposed to AlexaFluor 647 donkey anti-mouse IgG (1:500, Invitrogen) or Alexa Fluor 594 goat anti-mouse IgG (1:500, Invitrogen) secondary antibodies and cell nuclei visualized with Hoechst 33342 (1:5000, Sigma-Aldrich; 94403). The sections were imaged on an Olympus FluoView FV1000 BX2 upright confocal microscope. Image analysis using Image J and Imaris8 software, and statistical data analysis using Graphpad.

Figure 56:
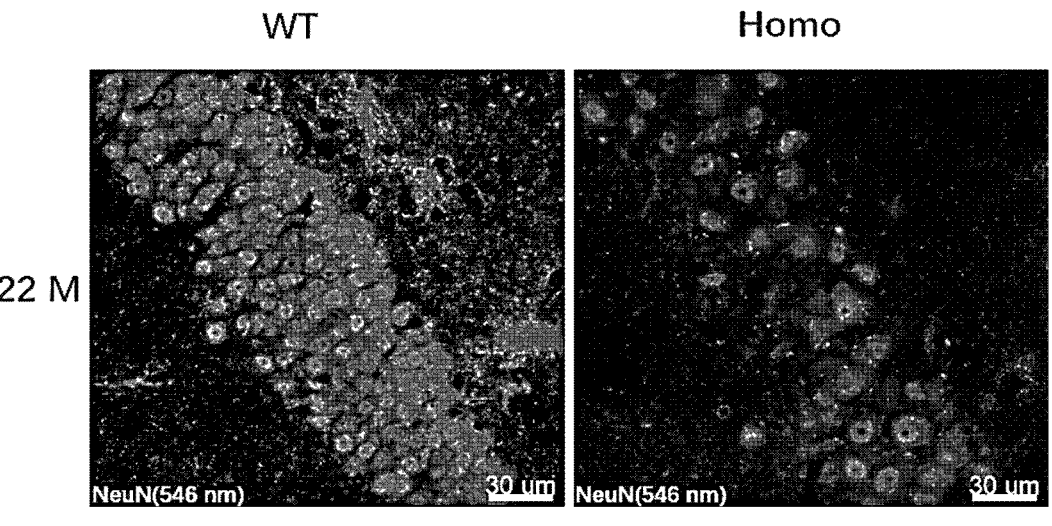
FIG. 56 illustrates neuronal cell loss in the brain of 22-month old wildtype rats and 22-month old rats of the present disclosure.
Figure 57A:
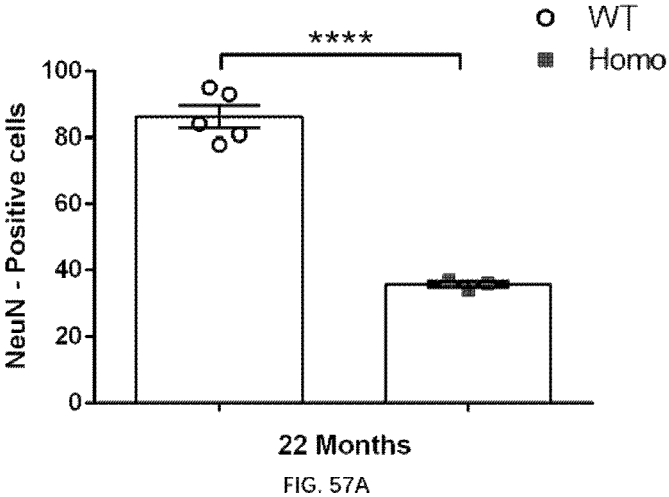
FIG. 57A-57B illustrate neuronal cell loss in the brain of 22-month old wildtype rats and 22-month old rats of the present disclosure.
Figure 57B:
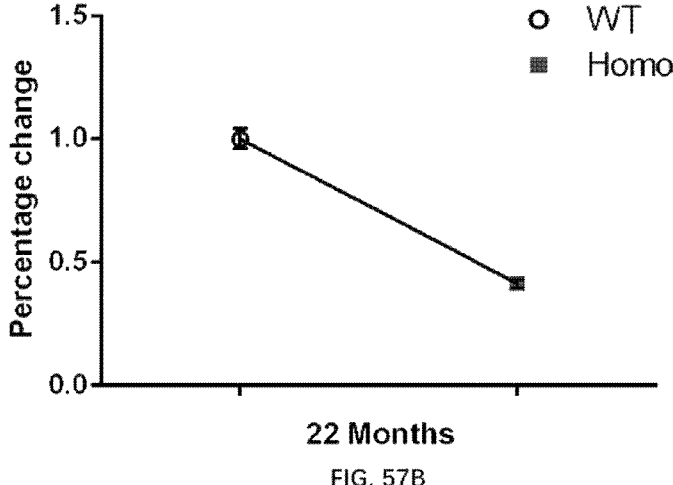
Figure 58:
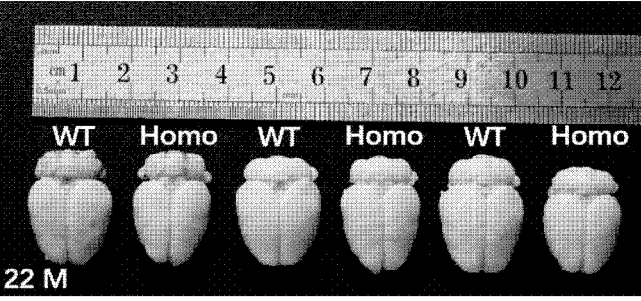
FIG. 58 illustrates brain size change in 22-month old wildtype rats and 22-month old rats of the present disclosure.
Figures 59, 60A:
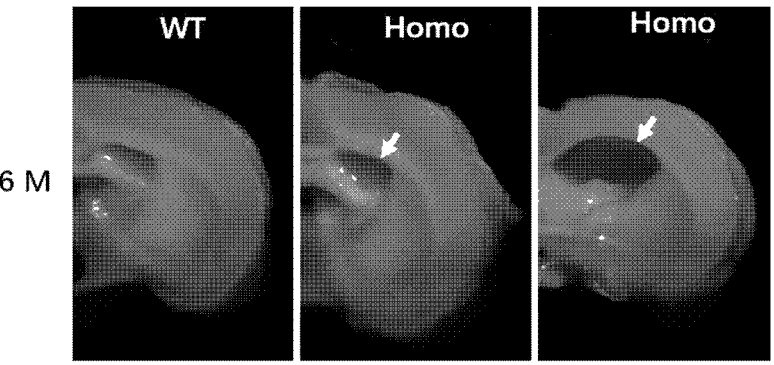
FIG. 59 illustrates brain structure and morphology change in 6-month old wildtype rats and 6-month old rats of the present disclosure.
FIG. 60A-60B illustrate change of brain weight of 6-month old wildtype rats, 6-month old rats of the present disclosure, 22-month old wildtype rats and 22-month old rats of the present disclosure.
Figure 60B:
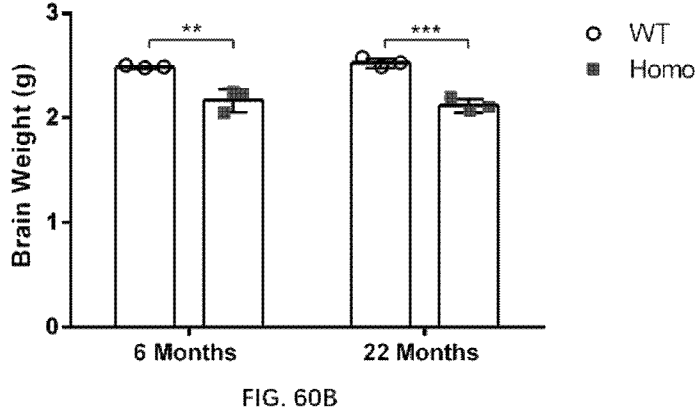

The results are shown in FIGS. 56, 57A and 57B. It can be seen that comparing to that observed in the corresponding wildtype rats, a decrease of NeuN positive neuron cell number was observed in the knock-in rats (e.g., in the rat brain, 22-month old) of the present disclosure, e.g., when the rats were homozygous for the chimeric App gene.

Example 17

Morphology and Weight Change of Rat Brain

The morphology, size and weight of the rat brains were examined. For the histological staining, rats were anesthetized with Nembutal (pentobarbital sodium, 0.2 mL/100 g body weight), and killed by decapitation at the corresponding age; brains were removed and weighed. Then, the rat brains were fixed by submerging into 4% paraformaldehyde (PFA) in PBS, embedded into the paraffin, sectioned in corona plane and processed. For histological analyses, paraffin-embedded brains were coronally sectioned at 5-μm thickness on a microtome, and mounted on APS-coated slides. Then, the 5-μm thickness sections were deparaffinized, and stained with Hematoxylin and Eosin (Merck).

The results are shown in FIGS. 58, 59, 60A and 60B. It can be seen that comparing to that of the corresponding wildtype rats, reduced brain size, less brain weight, larger ventricular cavity and increased hippocampus damage or loss were observed in the knock-in rats (e.g., in the rat brain, 6-month old and 22-month old) of the present disclosure, e.g., when the rats were homozygous for the chimeric App gene.

Example 18

Open Field Test

Cognitive abilities of the rats according to the present disclosure were examined in an open field test. The test was performed in a circular arena with a diameter of 100 cm and a wall of 50 cm in hight. The central area of the open field was defined as a circular arena of 60 cm in diameter in the middle zone of the apparatus. The test room had a dim illumination to decrease the anxiety of the rats. The animal was introduced to the center of the field, and the horizontal activity (distance traveled), time spent in the central area and enter times to the center area were recorded for 5 min and analyzed by a computer-based system. The open field was cleaned after each test.

Figure 61A:
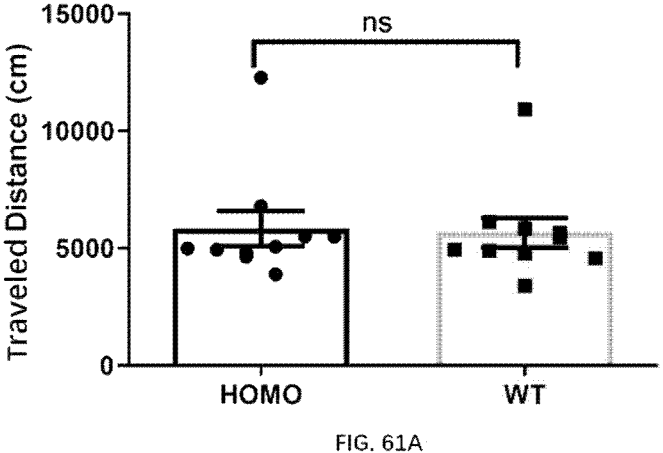
FIG. 61A-61C illustrate the result of open field test for 4-month old wildtype rats and 4-month old rats of the present disclosure.
Figure 61B:
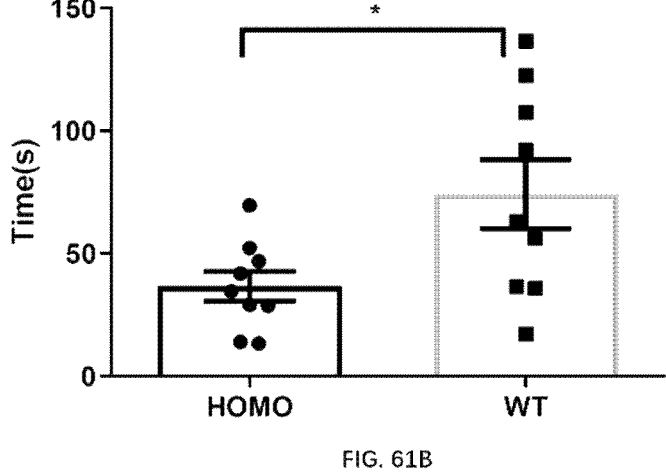
Figure 61C:
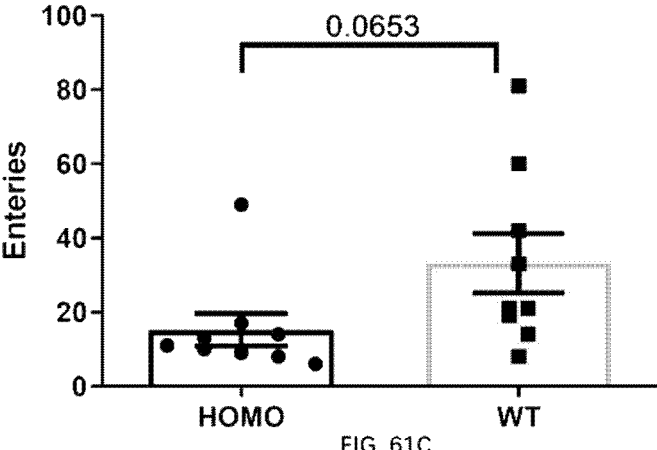

The results are shown in FIGS. 61A-61C. It can be seen that comparing to the corresponding wildtype rats, the knock-in rats of the present disclosure (e.g., 4-month old, homozygous for the chimeric App gene) traveled similar distance within the tested 5 mins (FIG. 61A), indicating a normal locomotor activity of these knock-in rats. However, comparing to the corresponding wildtype rats, the knock-in rats of the present disclosure spent less time in the central area of the open field (FIG. 61B) and entered into the central area less frequently (FIG. 61C), indicating that these knock-in rats had significantly weaker cognitive abilities.

Example 19

Rotarod Test

Locomotor activities of the rats according to the present disclosure were examined in a rotarod test. The rotarod apparatus consists of a 7 cm diameter cylinder positioned at a height 0.5 m. The cylinder can be mechanically controlled to rotate at pre-determined steady speed and/or accelerate (San Diego Instruments, San Diego, CA). The test included 3 training days and one test day. During the training days, each rat was given four 90-second trails per day; for each 90-second trail, each rat was placed on the cylinder, and then the cylinder was accelerated from 5 rpm to 15 rpm in 15-second, and maintained at that speed for 75-second. The interval time between trails was 15 min at least. During the test day, each rat was given three trails; during each trial, each rat was placed on the cylinder, and then the cylinder was accelerated from 5 rpm to 40 rpm in 300-second. During these 4 days, for each rat, the latency to fall off the cylinder was recorded for each trial, and the mean time for all the trails of the day was calculated.

Figure 62A:
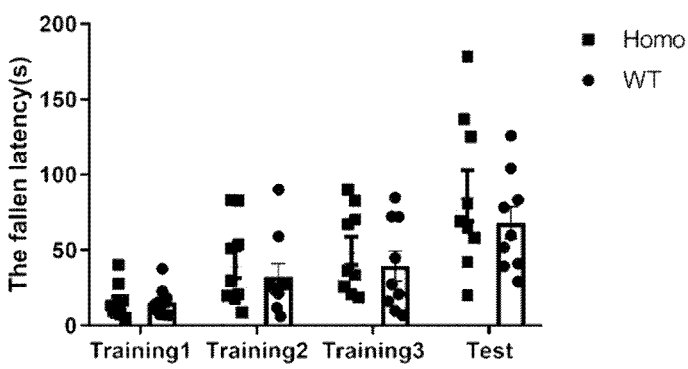
FIG. 62A-62B illustrate the result of rotarod test for 4-month old wildtype rats and 4-month old rats of the present disclosure, and for 6-month old wildtype rats and 6-month old rats of the present disclosure.
Figure 62B:
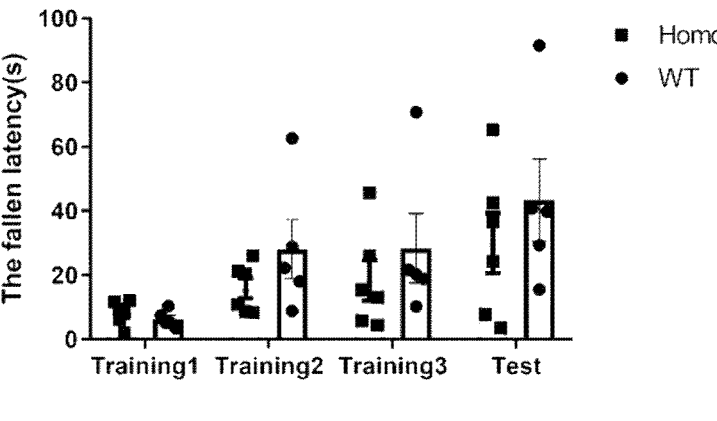
Figure 63A:
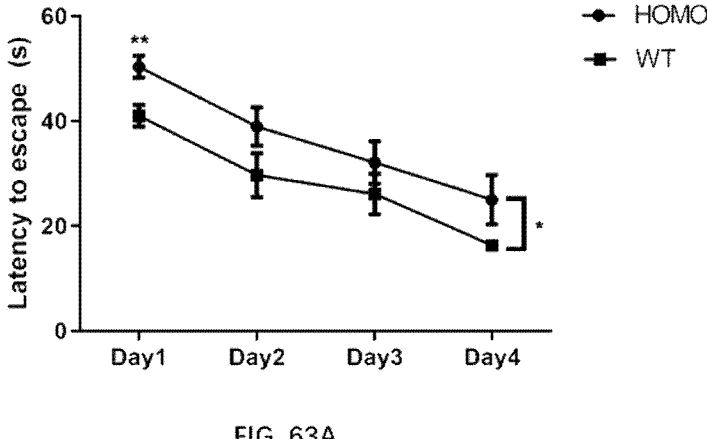
FIG. 63A-63B illustrate the result of morris water maze for 6-month old wildtype rats and 6-month old rats of the present disclosure.
Figure 63B:
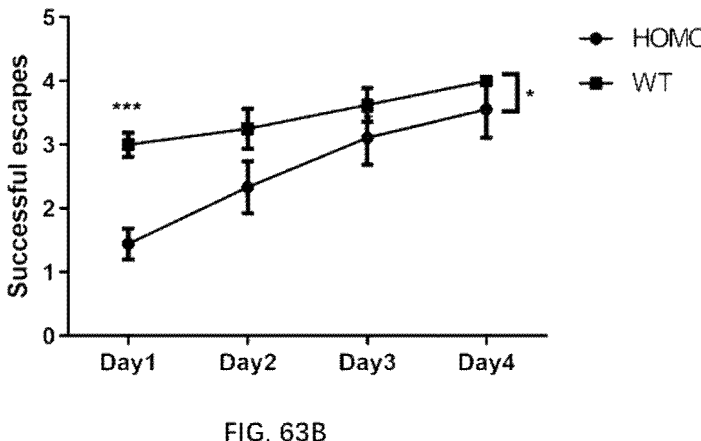
Figure 64A:
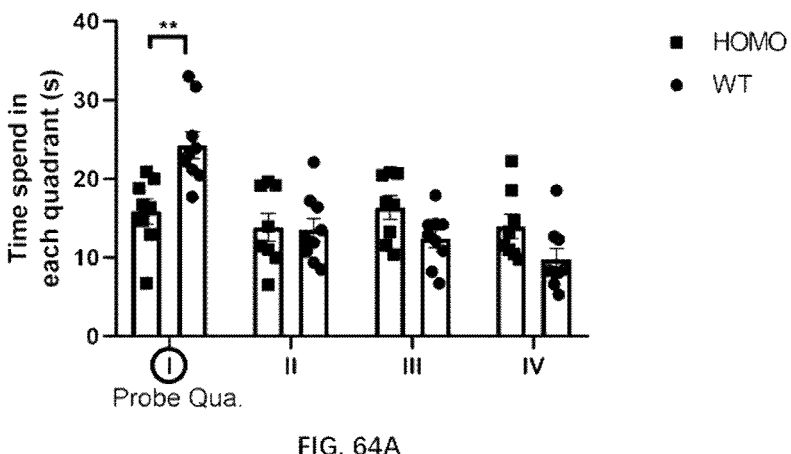
FIG. 64A-64B illustrates the result for morris water maze of 4-month old wildtype rats and 4-month old rats of the present disclosure.
Figure 64B:
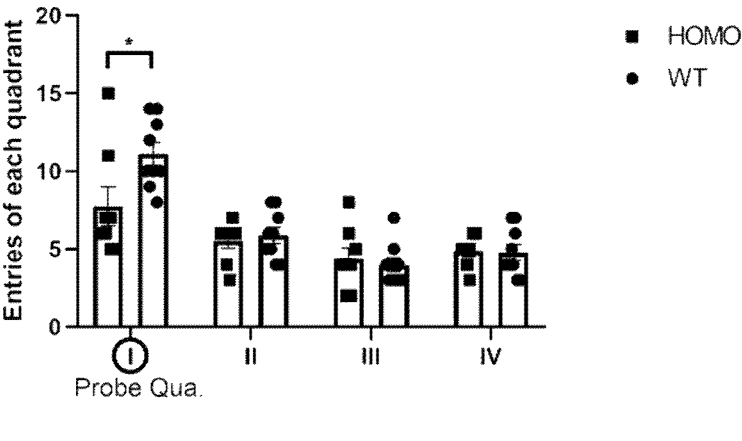
Figure 65A:
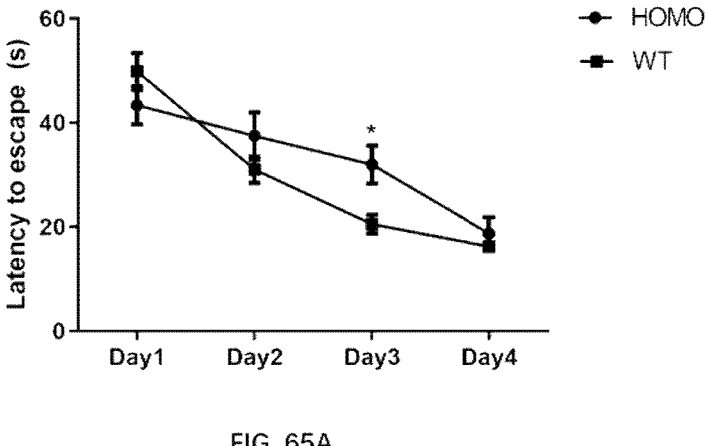
FIG. 65A-65B illustrates the result of morris water maze for 4-month old wildtype rats and 4-month old rats of the present disclosure.
Figure 65B:
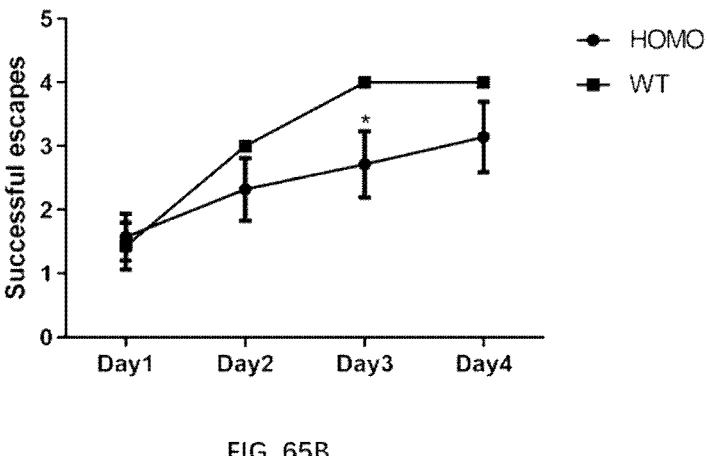

The results are shown in FIGS. 62A and 62B. It can be seen that comparing to the corresponding wildtype rats, the knock-in rats of the present disclosure (e.g., 4-month old and 6-month old, homozygous for the chimeric App gene) had similar locomotor activities.

Example 20

Morris Water Maze Test

Cognitive abilities of the rats according to the present disclosure were examined in a Morris water maze. The tests were conducted in a circular pool with a 150 cm diameter and filled to a depth of 22 cm with water (23±2° C.). The water was made cloudy with the addition of black ink into the water. Distinctive visual cues were set up on the wall surrounding the pool. A video camera was positioned above the water maze. The swim paths of the rats were tracked and analyzed by softwares. The water maze was equally divided into four logical quadrants that served as starting positions. All rats have been tested for their spatial learning abilities for 4 consecutive days, followed by a probe test on the fifth day. In the spatial learning task, a platform (with a diameter of 8 cm) was placed 2 cm beneath the water and fixed in the middle of the west quadrant, 45 cm from the maze wall. In this 4-day test, four swim trials were given per day, wherein each rat was released from a different quadrant in each trial. This was done in a pseudo-random manner and the starting quadrant used varied in different sessions. A maximum of 60-second was allowed for each trial. If the rat did not find the platform within 60 seconds, it was guided to the platform and allowed to remain there for 10-second. After each training trial, the rats were dried with paper towels and returned to their home cages for 50 seconds before the next trial, the intertrial interval was approximately 60 seconds. Both the latency to escape onto the platform and number of successful escapes were recorded. The probe test was performed after the 4-day spatial learning test. In the probe test, the hidden platform was removed. The time spent in each quadrant and the number of times entering in each quadrant were recorded.

The results are shown in FIGS. 63A, 63B, 64A, 64B, 65A and 65B. It can be seen that comparing to the corresponding wildtype rats, the knock-in rats of the present disclosure (e.g., 4-month old and 6-month old, homozygous for the chimeric App gene) showed worse spatial learning abilities.

Example 21

T-Maze Working Memory Test

Cognitive abilities of the rats according to the present disclosure were examined in a T-maze working memory test.

Animal Preparation

For the T maze tasks, the rats were food restricted to 85%-90% of their pre-experimental free-feeding weights with water available ad libitum. Sweet pellet (the bait) was given to the rats in their cage the day before the test. The rats were moved into the experiment room 1 hour prior to the start of the experiment.

Experiment Procedures:

Habituation to the maze (day 1): to train the rats to pick up food rewards in the maze, bait was placed in the food holders located in the end of both arms of the T-maze. Each time, one rat was placed into the maze and was allowed to explore the maze freely during this habituation session. The rats were retrieved from the maze after all baits were consumed.

Habituation to the maze (day 2): the procedure was the same as that in habituation day 1, except that two trails for each rat were given, and the process was repeated when it took the rat more than 5 minutes to retrieve all the baits.

Forced Choice Training: during the forced choice training, the rats received 4 different 2-trial sessions with an inter-trial interval of about 5 seconds. In the first trial, food was placed in both (right and left) arms of the T-maze. Access to either the right or the left arm was blocked, forcing the rat to enter the unblocked arm of the maze. After the rat obtained the food reward, it was taken out of the maze. The block to the opposite arm was then removed, and rat was placed back to the starting position. The selection of the initially blocked arm was random among the 4 sessions of the day.

Basal Training: during this training, the rats received 4 different 2-trial sessions with an inter-trial interval of about 5 seconds. In the first trial, food was placed in both (right and left) arms of the T-maze. Access to either the right or the left arm of the T-maze was blocked, forcing the rat to enter the unblocked arm of the maze. After the rat obtained the food reward, it was taken out of the maze. The block to the opposite arm was then removed, and rat was placed back to the starting position. The selection of the initially blocked arm was random among the 4 sessions of the day. If the rats entered the correct arm, it was considered to have made a right choice. As soon as the animal reached a selection accuracy of 75% in 3 consecutive days, a working memory test was performed.

The Working Memory Test: the same procedure was employed as in the basal training, except that there were three different inter-trial intervals (between trial 1 and 2 for each session): 5 seconds, 120 seconds and 600 seconds. During these sessions, the rats received 6 sessions of 2-trial tests per day. Different inter-trial intervals were randomly applied over the 6 sessions in a day, with each interval being applied twice during each day of training per rat. The working memory sessions were performed in two consecutive days.

Figure 66A:
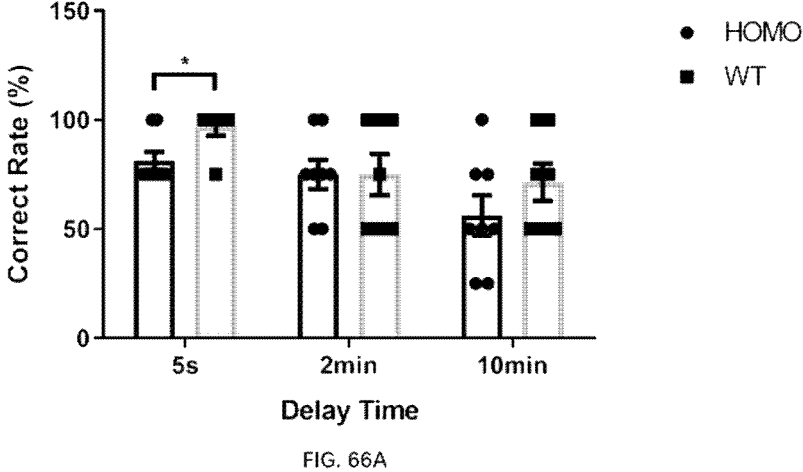
FIG. 66A-66B illustrates the result of T-maze working memory test for 6-month old wildtype rats and 6-month old rats of the present disclosure.
Figure 66B:
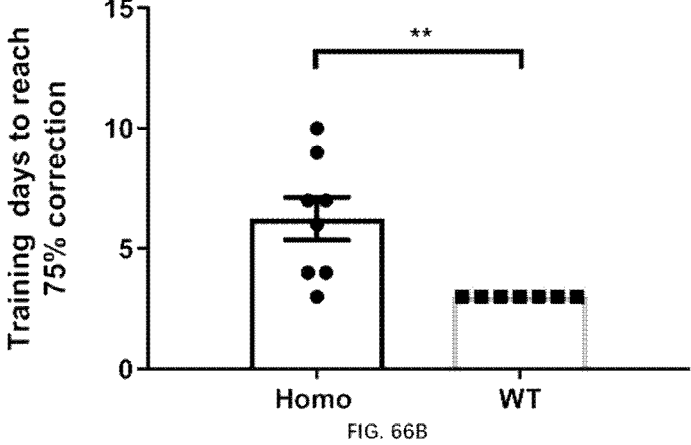

The results are shown in FIGS. 66A-66B. It can be seen that comparing to the corresponding wildtype rats, the knock-in rats of the present disclosure (e.g., 6-month old, homozygous for the chimeric App gene) achieved lower accuracy rate (FIG. 66A), and during the habituation periods, the knock-in rats spent more training days to reach the 75% accuracy rate. These results indicate that the knock-in rats of the present disclosure have impaired cognitive abilities, such as impaired learning and memory functions.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

---

What is claimed is:

1. A rat or a living part thereof, wherein said rat expresses a modified amyloid precursor protein (APP) as set forth in SEQ ID NO: 2, wherein tau pathology and neuronal loss are detectable in said rat or the living part thereof, wherein the tau pathology comprises hyper-phosphorylation of tau protein and aggregation of tau protein.

2. The rat or the living part thereof according to claim 1, wherein the expression level of the modified APP differs by less than 10% from that of an expression level in a corresponding wildtype rat.

3. The rat or the living part thereof according to claim 1, wherein one or more of the following effects can be detected:

1) said rat shows Aβ oligomers at an age of 3 months or earlier;
  2) said rat shows an Amyloid plaque at an age of 4 months or earlier;
  3) no accumulation of Aβ peptide is detectable in said rat's cerebellum;
  4) gliosis is detectable in said rat or the living part thereof;
  5) synaptic degeneration is detectable in said rat or the living part thereof; and/or
  6) cognitive impairment is detectable in said rat compared to a corresponding wildtype rat;
  7) a change in brain morphology and/or weight is detectable in said rat or the living part thereof;
  8) necrosome formation is detectable in said rat or the living part thereof.

4. The rat or the living part thereof according to claim 3, wherein the number of Neu-N positive neurons is decreased in said rat or the living part thereof, compared to that in a corresponding wildtype rat.

5. The rat or the living part thereof according to claim 1, wherein said neuronal loss comprises apoptosis and/or necrosis of a neuronal cell.

6. The rat or the living part thereof according to claim 3, wherein said gliosis is detected and comprises microgliosis and/or astrocytosis.

7. The rat or living part thereof of claim 1 that is a knock-in rat.

8. The rat or living part thereof of claim 1, wherein necrosome formation is detectable in said rat or the living part thereof.

\* \* \* \* \*